(12) United States Patent
Wixey et al.

(10) Patent No.: US 12,383,268 B2
(45) Date of Patent: *Aug. 12, 2025

(54) SURGICAL INSTRUMENTS WITH SWITCHES FOR DEACTIVATING AND/OR IDENTIFYING STAPLER CARTRIDGES

(71) Applicant: INTUITIVE SURGICAL OPERATIONS, INC., Sunnyvale, CA (US)

(72) Inventors: Matthew Wixey, San Jose, CA (US); Atal Patel, Mission Viejo, CA (US); Babak D. Jasemian, Trabuco Canyon, CA (US); Nicholas Ragosta, San Francisco, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/212,746

(22) Filed: Jun. 22, 2023

(65) Prior Publication Data

US 2023/0329711 A1 Oct. 19, 2023

Related U.S. Application Data

(63) Continuation of application No. 17/414,805, filed as application No. PCT/US2019/066513 on Dec. 16, 2019, now Pat. No. 11,723,661.
(Continued)

(51) Int. Cl.
*A61B 17/072* (2006.01)
*A61B 34/30* (2016.01)
(Continued)

(52) U.S. Cl.
CPC ........ *A61B 17/07207* (2013.01); *A61B 34/30* (2016.02); *A61B 90/08* (2016.02);
(Continued)

(58) Field of Classification Search
CPC .... A61B 17/07207; A61B 2017/00017; A61B 2017/00039; A61B 2017/07271;
(Continued)

(56) References Cited

U.S. PATENT DOCUMENTS

| | | |
|---|---|---|
| 75,364 A | 3/1868 | Case |
| 4,305,539 A | 12/1981 | Korolkov et al. |

(Continued)

FOREIGN PATENT DOCUMENTS

| | | |
|---|---|---|
| CN | 103889344 A | 6/2014 |
| CN | 104042275 A | 9/2014 |

(Continued)

OTHER PUBLICATIONS

International Search Report and Written Opinion for Application No. PCT/US202 1/065544 mailed Jun. 2, 2022, 21 pages.
(Continued)

*Primary Examiner* — Thanh K Truong
*Assistant Examiner* — Linda J Hodge
(74) *Attorney, Agent, or Firm* — Farber LLC

(57) ABSTRACT

Surgical stapling instruments include mechanisms for identifying and/or deactivating stapler cartridge for use with the instruments. The stapling instrument includes a drive member for actuating a staple cartridge and a locking member movable from a disabled position permitting distal translation of the drive member through a staple firing stroke, to a locking position inhibiting distal translation of the drive member through the staple firing stroke. The staple cartridge may include a switch for maintaining the locking member in the disabled position. The switch may be further configured
(Continued)

to operate as a reload detection mechanism for determining the type of reload present in the surgical stapling instrument.

20 Claims, 30 Drawing Sheets

Related U.S. Application Data

(60) Provisional application No. 62/783,429, filed on Dec. 21, 2018.

(51) Int. Cl.
*A61B 90/00* (2016.01)
*A61B 90/90* (2016.01)
*A61B 17/00* (2006.01)

(52) U.S. Cl.
CPC .... *A61B 90/90* (2016.02); *A61B 2017/00017* (2013.01); *A61B 2017/00039* (2013.01); *A61B 2017/07271* (2013.01); *A61B 2017/07278* (2013.01); *A61B 2017/07285* (2013.01); *A61B 2090/0814* (2016.02)

(58) Field of Classification Search
CPC ........... A61B 2017/07278; A61B 2017/07285; A61B 90/08; A61B 2090/0814; A61B 90/90; A61B 34/30
See application file for complete search history.

(56) References Cited

U.S. PATENT DOCUMENTS

| | | | |
|---|---|---|---|
| 4,319,576 A | 3/1982 | Rothfuss | |
| 4,352,276 A | 10/1982 | Smith | |
| 4,403,892 A | 9/1983 | Kane | |
| 4,407,286 A | 10/1983 | Noiles et al. | |
| 4,429,695 A | 2/1984 | Green | |
| 4,509,518 A | 4/1985 | McGarry et al. | |
| 4,509,932 A | 4/1985 | Weible | |
| 4,605,001 A | 8/1986 | Rothfuss et al. | |
| 4,608,981 A | 9/1986 | Rothfuss et al. | |
| 4,610,383 A | 9/1986 | Rothfuss et al. | |
| 4,633,874 A | 1/1987 | Chow et al. | |
| 4,767,044 A | 8/1988 | Green | |
| 4,809,695 A | 3/1989 | Gwathmey et al. | |
| 4,848,637 A | 7/1989 | Pruitt | |
| 4,892,244 A | 1/1990 | Fox et al. | |
| 4,930,503 A | 6/1990 | Pruitt | |
| 4,978,049 A | 12/1990 | Green | |
| 5,027,834 A | 7/1991 | Pruitt | |
| 5,040,715 A | 8/1991 | Green et al. | |
| 5,133,735 A | 7/1992 | Slater et al. | |
| 5,133,736 A | 7/1992 | Bales, Jr. et al. | |
| 5,147,357 A | 9/1992 | Rose et al. | |
| 5,180,092 A | 1/1993 | Crainich | |
| 5,275,323 A | 1/1994 | Schulze et al. | |
| 5,307,976 A | 5/1994 | Olson et al. | |
| 5,312,023 A | 5/1994 | Green et al. | |
| 5,334,183 A | 8/1994 | Wuchinich | |
| 5,342,395 A | 8/1994 | Jarrett et al. | |
| 5,342,396 A | 8/1994 | Cook | |
| 5,366,133 A | 11/1994 | Geiste | |
| 5,452,836 A | 9/1995 | Huitema et al. | |
| 5,452,837 A | 9/1995 | Williamson, IV et al. | |
| 5,465,895 A | 11/1995 | Knodel et al. | |
| 5,480,089 A | 1/1996 | Blewett | |
| 5,484,095 A | 1/1996 | Green et al. | |
| 5,484,451 A | 1/1996 | Akopov et al. | |
| 5,487,500 A | 1/1996 | Knodel et al. | |
| 5,497,931 A | 3/1996 | Nakamura | |
| 5,533,521 A | 7/1996 | Granger | |
| 5,540,375 A | 7/1996 | Bolanos et al. | |
| 5,554,164 A | 9/1996 | Wilson et al. | |
| 5,560,530 A | 10/1996 | Bolanos et al. | |
| 5,562,239 A | 10/1996 | Boiarski et al. | |
| 5,564,615 A | 10/1996 | Bishop et al. | |
| 5,571,116 A | 11/1996 | Bolanos et al. | |
| 5,571,285 A | 11/1996 | Chow et al. | |
| 5,573,534 A | 11/1996 | Stone | |
| 5,615,820 A | 4/1997 | Viola | |
| 5,624,452 A | 4/1997 | Yates | |
| 5,628,446 A | 5/1997 | Geiste et al. | |
| 5,651,491 A * | 7/1997 | Heaton ............ A61B 17/07207 227/176.1 |
| 5,652,849 A | 7/1997 | Conway et al. | |
| 5,667,626 A | 9/1997 | Cayford et al. | |
| 5,673,840 A | 10/1997 | Schulze et al. | |
| 5,673,842 A | 10/1997 | Bittner et al. | |
| 5,676,674 A | 10/1997 | Bolanos et al. | |
| 5,688,269 A | 11/1997 | Newton et al. | |
| 5,690,269 A | 11/1997 | Bolanos et al. | |
| 5,693,042 A | 12/1997 | Boiarski et al. | |
| 5,697,542 A | 12/1997 | Knodel et al. | |
| 5,700,270 A | 12/1997 | Peyser et al. | |
| 5,700,276 A | 12/1997 | Benecke | |
| 5,709,680 A | 1/1998 | Yates et al. | |
| 5,738,474 A | 4/1998 | Blewett | |
| 5,752,644 A | 5/1998 | Bolanos et al. | |
| 5,752,973 A | 5/1998 | Kieturakis et al. | |
| 5,762,255 A | 6/1998 | Chrisman et al. | |
| 5,762,256 A | 6/1998 | Mastri et al. | |
| 5,779,130 A | 7/1998 | Alesi et al. | |
| 5,782,396 A | 7/1998 | Mastri et al. | |
| 5,792,135 A | 8/1998 | Madhani et al. | |
| 5,820,009 A | 10/1998 | Melling et al. | |
| 5,826,776 A | 10/1998 | Schulze et al. | |
| 5,833,695 A | 11/1998 | Yoon | |
| 5,865,361 A | 2/1999 | Milliman et al. | |
| 5,871,135 A | 2/1999 | Williamson et al. | |
| 5,911,353 A | 6/1999 | Bolanos et al. | |
| 5,915,616 A | 6/1999 | Viola et al. | |
| 5,919,198 A | 7/1999 | Graves, Jr. et al. | |
| 5,941,442 A | 8/1999 | Geiste et al. | |
| 5,954,259 A | 9/1999 | Viola et al. | |
| 5,959,892 A | 9/1999 | Lin et al. | |
| 6,032,849 A | 3/2000 | Mastri et al. | |
| 6,050,996 A | 4/2000 | Schmaltz et al. | |
| 6,079,606 A | 6/2000 | Milliman et al. | |
| 6,113,598 A | 9/2000 | Baker | |
| 6,126,666 A | 10/2000 | Trapp et al. | |
| 6,174,309 B1 | 1/2001 | Wrublewski et al. | |
| 6,202,914 B1 | 3/2001 | Geiste et al. | |
| 6,241,139 B1 | 6/2001 | Milliman et al. | |
| 6,250,532 B1 | 6/2001 | Green et al. | |
| 6,312,426 B1 | 11/2001 | Goldberg et al. | |
| 6,330,956 B1 | 12/2001 | Willinger | |
| 6,330,965 B1 | 12/2001 | Milliman et al. | |
| 6,488,196 B1 | 12/2002 | Fenton, Jr. | |
| 6,503,259 B2 | 1/2003 | Huxel et al. | |
| 6,585,735 B1 | 7/2003 | Frazier et al. | |
| 6,644,532 B2 | 11/2003 | Green et al. | |
| 6,656,193 B2 | 12/2003 | Grant et al. | |
| 6,669,073 B2 | 12/2003 | Milliman et al. | |
| 6,770,072 B1 | 8/2004 | Truckai et al. | |
| 6,786,382 B1 | 9/2004 | Hoffman | |
| 6,817,974 B2 | 11/2004 | Cooper et al. | |
| 6,840,938 B1 | 1/2005 | Morley et al. | |
| 6,877,647 B2 | 4/2005 | Green et al. | |
| 6,905,057 B2 | 6/2005 | Swayze et al. | |
| 6,953,139 B2 | 10/2005 | Milliman et al. | |
| 6,959,852 B2 | 11/2005 | Shelton, IV et al. | |
| 6,964,363 B2 | 11/2005 | Wales et al. | |
| 6,978,921 B2 | 12/2005 | Shelton, IV et al. | |
| 6,978,922 B2 | 12/2005 | Bilotti et al. | |
| 6,986,451 B1 | 1/2006 | Mastri et al. | |
| 6,988,649 B2 | 1/2006 | Shelton, IV et al. | |
| 7,000,818 B2 | 2/2006 | Shelton, IV et al. | |
| 7,000,819 B2 | 2/2006 | Swayze et al. | |
| 7,044,352 B2 | 5/2006 | Shelton, IV et al. | |
| 7,044,353 B2 | 5/2006 | Mastri et al. | |
| 7,055,731 B2 | 6/2006 | Shelton, IV et al. | |
| 7,059,508 B2 | 6/2006 | Shelton, IV et al. | |
| 7,070,083 B2 | 7/2006 | Jankowski | |

(56) References Cited

U.S. PATENT DOCUMENTS

| | | |
|---|---|---|
| 7,114,642 B2 | 10/2006 | Whitman |
| 7,128,253 B2 | 10/2006 | Mastri et al. |
| 7,140,527 B2 | 11/2006 | Ehrenfels et al. |
| 7,140,528 B2 | 11/2006 | Shelton, IV et al. |
| 7,258,262 B2 | 8/2007 | Mastri et al. |
| 7,296,722 B2 | 11/2007 | Ivanko |
| 7,308,998 B2 | 12/2007 | Mastri et al. |
| 7,328,828 B2 | 2/2008 | Ortiz et al. |
| 7,380,695 B2 | 6/2008 | Doll et al. |
| 7,380,696 B2 | 6/2008 | Shelton, IV et al. |
| 7,398,908 B2 | 7/2008 | Holsten et al. |
| 7,401,721 B2 | 7/2008 | Holsten et al. |
| 7,407,075 B2 | 8/2008 | Holsten et al. |
| 7,455,676 B2 | 11/2008 | Holsten et al. |
| 7,472,814 B2 | 1/2009 | Mastri et al. |
| 7,481,349 B2 | 1/2009 | Holsten et al. |
| 7,491,202 B2 | 2/2009 | Odom et al. |
| 7,494,039 B2 | 2/2009 | Racenet et al. |
| 7,565,993 B2 | 7/2009 | Milliman et al. |
| 7,588,174 B2 | 9/2009 | Holsten et al. |
| 7,654,431 B2 | 2/2010 | Hueil et al. |
| 7,658,312 B2 | 2/2010 | Vidal et al. |
| 7,673,783 B2 | 3/2010 | Morgan et al. |
| 7,699,835 B2 | 4/2010 | Lee et al. |
| 7,721,930 B2 | 5/2010 | McKenna et al. |
| 7,726,539 B2 | 6/2010 | Holsten et al. |
| 7,770,774 B2 | 8/2010 | Mastri et al. |
| 7,794,475 B2 | 9/2010 | Hess et al. |
| 7,832,611 B2 | 11/2010 | Boyden et al. |
| 7,837,079 B2 | 11/2010 | Holsten et al. |
| 7,866,526 B2 | 1/2011 | Green et al. |
| 7,942,303 B2 | 5/2011 | Shah et al. |
| 7,950,561 B2 | 5/2011 | Aranyi |
| 8,070,035 B2 | 12/2011 | Holsten et al. |
| 8,083,118 B2 | 12/2011 | Milliman et al. |
| 8,127,975 B2 | 3/2012 | Olson et al. |
| 8,157,152 B2 | 4/2012 | Holsten et al. |
| 8,272,553 B2 | 9/2012 | Mastri et al. |
| 8,308,042 B2 | 11/2012 | Aranyi |
| 8,348,127 B2 | 1/2013 | Marczyk |
| 8,365,972 B2 | 2/2013 | Aranyi et al. |
| 8,371,492 B2 | 2/2013 | Aranyi et al. |
| 8,439,246 B1 | 5/2013 | Knodel |
| 8,490,851 B2 | 7/2013 | Blier et al. |
| 8,551,091 B2 | 10/2013 | Couture et al. |
| 8,573,465 B2 | 11/2013 | Shelton, IV |
| 8,579,178 B2 | 11/2013 | Holsten et al. |
| 8,608,047 B2 | 12/2013 | Holsten et al. |
| 8,672,206 B2 | 3/2014 | Aranyi et al. |
| 8,672,939 B2 | 3/2014 | Garrison |
| 8,701,960 B1 | 4/2014 | Manoux et al. |
| 8,783,541 B2 | 7/2014 | Shelton, IV et al. |
| 8,800,841 B2 | 8/2014 | Ellerhorst et al. |
| 8,834,518 B2 | 9/2014 | Faller et al. |
| 8,851,355 B2 | 10/2014 | Aranyi et al. |
| 8,852,174 B2 | 10/2014 | Burbank |
| 8,858,547 B2 | 10/2014 | Brogna |
| 8,864,010 B2 | 10/2014 | Williams |
| 8,905,287 B2 | 12/2014 | Racenet et al. |
| 8,925,785 B2 | 1/2015 | Holsten et al. |
| 9,010,606 B2 | 4/2015 | Aranyi et al. |
| 9,016,545 B2 | 4/2015 | Aranyi et al. |
| 9,055,961 B2 | 6/2015 | Manzo et al. |
| 9,192,378 B2 | 11/2015 | Aranyi et al. |
| 9,192,379 B2 | 11/2015 | Aranyi et al. |
| 9,211,120 B2 | 12/2015 | Scheib et al. |
| 9,216,019 B2 | 12/2015 | Schmid et al. |
| 9,307,986 B2 | 4/2016 | Hall et al. |
| 9,345,479 B2 | 5/2016 | Racenet et al. |
| 9,717,497 B2 | 8/2017 | Zerkle et al. |
| 9,717,498 B2 | 8/2017 | Aranyi et al. |
| 9,936,949 B2 | 4/2018 | Measamer et al. |
| 10,111,659 B2 | 10/2018 | Racenet et al. |
| 10,130,367 B2 | 11/2018 | Cappola et al. |
| 10,231,732 B1 | 3/2019 | Racenet et al. |
| 10,231,733 B2 | 3/2019 | Ehrenfels et al. |
| 10,285,693 B2 | 5/2019 | Kimsey et al. |
| 10,335,147 B2 | 7/2019 | Rector et al. |
| 10,363,037 B2 | 7/2019 | Aronhalt et al. |
| 10,646,219 B2 | 5/2020 | Racenet et al. |
| 10,828,027 B2 | 11/2020 | Racenet et al. |
| 10,863,988 B2 | 12/2020 | Patel et al. |
| 10,973,517 B2 | 4/2021 | Wixey |
| 11,234,700 B2 | 2/2022 | Ragosta et al. |
| 11,439,390 B2 | 9/2022 | Patel et al. |
| 11,504,124 B2 | 11/2022 | Patel et al. |
| 11,517,312 B2 | 12/2022 | Wixey |
| 11,642,129 B2 | 5/2023 | Burbank |
| 11,696,758 B2 | 7/2023 | Murphy et al. |
| 11,723,661 B2 * | 8/2023 | Wixey .................. A61B 90/90 227/175.4 |
| 11,759,202 B2 | 9/2023 | Morgan et al. |
| 11,786,325 B2 | 10/2023 | Mustufa et al. |
| 11,806,015 B2 | 11/2023 | Wixey et al. |
| 11,857,188 B2 | 1/2024 | Hites |
| 11,864,762 B2 | 1/2024 | Wixey |
| 11,896,224 B2 | 2/2024 | Wellman |
| 11,944,301 B2 | 4/2024 | Wixey et al. |
| 11,944,302 B2 | 4/2024 | Wixey et al. |
| 11,986,184 B2 | 5/2024 | Patel et al. |
| 12,011,168 B2 | 6/2024 | Wixey |
| 12,029,426 B2 | 7/2024 | Millman et al. |
| 12,029,473 B2 | 7/2024 | Whitlock et al. |
| 2002/0165562 A1 | 11/2002 | Grant et al. |
| 2002/0177843 A1 | 11/2002 | Anderson et al. |
| 2002/0188293 A1 | 12/2002 | Manzo |
| 2002/0188294 A1 | 12/2002 | Couture et al. |
| 2003/0135204 A1 | 7/2003 | Lee et al. |
| 2003/0144652 A1 | 7/2003 | Baker et al. |
| 2003/0171747 A1 | 9/2003 | Kanehira et al. |
| 2003/0181910 A1 | 9/2003 | Dycus et al. |
| 2004/0006340 A1 | 1/2004 | Latterell et al. |
| 2004/0049185 A1 | 3/2004 | Latterell et al. |
| 2004/0143263 A1 | 7/2004 | Schechter et al. |
| 2004/0232199 A1 | 11/2004 | Shelton et al. |
| 2004/0267310 A1 | 12/2004 | Racenet et al. |
| 2005/0006430 A1 | 1/2005 | Wales |
| 2005/0006434 A1 | 1/2005 | Wales et al. |
| 2005/0021027 A1 | 1/2005 | Shields et al. |
| 2005/0070925 A1 | 3/2005 | Shelton, IV et al. |
| 2005/0070958 A1 | 3/2005 | Swayze et al. |
| 2005/0101991 A1 | 5/2005 | Ahlberg et al. |
| 2005/0113826 A1 | 5/2005 | Johnson et al. |
| 2005/0171533 A1 | 8/2005 | Latterell et al. |
| 2005/0178813 A1 | 8/2005 | Swayze et al. |
| 2005/0187576 A1 | 8/2005 | Whitman et al. |
| 2005/0273084 A1 | 12/2005 | Hinman et al. |
| 2005/0273085 A1 | 12/2005 | Hinman et al. |
| 2006/0000868 A1 | 1/2006 | Shelton, IV et al. |
| 2006/0016853 A1 | 1/2006 | Racenet |
| 2006/0022014 A1 | 2/2006 | Shelton, IV et al. |
| 2006/0022015 A1 | 2/2006 | Shelton et al. |
| 2006/0024817 A1 | 2/2006 | Deguchi et al. |
| 2006/0025809 A1 | 2/2006 | Shelton, IV |
| 2006/0025810 A1 | 2/2006 | Shelton, IV |
| 2006/0025811 A1 | 2/2006 | Shelton, IV |
| 2006/0025812 A1 | 2/2006 | Shelton, IV |
| 2006/0025813 A1 | 2/2006 | Shelton, IV et al. |
| 2006/0025816 A1 | 2/2006 | Shelton, IV |
| 2006/0049230 A1 | 3/2006 | Shelton, IV et al. |
| 2006/0097026 A1 | 5/2006 | Shelton, IV |
| 2006/0111209 A1 | 5/2006 | Hinman et al. |
| 2006/0111210 A1 | 5/2006 | Hinman |
| 2006/0124689 A1 | 6/2006 | Arad et al. |
| 2006/0161190 A1 | 7/2006 | Gadberry et al. |
| 2006/0190031 A1 | 8/2006 | Wales et al. |
| 2006/0199999 A1 | 9/2006 | Ikeda et al. |
| 2006/0217706 A1 | 9/2006 | Lau et al. |
| 2006/0217709 A1 | 9/2006 | Couture et al. |
| 2006/0271042 A1 | 11/2006 | Latterell et al. |
| 2007/0010838 A1 | 1/2007 | Shelton, IV et al. |
| 2007/0045379 A1 | 3/2007 | Shelton, IV |
| 2007/0250113 A1 | 10/2007 | Hegeman et al. |
| 2007/0262116 A1 | 11/2007 | Hueil et al. |

(56) References Cited

U.S. PATENT DOCUMENTS

| | | |
|---|---|---|
| 2008/0023522 A1 | 1/2008 | Olson et al. |
| 2008/0029577 A1* | 2/2008 | Shelton ............... A61B 17/072 227/176.1 |
| 2008/0078804 A1 | 4/2008 | Shelton et al. |
| 2008/0086114 A1 | 4/2008 | Schmitz et al. |
| 2008/0108446 A1 | 5/2008 | Faude |
| 2008/0196533 A1 | 8/2008 | Bergamasco et al. |
| 2008/0210738 A1 | 9/2008 | Shelton et al. |
| 2008/0308607 A1 | 12/2008 | Timm et al. |
| 2009/0277947 A1 | 11/2009 | Viola |
| 2010/0006620 A1 | 1/2010 | Sorrentino et al. |
| 2010/0057081 A1 | 3/2010 | Hanna |
| 2010/0076474 A1 | 3/2010 | Yates et al. |
| 2010/0108740 A1 | 5/2010 | Pastorelli et al. |
| 2010/0145334 A1 | 6/2010 | Olson et al. |
| 2010/0179545 A1 | 7/2010 | Twomey et al. |
| 2010/0198248 A1 | 8/2010 | Vakharia |
| 2010/0213240 A1 | 8/2010 | Kostrzewski |
| 2010/0331857 A1 | 12/2010 | Doyle et al. |
| 2011/0022078 A1 | 1/2011 | Hinman |
| 2011/0036891 A1 | 2/2011 | Zemlok et al. |
| 2011/0087238 A1 | 4/2011 | Wang et al. |
| 2011/0118707 A1 | 5/2011 | Burbank |
| 2011/0118778 A1 | 5/2011 | Burbank |
| 2011/0121050 A1 | 5/2011 | Nicholas et al. |
| 2011/0152879 A1 | 6/2011 | Williams |
| 2011/0174863 A1 | 7/2011 | Shelton, IV et al. |
| 2011/0186614 A1 | 8/2011 | Kasvikis |
| 2011/0251612 A1 | 10/2011 | Faller et al. |
| 2011/0251613 A1 | 10/2011 | Guerra et al. |
| 2011/0282339 A1 | 11/2011 | Weizman et al. |
| 2011/0288573 A1 | 11/2011 | Yates et al. |
| 2011/0290851 A1 | 12/2011 | Shelton, IV |
| 2011/0290853 A1 | 12/2011 | Shelton, IV et al. |
| 2011/0290854 A1 | 12/2011 | Timm et al. |
| 2011/0295270 A1 | 12/2011 | Giordano et al. |
| 2011/0301603 A1 | 12/2011 | Kerr et al. |
| 2011/0319886 A1 | 12/2011 | Chojin et al. |
| 2012/0000962 A1 | 1/2012 | Racenet et al. |
| 2012/0022584 A1 | 1/2012 | Donnigan et al. |
| 2012/0071891 A1 | 3/2012 | Itkowitz et al. |
| 2012/0205419 A1 | 8/2012 | Weir et al. |
| 2012/0223121 A1 | 9/2012 | Viola et al. |
| 2012/0228358 A1* | 9/2012 | Zemlok ............... A61B 17/072 227/176.1 |
| 2012/0248167 A1 | 10/2012 | Flanagan et al. |
| 2012/0255986 A1 | 10/2012 | Petty et al. |
| 2012/0289999 A1 | 11/2012 | Frank |
| 2012/0298719 A1 | 11/2012 | Shelton, IV et al. |
| 2013/0015231 A1 | 1/2013 | Kostrzewski |
| 2013/0046303 A1 | 2/2013 | Evans et al. |
| 2013/0056521 A1 | 3/2013 | Swensgard |
| 2013/0068821 A1 | 3/2013 | Huitema et al. |
| 2013/0075448 A1 | 3/2013 | Schmid et al. |
| 2013/0087599 A1 | 4/2013 | Krumanaker et al. |
| 2013/0098965 A1 | 4/2013 | Kostrzewski et al. |
| 2013/0126586 A1 | 5/2013 | Zhang et al. |
| 2013/0148577 A1 | 6/2013 | Terry et al. |
| 2013/0248577 A1 | 9/2013 | Leimbach et al. |
| 2013/0277410 A1 | 10/2013 | Fernandez et al. |
| 2013/0296922 A1 | 11/2013 | Allen, IV et al. |
| 2013/0327808 A1* | 12/2013 | Chen ............... A61B 17/07207 227/175.2 |
| 2014/0001236 A1 | 1/2014 | Shelton, IV et al. |
| 2014/0005653 A1 | 1/2014 | Shelton, IV et al. |
| 2014/0005654 A1 | 1/2014 | Batross et al. |
| 2014/0021239 A1 | 1/2014 | Kostrzewski |
| 2014/0025071 A1 | 1/2014 | Sims et al. |
| 2014/0027492 A1 | 1/2014 | Williams |
| 2014/0100569 A1 | 4/2014 | Lawes et al. |
| 2014/0100600 A1 | 4/2014 | Kendrick |
| 2014/0103093 A1 | 4/2014 | Koch, Jr. et al. |
| 2014/0110455 A1* | 4/2014 | Ingmanson .......... A61B 17/072 227/176.1 |
| 2014/0175152 A1 | 6/2014 | Hess et al. |
| 2014/0180286 A1 | 6/2014 | Marczyk et al. |
| 2014/0183244 A1 | 7/2014 | Duque et al. |
| 2014/0200596 A1 | 7/2014 | Weir et al. |
| 2014/0200612 A1 | 7/2014 | Weir et al. |
| 2014/0200851 A1 | 7/2014 | Weir et al. |
| 2014/0214049 A1 | 7/2014 | Jeong et al. |
| 2014/0239036 A1 | 8/2014 | Zerkle et al. |
| 2014/0239044 A1 | 8/2014 | Hoffman |
| 2014/0246477 A1 | 9/2014 | Koch, Jr. et al. |
| 2014/0249557 A1 | 9/2014 | Koch, Jr. et al. |
| 2014/0257331 A1 | 9/2014 | Kim et al. |
| 2014/0263546 A1 | 9/2014 | Aranyi |
| 2014/0263552 A1 | 9/2014 | Hall et al. |
| 2014/0263559 A1 | 9/2014 | Williams et al. |
| 2014/0263567 A1 | 9/2014 | Williams et al. |
| 2014/0263569 A1 | 9/2014 | Williams et al. |
| 2014/0276731 A1 | 9/2014 | Voegele et al. |
| 2014/0276776 A1 | 9/2014 | Parihar et al. |
| 2014/0284372 A1 | 9/2014 | Kostrzewski |
| 2014/0305989 A1 | 10/2014 | Parihar et al. |
| 2014/0343550 A1 | 11/2014 | Faller et al. |
| 2014/0343569 A1 | 11/2014 | Turner |
| 2014/0364851 A1 | 12/2014 | Batross et al. |
| 2015/0073746 A1 | 3/2015 | Gris et al. |
| 2015/0088131 A1 | 3/2015 | Weisshaupt et al. |
| 2015/0141981 A1 | 5/2015 | Price et al. |
| 2015/0141993 A1 | 5/2015 | Schechter et al. |
| 2015/0173756 A1 | 6/2015 | Baxter, III et al. |
| 2015/0173789 A1 | 6/2015 | Baxter, III et al. |
| 2015/0209030 A1 | 7/2015 | Kostrzewski et al. |
| 2015/0209037 A1 | 7/2015 | Kostrzewski et al. |
| 2015/0250530 A1 | 9/2015 | Manzo et al. |
| 2015/0256609 A1 | 9/2015 | Morton et al. |
| 2015/0272575 A1 | 10/2015 | Leimbach et al. |
| 2015/0272576 A1 | 10/2015 | Cappola |
| 2015/0272606 A1 | 10/2015 | Nobis |
| 2015/0297227 A1 | 10/2015 | Huitema et al. |
| 2015/0297230 A1 | 10/2015 | Schellin et al. |
| 2015/0297235 A1 | 10/2015 | Harris et al. |
| 2015/0369277 A1 | 12/2015 | Fevre et al. |
| 2015/0374396 A1 | 12/2015 | Strobl et al. |
| 2016/0038227 A1 | 2/2016 | Garrison |
| 2016/0058450 A1 | 3/2016 | Shelton, IV et al. |
| 2016/0066916 A1 | 3/2016 | Overmyer et al. |
| 2016/0089148 A1 | 3/2016 | Harris et al. |
| 2016/0120544 A1 | 5/2016 | Shelton, IV et al. |
| 2016/0157863 A1 | 6/2016 | Williams et al. |
| 2016/0174977 A1* | 6/2016 | Lytle, IV ............. A61B 17/068 227/180.1 |
| 2016/0175033 A1 | 6/2016 | Le |
| 2016/0192999 A1 | 7/2016 | Stulen et al. |
| 2016/0199124 A1 | 7/2016 | Thomas et al. |
| 2016/0235473 A1 | 8/2016 | Hagland |
| 2016/0235489 A1 | 8/2016 | Gombert et al. |
| 2016/0242782 A1 | 8/2016 | Shelton, IV et al. |
| 2016/0249921 A1 | 9/2016 | Cappola et al. |
| 2016/0270780 A1 | 9/2016 | Hall et al. |
| 2016/0287251 A1 | 10/2016 | Shelton, IV et al. |
| 2016/0287316 A1 | 10/2016 | Worrell et al. |
| 2016/0296226 A1 | 10/2016 | Kostrzewski |
| 2016/0317216 A1 | 11/2016 | Hermes et al. |
| 2016/0338764 A1 | 11/2016 | Krastins et al. |
| 2017/0010578 A1 | 1/2017 | Miyakawa |
| 2017/0042604 A1 | 2/2017 | McFarland et al. |
| 2017/0056098 A1 | 3/2017 | Crews et al. |
| 2017/0065331 A1 | 3/2017 | Mayer et al. |
| 2017/0079710 A1 | 3/2017 | Deville et al. |
| 2017/0097035 A1 | 4/2017 | Zimmerman et al. |
| 2017/0105754 A1 | 4/2017 | Boudreaux et al. |
| 2017/0135746 A1 | 5/2017 | Tetzlaff et al. |
| 2017/0143335 A1 | 5/2017 | Gupta et al. |
| 2017/0156788 A1 | 6/2017 | Johnson et al. |
| 2017/0189028 A1 | 7/2017 | Aranyi |
| 2017/0231653 A1 | 8/2017 | Kapadia |
| 2017/0245857 A1 | 8/2017 | Shelton, IV et al. |
| 2017/0290584 A1 | 10/2017 | Jasemian et al. |
| 2017/0296172 A1 | 10/2017 | Harris et al. |
| 2017/0296173 A1 | 10/2017 | Shelton, IV et al. |
| 2018/0008265 A1 | 1/2018 | Hatanaka et al. |

(56) References Cited

U.S. PATENT DOCUMENTS

| | | |
|---|---|---|
| 2018/0021042 A1 | 1/2018 | Nicholas et al. |
| 2018/0125570 A1 | 5/2018 | Rioux |
| 2018/0161052 A1 | 6/2018 | Weir et al. |
| 2018/0168581 A1 | 6/2018 | Hunter et al. |
| 2018/0168585 A1 | 6/2018 | Shelton, IV et al. |
| 2018/0168620 A1 | 6/2018 | Huang et al. |
| 2018/0168622 A1 | 6/2018 | Shelton, IV et al. |
| 2018/0168628 A1 | 6/2018 | Hunter et al. |
| 2018/0168637 A1 | 6/2018 | Harris et al. |
| 2018/0168641 A1 | 6/2018 | Harris et al. |
| 2018/0168642 A1 | 6/2018 | Shelton, IV et al. |
| 2018/0168644 A1 | 6/2018 | Shelton, IV et al. |
| 2018/0168649 A1 | 6/2018 | Shelton, IV et al. |
| 2018/0168650 A1 | 6/2018 | Shelton, IV et al. |
| 2018/0206844 A1 | 7/2018 | Harris et al. |
| 2018/0214200 A1 | 8/2018 | Nanditale et al. |
| 2018/0232951 A1 | 8/2018 | Alterovitz et al. |
| 2018/0296213 A1 | 10/2018 | Strobl |
| 2018/0310935 A1 | 11/2018 | Wixey |
| 2018/0310948 A1 | 11/2018 | Stamm et al. |
| 2018/0317915 A1 | 11/2018 | McDonald, II |
| 2019/0000454 A1 | 1/2019 | Swayze et al. |
| 2019/0000525 A1 | 1/2019 | Messerly et al. |
| 2019/0015124 A1 | 1/2019 | Williams et al. |
| 2019/0029746 A1 | 1/2019 | Dudhedia et al. |
| 2019/0059894 A1 | 2/2019 | Kumada et al. |
| 2019/0076143 A1 | 3/2019 | Smith |
| 2019/0083086 A1 | 3/2019 | Klaffenböck et al. |
| 2019/0099181 A1* | 4/2019 | Shelton, IV ....... A61B 17/0682 |
| 2019/0125347 A1 | 5/2019 | Stokes et al. |
| 2019/0133571 A1 | 5/2019 | Racenet et al. |
| 2019/0142531 A1 | 5/2019 | Wentworth et al. |
| 2019/0192137 A1 | 6/2019 | Shelton, IV et al. |
| 2019/0201146 A1 | 7/2019 | Shelton, IV et al. |
| 2019/0231350 A1 | 8/2019 | Scott et al. |
| 2019/0239881 A1 | 8/2019 | Laurent et al. |
| 2019/0290374 A1 | 9/2019 | Ramadorai |
| 2019/0298346 A1 | 10/2019 | Shelton, IV et al. |
| 2019/0298356 A1 | 10/2019 | Shelton, IV et al. |
| 2019/0314107 A1 | 10/2019 | Worrell et al. |
| 2019/0365458 A1 | 12/2019 | Whitlock et al. |
| 2020/0205811 A1 | 7/2020 | Posey et al. |
| 2021/0000557 A1 | 1/2021 | Mustufa et al. |
| 2021/0161529 A1 | 6/2021 | Wixey |
| 2021/0177412 A1 | 6/2021 | Wilson et al. |
| 2021/0177495 A1 | 6/2021 | Ross et al. |
| 2021/0177500 A1 | 6/2021 | Khalaji |
| 2021/0196350 A1 | 7/2021 | Fiebig et al. |
| 2021/0236119 A1 | 8/2021 | Chavan et al. |
| 2021/0267596 A1 | 9/2021 | Fanelli et al. |
| 2021/0386427 A1 | 12/2021 | Millman et al. |
| 2022/0015762 A1 | 1/2022 | Wixey et al. |
| 2022/0015763 A1 | 1/2022 | Wixey et al. |
| 2022/0015823 A1 | 1/2022 | Wilson et al. |
| 2022/0054130 A1 | 2/2022 | Overmyer et al. |
| 2022/0061836 A1 | 3/2022 | Parihar et al. |
| 2022/0061840 A1 | 3/2022 | Hites |
| 2022/0061841 A1 | 3/2022 | Wixey et al. |
| 2022/0071632 A1 | 3/2022 | Patel et al. |
| 2022/0079585 A1 | 3/2022 | Egan |
| 2022/0125428 A1 | 4/2022 | Ragosta et al. |
| 2022/0160358 A1 | 5/2022 | Wixey |
| 2022/0167985 A1 | 6/2022 | George et al. |
| 2022/0183686 A1 | 6/2022 | Wixey et al. |
| 2022/0192665 A1 | 6/2022 | Wellman |
| 2022/0346790 A1 | 11/2022 | Wellman |
| 2022/0378537 A1 | 12/2022 | Hites et al. |
| 2022/0395270 A1 | 12/2022 | Patel et al. |
| 2023/0020577 A1 | 1/2023 | Kerver et al. |
| 2023/0047784 A1 | 2/2023 | Patel et al. |
| 2023/0052074 A1 | 2/2023 | Wixey |
| 2023/0101993 A1 | 3/2023 | Baril et al. |
| 2023/0210527 A1 | 7/2023 | Shelton, IV et al. |
| 2023/0225731 A1 | 7/2023 | Burbank |
| 2024/0023961 A1 | 1/2024 | Wixey et al. |
| 2024/0065690 A1 | 2/2024 | Jasemian et al. |
| 2024/0081824 A1 | 3/2024 | Hites |
| 2024/0108343 A1 | 4/2024 | Wixey |
| 2024/0138834 A1 | 5/2024 | Wellman |
| 2024/0252171 A1 | 8/2024 | Wixey et al. |
| 2024/0260959 A1 | 8/2024 | Wixey et al. |

FOREIGN PATENT DOCUMENTS

| | | |
|---|---|---|
| CN | 105007836 A | 10/2015 |
| CN | 105769331 A | 7/2016 |
| CN | 106232026 A | 12/2016 |
| CN | 106491203 A | 3/2017 |
| CN | 107920819 A | 4/2018 |
| CN | 108024809 A | 5/2018 |
| CN | 112165909 A | 1/2021 |
| DE | 694747 C | 8/1940 |
| DE | 3724525 C1 | 5/1988 |
| DE | 102012103503 A1 | 10/2013 |
| EP | 0277532 B1 | 8/1990 |
| EP | 0469396 A1 | 2/1992 |
| EP | 0277529 B1 | 4/1993 |
| EP | 0641546 A1 | 3/1995 |
| EP | 0986336 A1 | 3/2000 |
| EP | 1090592 A1 | 4/2001 |
| EP | 1479348 A1 | 11/2004 |
| EP | 1728473 A1 | 12/2006 |
| EP | 1479346 B1 | 1/2007 |
| EP | 1621141-81 | 7/2007 |
| EP | 2374419 A2 | 10/2011 |
| EP | 1316290 B1 | 2/2012 |
| EP | 2517639 A1 | 10/2012 |
| EP | 2540231 A2 | 1/2013 |
| EP | 1754445 B1 | 10/2013 |
| EP | 2777529 A1 | 9/2014 |
| EP | 2777530 A1 | 9/2014 |
| EP | 2777532 A2 | 9/2014 |
| EP | 2944275 A2 | 11/2015 |
| EP | 2992834 A1 | 3/2016 |
| EP | 2992849 A1 | 3/2016 |
| EP | 3000408 A2 | 3/2016 |
| EP | 3120780 A2 | 1/2017 |
| EP | 3135225 A2 | 3/2017 |
| EP | 3158947 A1 | 4/2017 |
| EP | 3173029 A1 | 5/2017 |
| EP | 3205291 A1 | 8/2017 |
| EP | 3338703 A1 | 6/2018 |
| FR | 2828952 B1 | 12/2005 |
| JP | S5794132 A | 6/1982 |
| JP | 2001170069 A | 6/2001 |
| JP | 5301166 B2 | 9/2013 |
| JP | 2014530653 A | 11/2014 |
| JP | 2016508792 A | 3/2016 |
| JP | 2016513570 A | 5/2016 |
| JP | 2017500146 A | 1/2017 |
| JP | 2017513564 A | 6/2017 |
| JP | 2017527396 A | 9/2017 |
| JP | 6411461 B2 | 10/2018 |
| JP | 2019141659 A | 8/2019 |
| SU | 405234 A1 | 9/1975 |
| SU | 886900 A1 | 12/1981 |
| SU | 1333319 A2 | 8/1987 |
| SU | 1442191 A1 | 12/1988 |
| SU | 1459659 A1 | 2/1989 |
| WO | WO-8602254 A1 | 4/1986 |
| WO | WO-9005489 A1 | 5/1990 |
| WO | WO-9734533 A1 | 9/1997 |
| WO | WO-03094743 A1 | 11/2003 |
| WO | WO-03094746 A1 | 11/2003 |
| WO | WO-03094747 A1 | 11/2003 |
| WO | WO-2004020859 A1 | 3/2004 |
| WO | WO-2009112802 A1 | 9/2009 |
| WO | WO-2012142872 A1 | 10/2012 |
| WO | WO-2014106275 A1 | 7/2014 |
| WO | WO-2016073538 A1 | 5/2016 |
| WO | WO-2017026141 A1 | 2/2017 |
| WO | WO-2017034803 A2 | 3/2017 |
| WO | WO-2017156070 A1 | 9/2017 |
| WO | WO-2017214243 A1 | 12/2017 |

(56) References Cited

FOREIGN PATENT DOCUMENTS

| WO | WO-2018005750 A1 | 1/2018 |
|---|---|---|
| WO | WO-2018071497 A1 | 4/2018 |
| WO | WO-2018118402 A1 | 6/2018 |
| WO | WO-2019090047 A1 | 5/2019 |
| WO | WO-2020081960 A1 | 4/2020 |
| WO | WO-2020131692 A1 | 6/2020 |

OTHER PUBLICATIONS

International Search Report and Written Opinion for Application No. PCT/US2021/065308, mailed Apr. 21, 2022. 13 pages.
European Search Report (Corrected version) for Application No. EP19750317.0, mailed on Mar. 28, 2022, 26 pages.
International Search Report and Written Opinion for Application No. PCT/US2020/054568. mailed Jan. 29, 2021, 13 pages.
International Preliminary Report on Patentability for Application No. PCT/US2019/017646, mailed on Aug. 27, 2020, 10 pages.
International Preliminary Report on Patentability for Application No. PCT/US2019/019501, mailed Sep. 3, 2020, 7 pages.
International Search Report and Written Opinion for Application No. PCT/US2020/025655, mailed Jul. 22, 2020, 8 pages.
International Search Report and Written Opinion for Application No. PCT/US19/17646, mailed on Apr. 16, 2019, 11 pages.
International Search Report and Written Opinion for Application No. PCT/US2019/019501, mailed May 9, 2019, 8 pages.
International Search Report and Written Opinion for Application No. PCT/US2019/056979, mailed Dec. 18, 2019, 8 pages.
International Search Report and Written Opinion for Application No. PCT/US2019/062344, mailed Mar. 23, 2020, 17 pages.
International Search Report and Written Opinion for Application No. PCT/US2019/062768, mailed Mar. 9, 2020, 15 pages.
International Search Report and Written Opinion for Application No. PCT/US2019/064861, mailed Mar. 30, 2020, 18 pages.
International Search Report and Written Opinion for Application No. PCT/US2019/066513, mailed Apr. 21, 2020, 8 pages.
International Search Report and Written Opinion for Application No. PCT/US2019/066530, mailed Apr. 21, 2020, 8 pages.
International Search Report and Written Opinion for Application No. PCT/US2020/020672, mailed Jun. 29, 2020, 10 pages.
International Search Report and Written Opinion for Application No. PCT/US2020/033481. mailed Sep. 3, 2020, 22 pages.
International Search Report and Written Opinion for Application No. PCT/US2021/012284 mailed May 6, 2021, 23 pages.
Partial European Search Report for Application No. EP19757451.0, mailed on Feb. 2, 2022, 12 pages.
Supplementary European Search Report for Application No. EP19873128.3, mailed on Jun. 22, 2022, 7 pages.
Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.
Field Application Note—Journal Bearings, Retrieved from Wayback Machine URL: https://web.archive.org/web/20100110095051/ http://www.reliabilitydirect.com/appnotes/jb.html, on Mar. 12, 2024, 04 pages.
International Search Report and Written Opinion for Application No. PCT/US2016/059527, mailed on Feb. 16, 2017, 13 pages (ISRG07220/PCT).
Nicholson, C., et al., "Plane Bearings," ESC Report, BSA Educational Services Committee, Oct. 1994, vol. 5(1), 02 pages.
Anonymous: "Slip Joint Pliers—Wikipedia," Sep. 2017, 1 Pages. Retrieved from internet URL:https://en.wikipedia.org/w/index.php?tilte=split_joint_pliers&oldid=801407143.
Extended European Search Report for Application No. EP18823002.3 mailed on Mar. 5, 2021, 11 pages.
Extended European Search Report for Application No. EP19757451.0, mailed on May 19, 2022, 16 pages.
Extended European Search Report for Application No. EP19898247.2, mailed on Jan. 10, 2023, 12 pages.
Extended European Search Report for Application No. EP19900059.7, mailed on Dec. 5, 2022, 10 pages.
Extended European Search Report for Application No. EP20790773.4, mailed on Nov. 29, 2022, 09 pages.
Extended European Search Report for Application No. EP20815112.6, mailed on Jan. 5, 2023, 11 pages.
Extended European Search Report for Application No. EP20875978.7, mailed on Jan. 31, 2024, 26 pages.
Extended European Search Report for Application No. EP24155564.8, mailed on Jul. 8, 2024, 12 pages.
International Search Report and Written Opinion for Application No. PCT/US2018/039912, mailed on Oct. 12, 2018, 15 pages (ISRG08630/PCT).

* cited by examiner

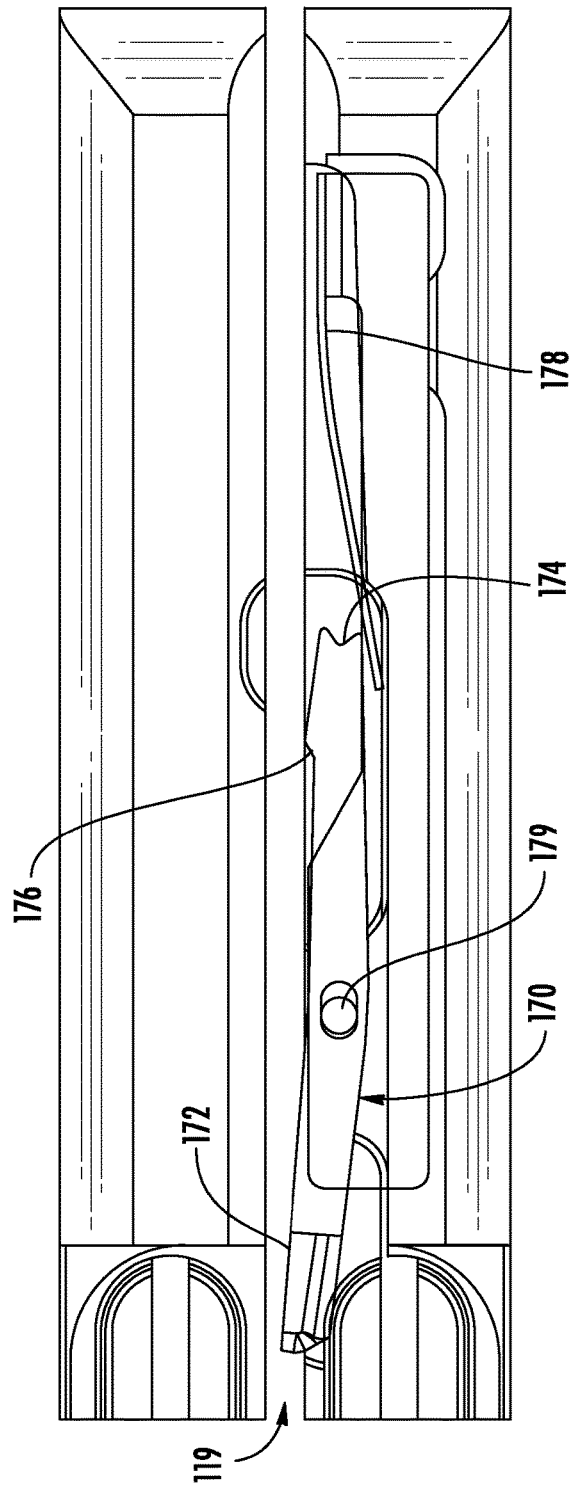
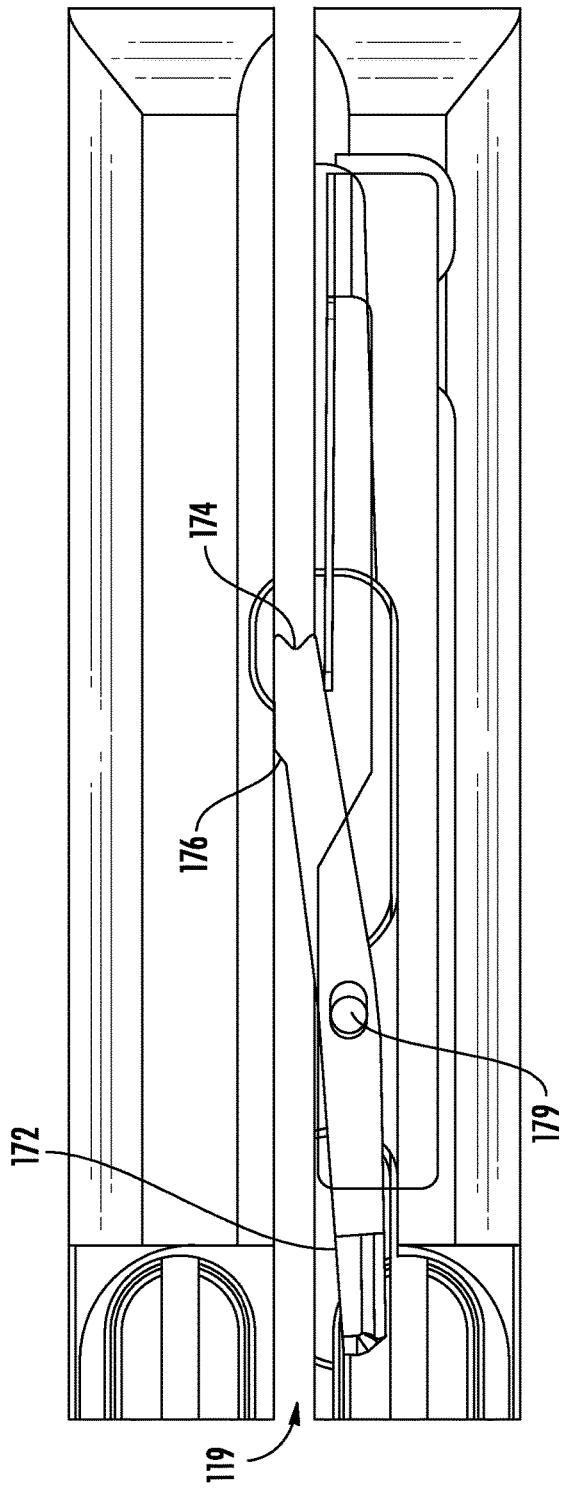

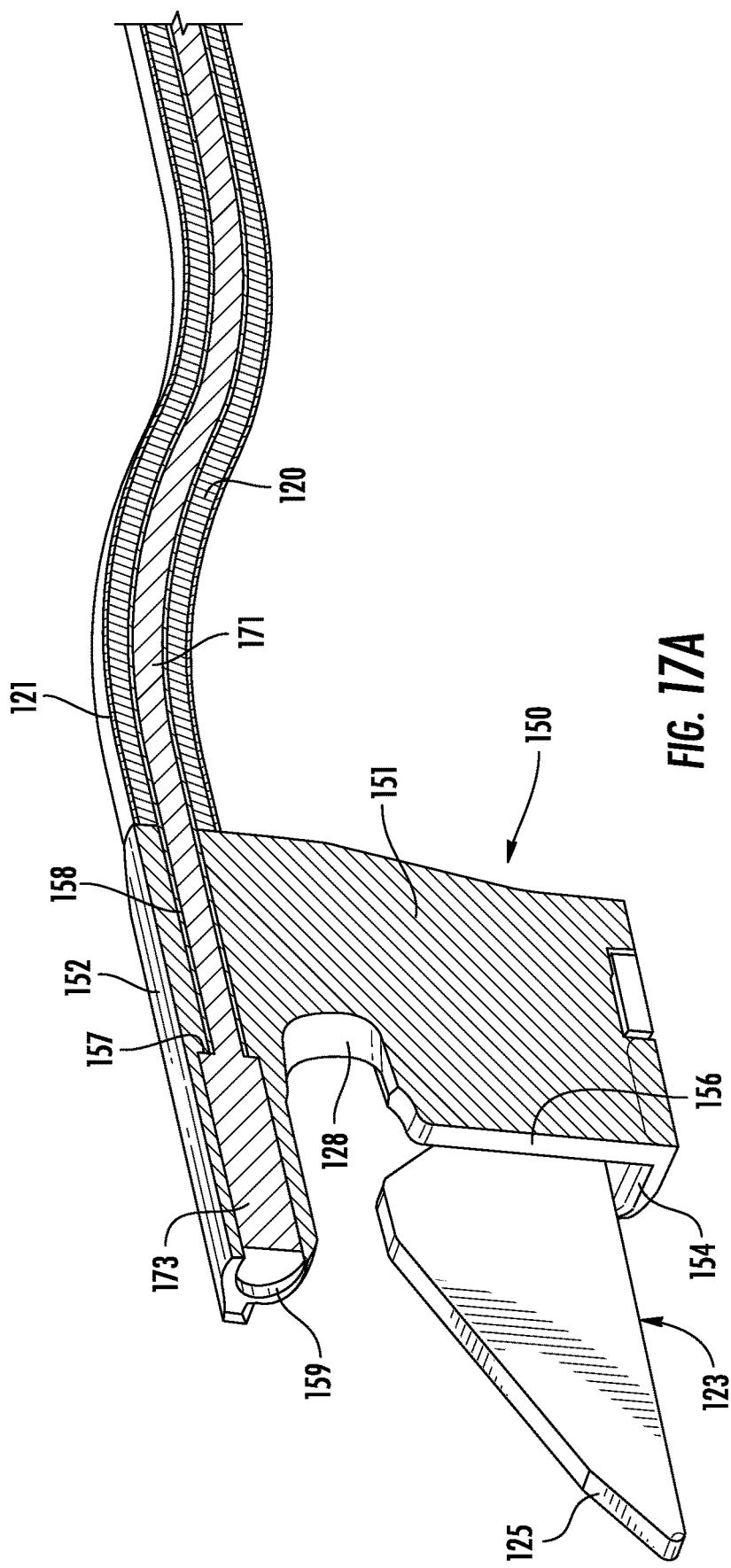

SURGICAL INSTRUMENTS WITH SWITCHES FOR DEACTIVATING AND/OR IDENTIFYING STAPLER CARTRIDGES

CROSS-REFERENCE TO RELATED APPLICATIONS

This application is a continuation of U.S. application Ser. No. 17/414,805, filed on Jun. 16, 2021, which is the National Stage of International Application No. PCT/US2019/066513 filed Dec. 16, 2019, which claims the benefit of U.S. Provisional Application No. 62/783,429, filed Dec. 21, 2018, the entire disclosure of each are incorporated herein by reference for all purposes.

BACKGROUND

The field of the present disclosure relates to medical instruments, and more particularly to tissue sealing instruments for use in surgeries. Even more particularly, the present disclosure relates to a surgical stapling instrument having a novel switch-activated lockout mechanism to prevent firing of a surgical stapling instrument while a spent stapler cartridge remains in place on the jaw. The present disclosure further relates to a surgical stapling instrument configured for use with a surgical system having a control unit configured to identify the type and size of a reload installed in the surgical stapling instrument.

Minimally invasive medical techniques are intended to reduce the amount of extraneous tissue that is damaged during diagnostic or surgical procedures, thereby reducing patient recovery time, discomfort, and deleterious side effects. One effect of minimally invasive surgery, for example, is reduced post-operative hospital recovery times. The average hospital stay for a standard open surgery is typically significantly longer than the average stay for an analogous minimally invasive surgery (MIS). Thus, increased use of MIS could save millions of dollars in hospital costs each year. While many of the surgeries performed each year in the United States could potentially be performed in a minimally invasive manner, only a portion of the current surgeries uses these advantageous techniques due to limitations in minimally invasive surgical instruments and the additional surgical training involved in mastering them.

Improved surgical instruments such as tissue access, navigation, dissection and sealing instruments have enabled MIS to redefine the field of surgery. These instruments allow surgeries and diagnostic procedures to be performed with reduced trauma to the patient. A common form of minimally invasive surgery is endoscopy, and a common form of endoscopy is laparoscopy, which is minimally invasive inspection and surgery inside the abdominal cavity. In standard laparoscopic surgery, a patient's abdomen is insufflated with gas, and cannula sleeves are passed through small (approximately one-half inch or less) incisions to provide entry ports for laparoscopic instruments.

Laparoscopic surgical instruments generally include an endoscope (e.g., laparoscope) for viewing the surgical field and tools for working at the surgical site. The working tools are typically similar to those used in conventional (open) surgery, except that the working end or end effector of each tool is separated from its handle by an extension tube (also known as, e.g., an instrument shaft or a main shaft). The end effector can include, for example, a clamp, grasper, scissor, stapler, cautery tool, linear cutter, or needle holder.

To perform surgical procedures, the surgeon passes working tools through cannula sleeves to an internal surgical site and manipulates them from outside the abdomen. The surgeon views the procedure from a monitor that displays an image of the surgical site taken from the endoscope. Similar endoscopic techniques are employed in, for example, arthroscopy, retroperitoneoscopy, pelviscopy, nephroscopy, cystoscopy, cisternoscopy, sinoscopy, hysteroscopy, urethroscopy, and the like.

Minimally invasive telesurgical robotic systems are being developed to increase a surgeon's dexterity when working on an internal surgical site, as well as to allow a surgeon to operate on a patient from a remote location (outside the sterile field). In a telesurgery system, the surgeon is often provided with an image of the surgical site at a control console. While viewing a three dimensional image of the surgical site on a suitable viewer or display, the surgeon performs the surgical procedures on the patient by manipulating master input or control devices of the control console, which in turn control motion of the servo-mechanically operated slave instruments.

The servomechanism used for telesurgery will often accept input from two master controllers (one for each of the surgeon's hands) and may include two or more robotic arms. A surgical instrument is mounted on each of the robotic arms. Operative communication between master controllers and associated robotic arm and instrument assemblies is typically achieved through a control system. The control system typically includes at least one processor that relays input commands from the master controllers to the associated robotic arm and instrument assemblies and back in the case of, for example, force feedback or the like. One example of a robotic surgical system is the DA VINCI™ system commercialized by Intuitive Surgical, Inc. of Sunnyvale, California.

A variety of structural arrangements have been used to support the surgical instrument at the surgical site during robotic surgery. The driven linkage or "slave" is often called a robotic surgical manipulator, and exemplary linkage arrangements for use as a robotic surgical manipulator during minimally invasive robotic surgery are described in U.S. Pat. Nos. 7,594,912, 6,758,843, 6,246,200, and 5,800,423, the full disclosures of which are incorporated herein by reference in their entirety for all purposes. These linkages often manipulate an instrument holder to which an instrument having a shaft is mounted. Such a manipulator structure can include a parallelogram linkage portion that generates motion of the instrument holder that is limited to rotation about a pitch axis that intersects a remote center of manipulation located along the length of the instrument shaft. Such a manipulator structure can also include a yaw joint that generates motion of the instrument holder that is limited to rotation about a yaw axis that is perpendicular to the pitch axis and that also intersects the remote center of manipulation. By aligning the remote center of manipulation with the incision point to the internal surgical site (for example, with a trocar or cannula at an abdominal wall during laparoscopic surgery), an end effector of the surgical instrument can be positioned safely by moving the proximal end of the shaft using the manipulator linkage without imposing potentially hazardous forces against the abdominal wall. Alternative manipulator structures are described, for example, in U.S. Pat. Nos. 6,702,805, 6,676,669, 5,855,583, 5,808,665, 5,445,166, and 5,184,601, the full disclosures of which are incorporated herein by reference in their entirety for all purposes.

During the surgical procedure, the telesurgical system can provide mechanical actuation and control of a variety of surgical instruments or tools having end effectors that perform various functions for the surgeon, for example, holding or driving a needle, grasping a blood vessel, dissecting tissue, or the like, in response to manipulation of the master input devices. Manipulation and control of these end effectors is a particularly beneficial aspect of robotic surgical systems. For this reason, it is desirable to provide surgical tools that include mechanisms that provide two or three degrees of rotational movement of an end effector to mimic the natural action of a surgeon's wrist. Such mechanisms should be appropriately sized for use in a minimally invasive procedure and relatively simple in design to reduce possible points of failure. In addition, such mechanisms should provide an adequate range of motion to allow the end effector to be manipulated in a wide variety of positions.

Surgical instruments are often deployed into restrictive body cavities (e.g., through a cannula to inside the pelvis). Accordingly, it is desirable for the surgical instrument to be both compact and maneuverable for best access to and visibility of the surgical site. Known surgical instruments, however, may fail to be both compact and maneuverable. For example, known surgical instruments may lack maneuverability with respect to multiple degrees of freedom (e.g., roll, pitch, and yaw) and associated desired ranges of motion.

Surgical clamping and cutting instruments (e.g., non-robotic linear clamping, stapling, and cutting devices, also known as surgical staplers; and electrosurgical vessel sealing devices) have been employed in many different surgical procedures. For example, a surgical stapler can be used to resect a cancerous or anomalous tissue from a gastrointestinal tract. Many known surgical clamping and cutting devices, including known surgical staplers, have opposing jaws that clamp tissue and an articulated knife to cut the clamped tissue.

Many surgical clamping and cutting instruments include an instrument shaft supporting an end effector to which a replaceable stapler cartridge is mounted. An actuation mechanism articulates the stapler cartridge to deploy staples from the stapler cartridge to staple tissue clamped between the stapler cartridge and an articulable jaw of the end effector. Different types of stapler cartridges can be used that have different staple lengths suitable for different tissues to be stapled.

The use of replaceable stapler cartridges does, however, give rise to some additional issues. For example, prior to use, a suitable stapler cartridge having the correct staple length should be mounted to the end effector. If a stapler cartridge having an unsuitable staple length is mistakenly mounted to the end effector, the tissue may be stapled with the unsuitable length staples if the error is not detected and corrected prior to stapling of the tissue. As another example, if a previously used stapler cartridge is not replaced with a new stapler cartridge, the tissue clamped between the previously used stapler cartridge and the articulable jaw cannot be stapled due to the lack of staples to deploy. A similar problem can arise if no stapler cartridge is mounted to the end effector. The danger of firing a surgical stapling instrument while a spent stapler cartridge remains in place on the jaw has given rise to the development of various lockout mechanisms. However, incorporating lockout features typically increases the diameter of the end effector, increasing overall instrument size and making a given instrument less ideal for minimally invasive surgery.

Accordingly, while the new telesurgical systems and devices have proven highly effective and advantageous, still further improvements would be desirable. In general, it would be desirable to have a relatively compact mechanism in place to prevent firing of a surgical stapling instrument while a spent stapler cartridge remains in place on the jaw. Additionally, it would be desirable to have a mechanism allowing a robotic surgical system to detect the type of stapler cartridge or reload that has been installed. Thus, a need exists for a reload detection mechanism that can detect: whether a stapler cartridge is mounted to the surgical instrument; whether the mounted stapler cartridge is unfired (i.e., fresh) or has already been fired; and the type of the mounted stapler cartridge mounted to the end effector to ensure that the mounted stapler cartridge has a suitable staple length for the tissue to be stapled.

SUMMARY

The following presents a simplified summary of the claimed subject matter in order to provide a basic understanding of some aspects of the claimed subject matter. This summary is not an extensive overview of the claimed subject matter. It is intended to neither identify key or critical elements of the claimed subject matter nor delineate the scope of the claimed subject matter. Its sole purpose is to present some concepts of the claimed subject matter in a simplified form as a prelude to the more detailed description that is presented later.

The present disclosure relates to surgical stapling instruments that have devices or mechanisms for identifying and/or deactivating disposable stapler cartridges for use with the stapling instruments. The stapling instrument includes a drive member for actuating a staple cartridge and a locking member movable from a disabled position permitting distal translation of the drive member through a staple firing stroke, to a locking position inhibiting distal translation of the drive member through the staple firing stroke. The staple cartridge may include a switch for maintaining the locking member in the disabled position. The switch may be further configured to operate as a reload detection mechanism for determining the type of reload present in the surgical stapling instrument. In one embodiment, a surgical stapling instrument includes an end effector defining a longitudinal axis including a first jaw and a second jaw. The first jaw includes an anvil and, the second jaw is configured to receive a stapler cartridge having one or more staples. The surgical stapling instrument further includes a drive member configured to translate distally and an actuation mechanism configured to translate the drive member distally through the end effector. The surgical stapling instrument further includes a locking member movable from a disabled position permitting distal translation of the drive member to at least an axial position wherein the drive member engages at least one of the staples, to a locking position inhibiting distal translation of the drive member to said axial position. In the locking position, the locking member functions to deactivate the stapler cartridge by preventing firing of a surgical stapling instrument while a spent stapler cartridge remains in place on the jaw. This ensures that a surgeon will not attempt to clamp or seal tissue with a staple cartridge that has already been deployed and thus is unable to drive staples into the tissue.

In embodiments, the locking member is maintained in the disabled position by a portion of the stapler cartridge. In embodiments, the portion of the stapler cartridge that maintains the locking member in the disabled position is a switch movably coupled to the stapler cartridge. In embodiments, the locking member moves in a first direction, and the switch is movable in a second direction different from the first direction. This is advantageous because it allows for maintenance of reduced instrument diameter, as the switch and the locking member will not be contained in the same space within the surgical instrument once actuation has occurred.

In embodiments, the locking member includes a distal portion configured to contact the switch, and a distal drive member-engaging portion.

In embodiments, the drive member includes one or more inclined distal surfaces or ramps. In embodiments, upon distal advancement of the drive member, the inclined distal surface(s) of the drive member engage the switch and moves the switch from a first portion to a second position. In the first position, the switch maintains the locking member in the disabled position, permitting the drive member to translate distally through the end effector. As the inclined distal surfaces of the drive member contact the switch, they move the switch into the second position, wherein the switch no longer engages the locking member. The locking member, which is preferably biased towards the locking position, will then automatically move into the locking position.

The switch is preferably retained in the second position once it has been moved into this position. Thus, the stapler cartridge can only be used once. As soon as the drive member actuates the staples and moves the switch into the second position, the locking member moves into the locking position and remains in this position so that the drive member can no longer translate distally to actuate the stapler cartridge.

In embodiments, the switch includes a cutout of a predetermined height configured to be engaged by the inclined distal surface of the drive member. In embodiments, engagement of the inclined distal surface of the drive member with the cutout creates a detectable resistance readable by a control unit of a surgical system to detect a given reload size or type.

In embodiments, the switch includes a stationary portion and a movable portion, the stationary portion configured to be separated from the movable portion by shearing along an axis upon contact by the drive member. In embodiments, the engagement between an inclined distal surface of the drive member with the switch creates a detectable resistance, the detectable resistance readable by a control unit of a surgical system to detect a given reload size or type.

In embodiments, the locking member pivots between the disabled position and the locking position. In embodiments, the locking member pivots about a pivot point that is laterally offset from the longitudinal axis of the end effector. In embodiments, the locking member pivots in a direction substantially perpendicular to the longitudinal axis defined by the end effector.

In embodiments, the drive member includes a first portion that translates through a channel in the first jaw. In embodiments, the actuation mechanism includes a coil that applies a distal force to the first portion of the drive member.

In embodiments, the surgical stapling instrument further includes an elongated shaft, the end effector mounted on a distal end portion of the elongated shaft.

In embodiments, the surgical stapling instrument further includes an articulation mechanism configured to articulate the end effector relative to the elongate shaft. In embodiments, the surgical stapling instrument further includes an actuator operatively connected to the actuation mechanism. In embodiments, the actuator includes a movable handle of a handle assembly provided at a proximal end portion of the surgical instrument. In embodiments, the actuator includes a control device of a robotic surgical system. In embodiments, the drive member includes a knife configured to cut tissue grasped between the first and second jaw.

In another aspect, the present disclosure relates to a surgical stapling instrument including an end effector defining a longitudinal axis including a first jaw and a second jaw, the first jaw including an anvil. The surgical stapling instrument further includes a stapler cartridge having one or more staples and a switch. The second jaw is configured to receive the stapler cartridge. The surgical stapling instrument further includes a drive member configured to translate distally and an actuation mechanism configured to translate the drive member distally through the end effector. The drive member is configured to contact the switch of the stapler cartridge at an axial position of the drive member relative to the end effector. The switch is configured to provide a detectable resistance upon engagement of the drive member at said axial position. This detectable resistance is advantageous because it may provide information for a reload detection mechanism that can detect: whether a stapler cartridge is mounted to the surgical instrument; whether the mounted stapler cartridge is unfired (or fresh) or has already been fired; and the type of the mounted stapler cartridge mounted to the end effector to ensure that the mounted stapler cartridge has a suitable staple length for the tissue to be stapled.

In embodiments, the surgical stapling instrument further includes a lockout assembly including a locking member movable in a first direction from a disabled position permitting distal translation of the drive member through a staple firing stroke, to a locking position inhibiting distal translation of the drive member through the staple firing stroke. the surgical stapling instrument further includes a switch movable in a second direction different from the first direction, from a first position and second position, wherein when the switch is in the first position the switch maintains the locking member in the disabled position, and wherein when the switch is in the second position the switch disengages from the locking member.

In embodiments, the drive member includes one or more inclined distal ramps and the switch has a contact portion configured to contact the one or more distal ramps upon distal translation of the drive member through the end effector. In embodiments, the contact portion of the switch is disposed at a predetermined height such that the inclined distal ramp of the drive member is located at the axial position upon contact with the contact portion.

In certain embodiments, the surgical instrument includes two or more staple cartridges. Each of the staple cartridges includes a switch having a contact portion configured to contact the one or more distal ramps of the drive member. Each of the contact portions of the switches is located at a different height relative to the end effector (and the drive member). Since the distal ramp(s) of the drive member are inclined, the drive member will contact each of the switches of the different staple cartridges at different axial positions of the drive member relative to the staple cartridge. This contact is detectable by a control unit or other suitable mechanism such that each of the staple cartridges may be identified by the control unit.

In embodiments, the surgical instrument is operatively coupled to a control unit, the control unit configured to process the detectable resistance to identify a type of reload present in the surgical stapling instrument.

In certain embodiments, the switch is configured to provide the detectable resistance to the control until upon engagement of the drive member with the contact portion of the switch. I In other embodiments, the switch includes a detachable portion configured to detach from the remainder of the switch upon contact with the drive member. In these embodiments, the control untit detects resistance upon detachment of the detachable portion, thereby identifying the stapler cartridge. In an exemplary embodiment, the switch include a stationary portion and a movable portion, the stationary portion being configured to be separated from the movable portion by shearing along an axis upon contact by the drive member.

In another aspect, the present disclosure relates to a surgical stapling instrument including an end effector defining a longitudinal axis including a first jaw and a second jaw. The first jaw includes an anvil and, the second jaw is configured to receive a stapler cartridge having one or more staples. The surgical stapling instrument further includes a drive member configured to translate distally and an actuation mechanism configured to translate the drive member distally through the end effector. The surgical stapling instrument further includes a lockout assembly including a locking member movable in a first direction from a disabled position permitting distal translation of the drive member through a staple firing stroke, to a locking position inhibiting distal translation of the drive member through the staple firing stroke. The drive member is configured to contact a switch at an axial position of the drive member relative to the end effector, and wherein the switch is configured to provide a detectable resistance upon engagement of the drive member at said axial position.

In embodiments, the locking member is maintained in the disabled position by a portion of the stapler cartridge. In embodiments, the portion of the stapler cartridge that maintains the locking member in the disabled position comprises the switch. In embodiments, the locking member moves in a first direction, and the switch is movable in a second direction different from the first direction.

In embodiments, the drive member includes one or more inclined distal ramps and the switch has a contact portion configured to contact the one or more distal ramps upon distal translation of the drive member through the end effector. In embodiments, the contact portion of the switch is disposed at a predetermined height such that the inclined distal ramp of the drive member is located at the axial position upon contact with the contact portion.

In embodiments, the surgical instrument is operatively coupled to a surgical system including a control unit, the control unit configured to process the detectable resistance to identify a type of reload present in the surgical stapling instrument.

In embodiments, the switch includes a stationary portion and a movable portion. The stationary portion is configured to be separated from the movable portion by shearing along an axis upon contact by the drive member.

In embodiments, the surgical instrument is operatively coupled to a surgical system including a control unit. The control unit is configured to process the detectable resistance to identify a type of reload present in the surgical stapling instrument.

In yet another aspect, the present disclosure relates to a surgical stapling instrument including an end effector defining a longitudinal axis including a first jaw and a second jaw. The first jaw includes an anvil and, the second jaw is configured to receive a stapler cartridge having one or more staples. The surgical stapling instrument further includes a drive member configured to translate distally and an actuation mechanism configured to translate the drive member distally through the end effector. The surgical stapling instrument further includes a lockout assembly including a locking member movable in a first direction from a disabled position permitting distal translation of the drive member through a staple firing stroke, to a locking position inhibiting distal translation of the drive member through the staple firing stroke. The drive member is configured to contact a first switch at an axial position of the drive member relative to the end effector, and a second switch, and wherein the first switch is configured to provide a detectable resistance upon engagement of the drive member at said axial position. This is advantageous because the detectable resistance provided upon engagement of the drive member with the first switch for reload detection may occur at a more proximal position within the surgical instrument, such as a proximal tail portion of the cartridge.

In embodiments, the locking member is maintained in the disabled position by a portion of the stapler cartridge. In embodiments, the portion of the stapler cartridge that maintains the locking member in the disabled position comprises the second switch. In embodiments, the locking member moves in a first direction, and the first switch and second switch are both movable in a second direction different from the first direction.

In embodiments, the drive member includes one or more inclined distal ramps and the first switch and second switch have contact portions configured to contact the one or more distal ramps upon distal translation of the drive member through the end effector. In embodiments, the contact portion of the first switch is disposed at a predetermined height such that the inclined distal ramp of the drive member is located at the axial position upon contact with the contact portion.

In embodiments, the first switch is formed on a proximal tail portion of the stapler cartridge.

In embodiments, the surgical instrument is operatively coupled to a surgical system including a control unit. The control unit is configured to process the detectable resistance to identify a type of reload present in the surgical stapling instrument.

BRIEF DESCRIPTION OF THE DRAWINGS

The above and other aspects, features, and advantages of the present surgical instruments having a locking mechanism will become more apparent in light of the following detailed description when taken in conjunction with the accompanying drawings in which:

FIG. 6 depicts a top view of a locking member in accordance with the embodiment of FIG. 5 in the unlocked position;

FIG. 6A depicts a top view of a locking member in accordance with the embodiment of FIG. 5 in the locked position;

FIG. 17A is a cross-sectional perspective view of the actuation mechanism for a drive member in accordance with the surgical instrument of FIG. 1;

DETAILED DESCRIPTION

Particular embodiments of the present surgical instruments are described hereinbelow with reference to the accompanying drawings; however, it is to be understood that the disclosed embodiments are merely exemplary of the disclosure and may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure. Well-known functions or constructions are not described in detail to avoid obscuring the present disclosure in any unnecessary detail.

While the following disclosure is presented with respect to a linear surgical stapler where staples are sequentially fired, it should be understood that the features of the presently described surgical instruments may be readily adapted for use in any type of surgical clamping, cutting, or sealing instruments. The surgical clamping and cutting instrument may be a minimally invasive (e.g., laparoscopic) instrument or an instrument used for open surgery.

Additionally, the features of the presently described surgical stapling instruments may be readily adapted for use in surgical instruments that are activated using any technique within the purview of those skilled in the art, such as, for example, manually activated surgical instruments, powered surgical instruments (e.g., electro-mechanically powered instruments), robotic surgical instruments, and the like.

Figure 1:
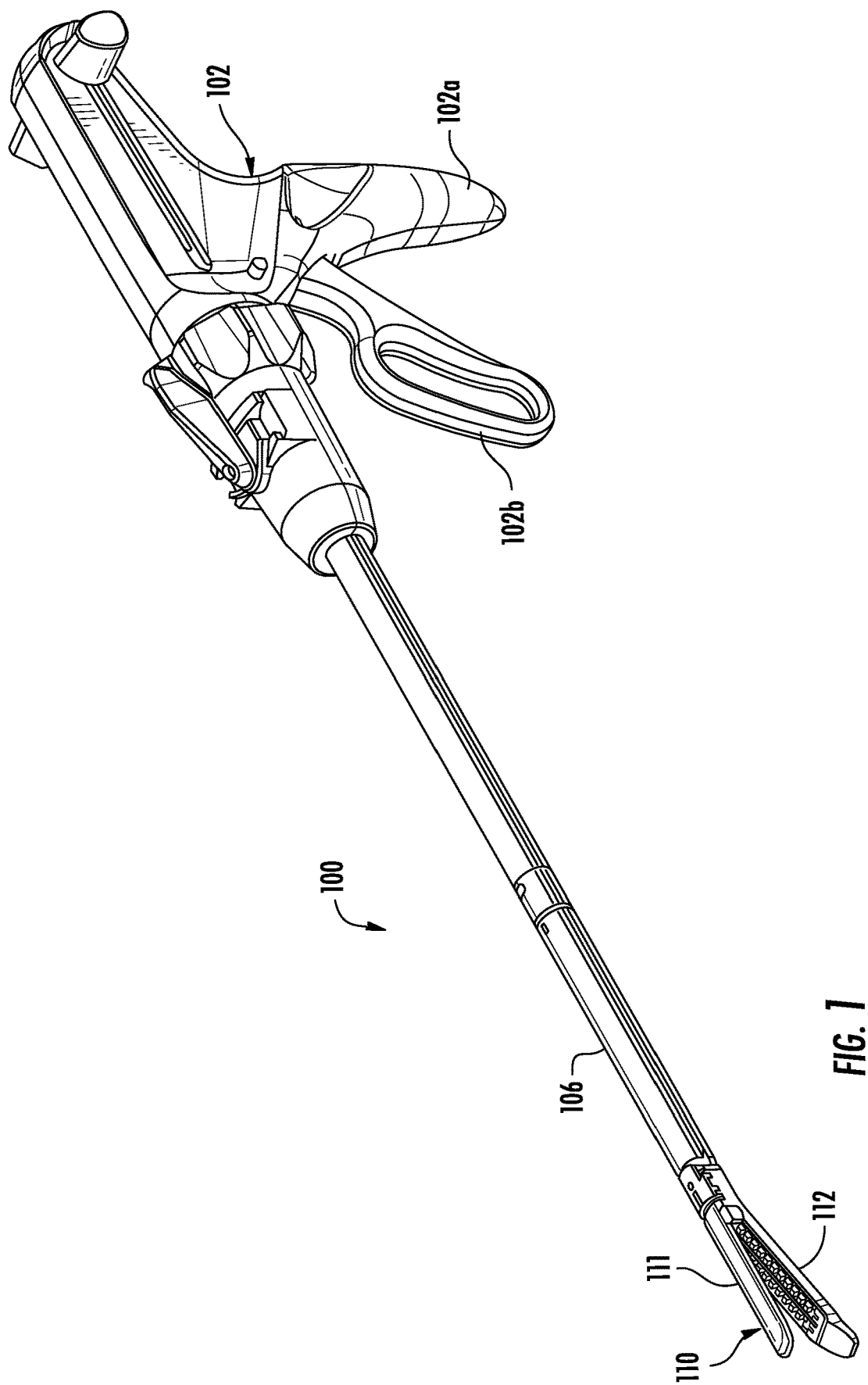
FIG. 1 is a perspective view of an illustrative surgical instrument having an end effector mounted to an elongated shaft, and an actuation mechanism.

FIG. 1 is a perspective view of an illustrative surgical instrument 100 in accordance with embodiments of the present disclosure having a handle assembly 102, and an end effector 110 mounted on an elongated shaft 106. End effector 110 includes a stationary jaw 111 and a moveable jaw 112. Handle assembly 102 includes a stationary handle 102a and a moveable handle 102b which serves as an actuator for surgical instrument 100.

In certain embodiments, handle assembly 102 may include input couplers (not shown) instead of, or in addition to, the stationary and movable handles. The input couplers provide a mechanical coupling between the drive tendons or cables of the instrument and motorized axes of the mechanical interface of a drive system. The input couplers may interface with, and be driven by, corresponding output couplers (not shown) of a telesurgical surgery system, such as the system disclosed in U.S Pub. No. 2014/0183244A1, the entire disclosure of which is incorporated by reference herein. The input couplers are drivingly coupled with one or more input members (not shown) that are disposed within the instrument shaft 106. The input members are drivingly coupled with the end effector 110. Suitable input couplers can be adapted to mate with various types of motor packs (not shown), such as the stapler-specific motor packs disclosed in U.S. Pat. No. 8,912,746, or the universal motor packs disclosed in U.S. Pat. No. 8,529,582, the disclosures of both of which are incorporated by reference herein in their entirety. Further details of known input couplers and surgical systems are described, for example, in U.S. Pat. Nos. 8,597,280, 7,048,745, and 10,016,244. Each of these patents is hereby incorporated by reference in its entirety.

Actuation mechanisms of surgical instrument 100 may employ drive cables that are used in conjunction with a system of motors and pulleys. Powered surgical systems, including robotic surgical systems that utilize drive cables connected to a system of motors and pulleys for various functions including opening and closing of jaws, as well as for movement and actuation of end effectors are well known. Further details of known drive cable surgical systems are described, for example, in U.S. Pat. Nos. 7,666,191 and 9,050,119 both of which are hereby incorporated by reference in their entireties. While described herein with respect to an instrument configured for use with a robotic surgical system, it should be understood that the wrist assemblies described herein may be incorporated into manually actuated instruments, electro-mechanical powered instruments, or instruments actuated in any other way.

Figure 2:
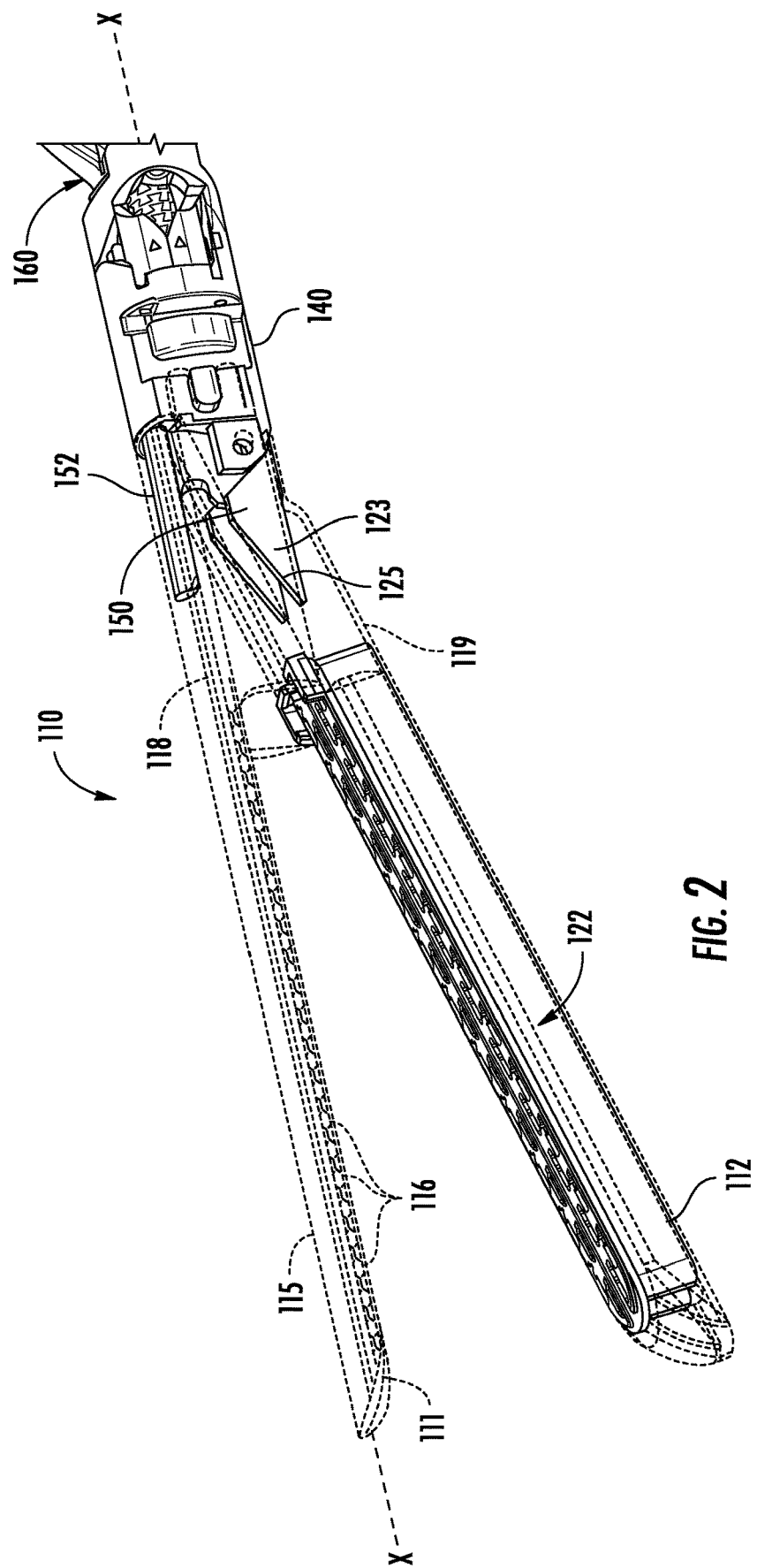
FIG. 2 is a perspective view of the distal end portion of an illustrative surgical instrument in accordance with the present disclosure with the jaws in the open position.

FIG. 2 shows the distal end portion of surgical instrument 100, including an end effector 110 defining a longitudinal axis X-X and having a first jaw 111, a second jaw 112, a clevis 140 for mounting jaws 111, 112 to the instrument). In certain embodiments, second jaw 112 is a movable jaw configured to move from an open position to a closed position relative to first jaw 111. In other embodiments, first jaw 111 is a movable jaw configured to move between open and closed positions relative to second jaw 112. In still other embodiments, both jaws 111, 112 are movable relative to each other.

First jaw 111 includes an anvil 115 having staple-forming pockets 116. Second jaw 112 is configured to move from an open position to a closed position relative to stationary jaw 111. In the open position, a fresh stapler cartridge 122 such as the exemplary one shown in FIG. 3 (sometimes referred to as a reload) can be loaded into movable jaw 112 and tissue may be positioned between the jaws 111, 112. In the closed position, jaws 111, 112 cooperate to clamp tissue such that cartridge 122 and the anvil 115 are in close cooperative alignment.

Figure 3:
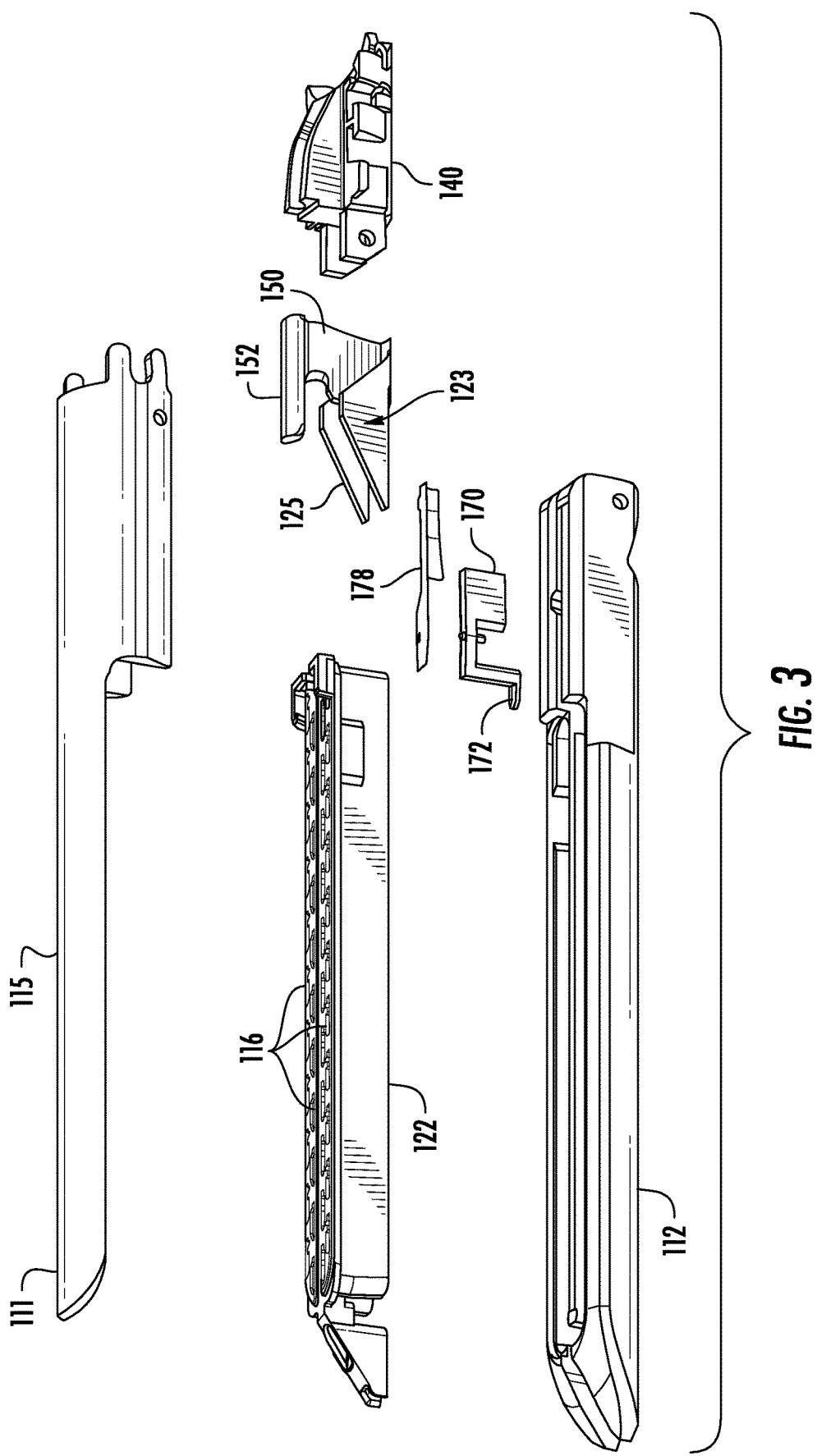
FIG. 3 is an exploded view of the end effector of FIG. 2.
Figure 4:
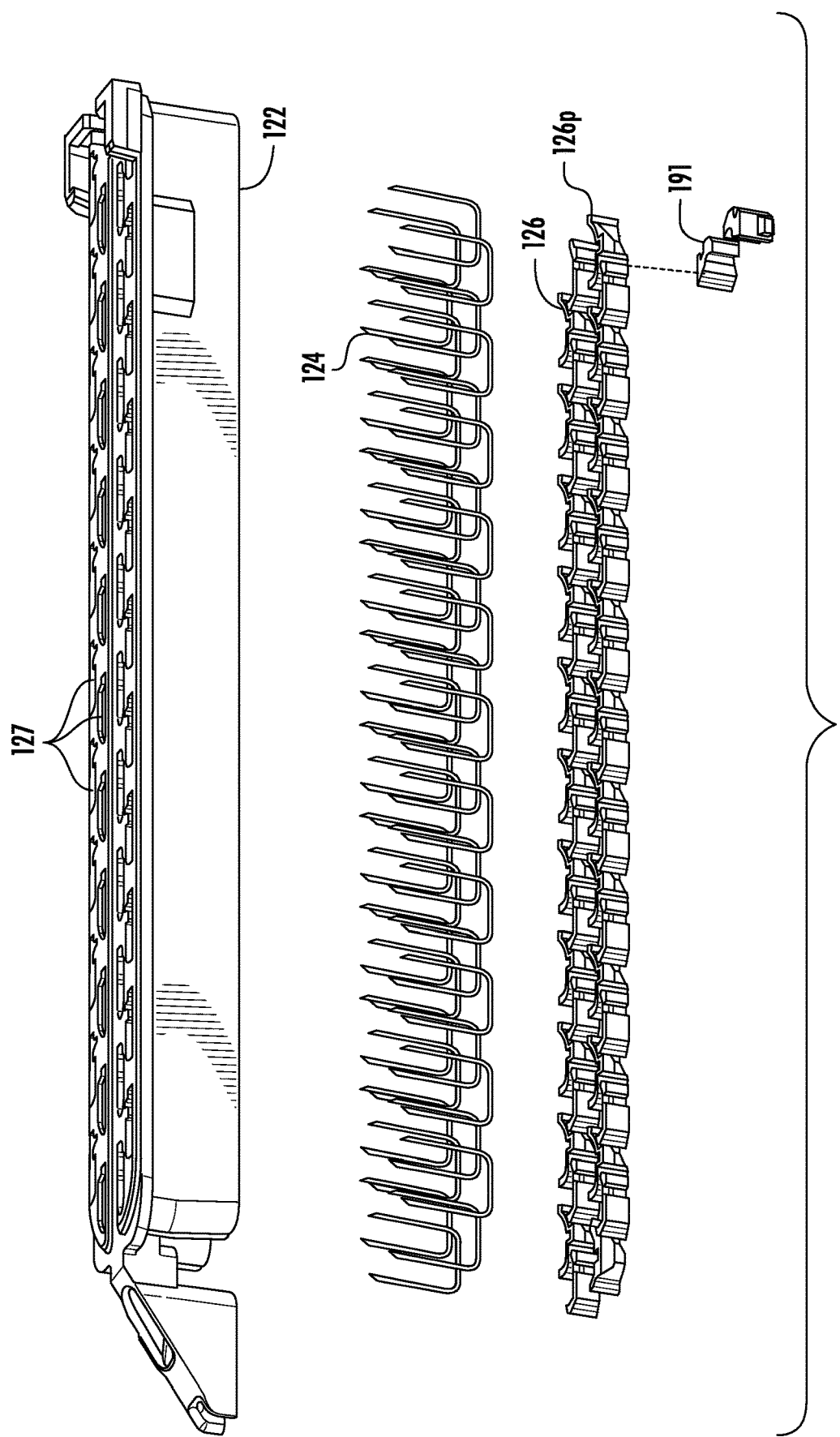
FIG. 4 is an exploded view of the cartridge, surgical fasteners, staple drivers, and switches which form part of the cartridge assembly of FIG. 3.

As shown in FIG. 4, stapler cartridge 122 may include a plurality of staples 124 supported on corresponding staple drivers 126 provided within respective staple retention openings 127 formed in stapler cartridge 122. In embodiments, a shuttle 123 (see FIG. 3) having an inclined distal portion 125 sequentially acts on staple drivers 126 upon distal movement of the drive member 150, camming staple drivers 126 upwardly, thereby moving staples 124 into deforming contact with anvil 115. In embodiments, shuttle 123 may be included within stapler cartridge 122. In embodiments, inclined distal portions 125 may be integrated with drive member 150 as seen in FIG. 3. In embodiments, stapler cartridge 122 further includes one or more switches 191 positioned on the proximal side of the proximal-most pusher 126p within stapler cartridge 122. The functionality of switches 191 will be described in more detail below.

As shown in FIGS. 3 and 4, end effector 110 may also include a lockout assembly including locking member 170, switch 191, and spring 178. Locking member 170 includes a distal, switch-contacting portion 172 and a proximal engagement portion 174 (See FIG. 5). End effector 110 may also include a drive member 150 configured to translate distally and retract proximally through the end effector and includes an integrated shuttle 123 having an inclined distal portion 125 formed thereon. As seen in FIG. 2, upper shoe 152 of drive member 150 is substantially aligned with and translates through a channel 118 in fixed jaw 111, while lower shoe 154 (see FIG. 16) of drive member 150 is substantially aligned with and translates through a channel 119 and below jaw 112. The details of the drive member and actuation will be described below.

Figure 5:
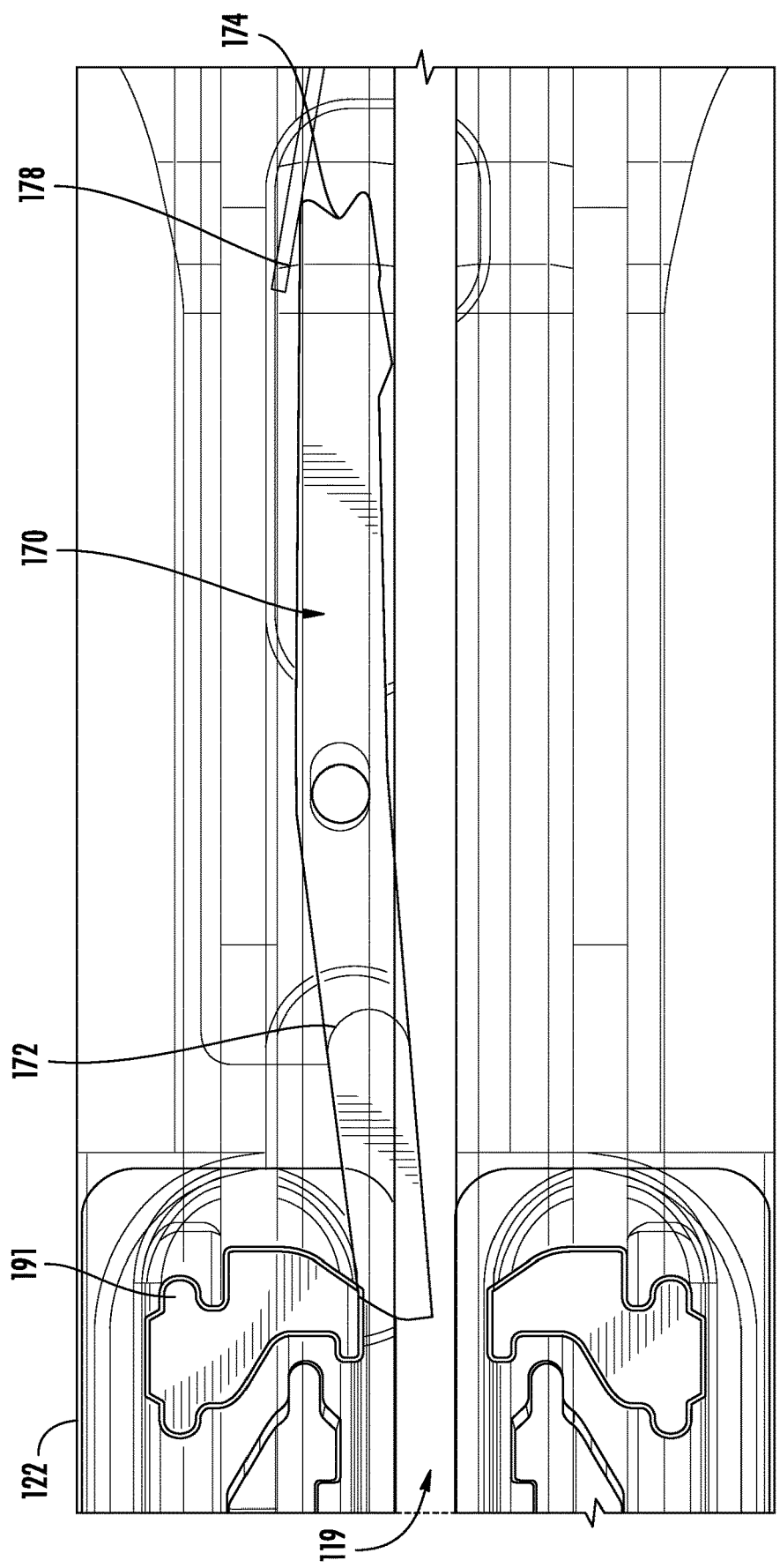
FIG. 5 depicts a partial cross-sectional side view of the end effector of a surgical stapling instrument including a lockout assembly in accordance with an embodiment of the present disclosure having an unfired stapler cartridge installed.

FIG. 5 shows a portion of an illustrative surgical instrument with an unfired reload installed, including stapler cartridge 122, spring 178, locking member 170, and switch 191 When an unfired stapler cartridge is installed, as shown in FIG. 5, switch 191 is in a first unraised position. In a fresh, unfired stapler cartridge, switch 191 is in contact with distal portion 172 of locking member 170, keeping distal portion 172 held within channel 119 and proximal engagement portion 174 outside of channel 119. When locking member 170 is in this disabled position, distal translation of drive member 150 is permitted, as locking member 170 will not obstruct movement of drive member 150 because engagement portion 174 is held out of alignment with channel 119.

FIGS. 6 and 6A show a top view of locking member 170 in the unlocked or disabled position and the locked position, respectively.

Locking member 170 pivots about a pivot point 179, that is laterally offset from channel 119, and is configured to move in a lateral direction, preferably substantially perpendicular to, the longitudinal axis of the end effector. Spring 178 biases engagement portion 174 of locking member 170 into channel 119 to lock the instrument. In the unlocked position of FIGS. 5 and 6, switch 191 engages distal portion 172 of locking member 170, overcoming the bias of spring 178 and holding engagement portion 174 out of channel 119, permitting distal movement of drive member 150. When switch 191 is no longer in contact with distal portion 172 of locking member 170, spring 178 forces engagement portion 174 of locking member into channel 119, where it obstructs distal movement of drive member 150, as best seen in FIG. 6A.

Figure 7A:
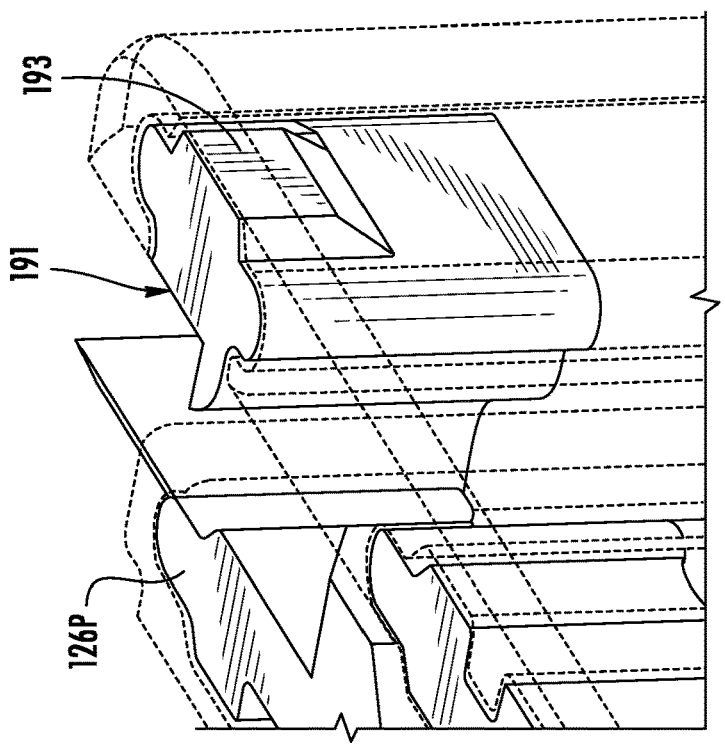
FIG. 7A depicts a perspective view of a switch in accordance with the embodiment of FIG. 5.
Figure 7:
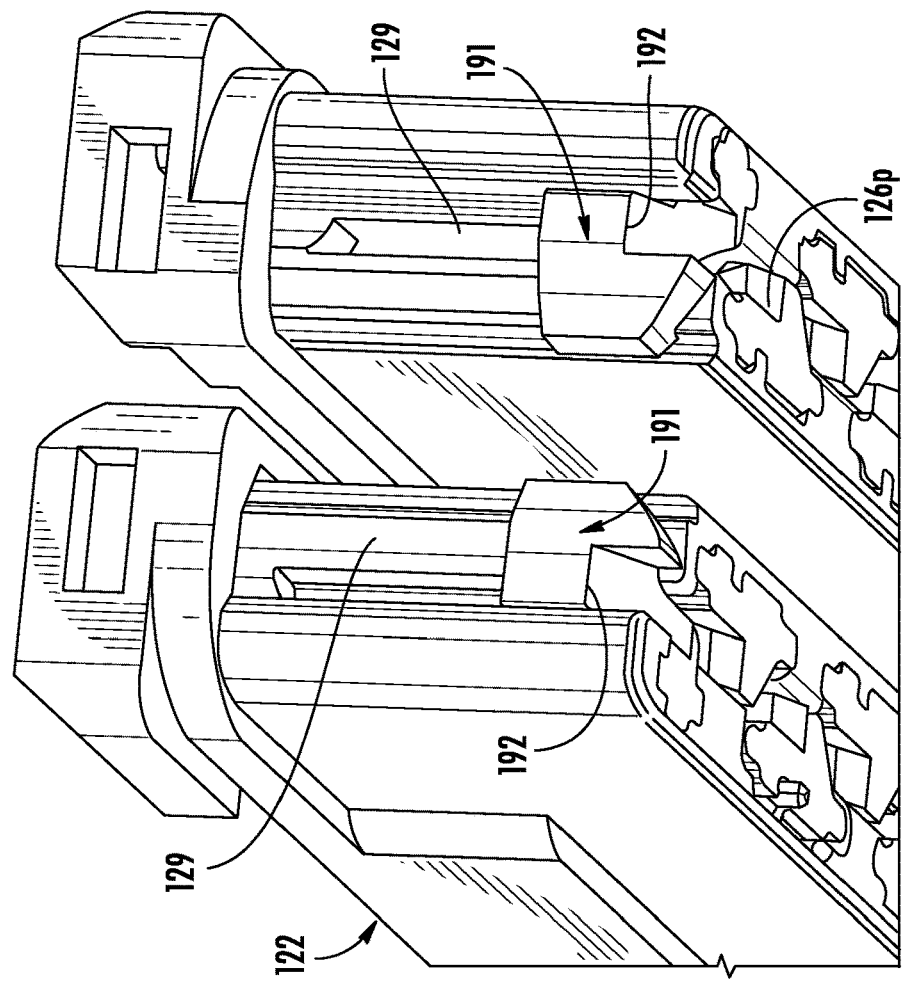
FIG. 7 depicts a perspective view of the proximal end of a stapler cartridge in accordance with the embodiment of FIG. 5 having a lockout assembly including a switch for enabling and disabling the locking member.

FIGS. 7 and 7A show an unfired stapler cartridge with switch 191 in the initial, pre-firing position. Switch 191 may be contained in stapler cartridge 122, and may be substantially aligned with staple drivers 126 on a desired side of the stapler cartridge where it may engage distal portion 172 of locking member 170 (see FIG. 8). Switch 191 includes a cutout 196 (see FIG. 13A) configured to be engaged by inclined distal portion 125 of shuttle 123 upon distal advancement of drive member 150 when the surgical instrument 100 is actuated. In an unfired stapler cartridge, as shown in FIG. 7, switch 191 is in an initial pre-firing position, where it rests on the bottom of a switch channel 129 within stapler cartridge 122. Switch channel 129 extends upwardly towards anvil 115. As shown in FIG. 7A, switch 191 further includes detent 193. Detent 193 is configured to provide mechanical resistance that must be overcome by drive member 150 in order to slide switch 191 from the initial position toward anvil 115. This ensures that the lockout will not unintentionally activate as may happen if switch 191 freely slides in channel 129 (e.g., in the absence of detent 193).

Figure 8:
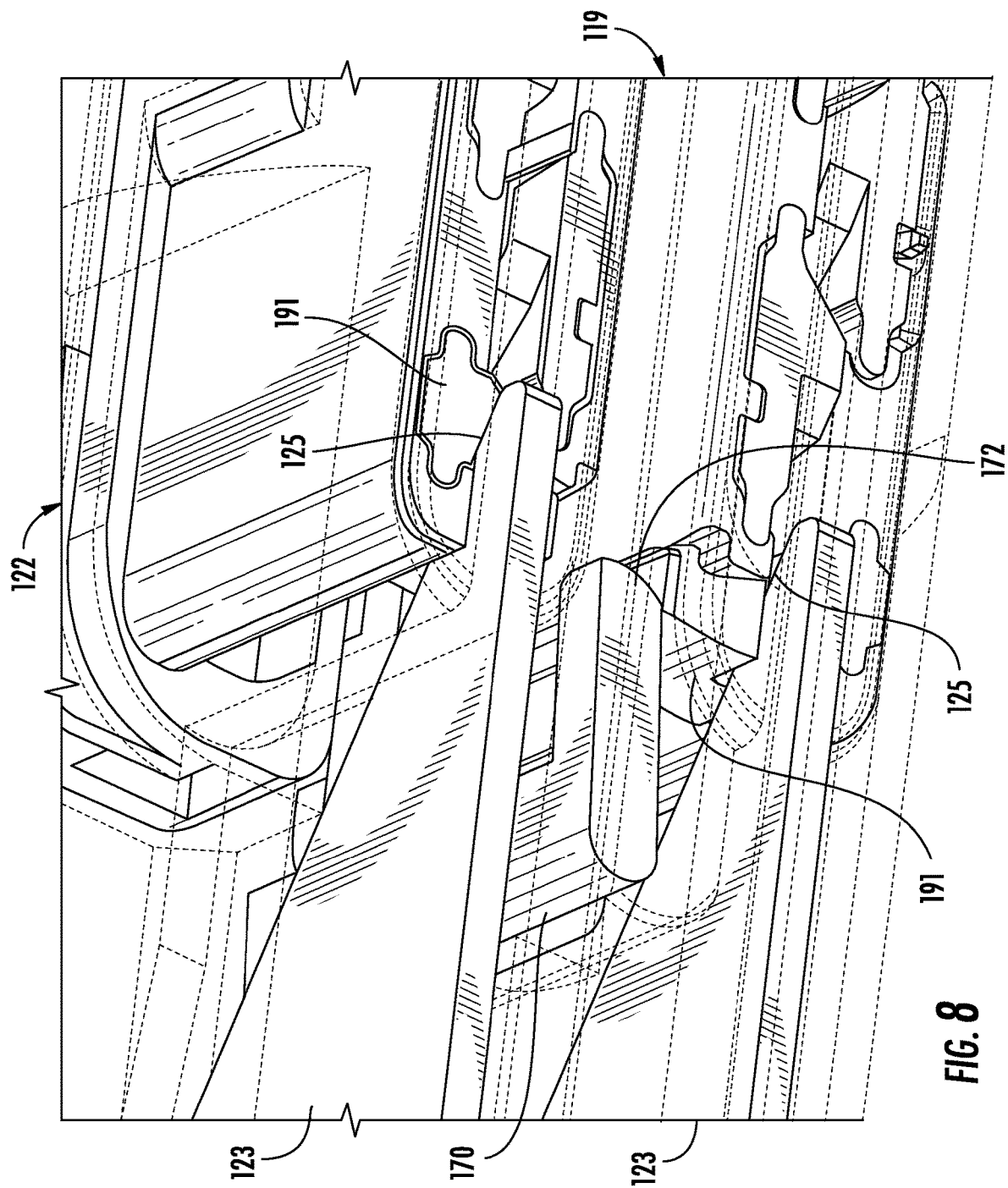
FIG. 8 is a partial perspective view of the end effector including a lockout assembly in accordance with the embodiment of FIG. 5 showing a wedge of the drive member contacting a switch.

FIG. 8 depicts inclined distal portions 125 of drive member 150 interfacing with switch 191 to disable locking member 170. Distal portion 172 of locking member 170 is shown protruding into channel 119, as switch 191 is blocking it from being laterally displaced.

FIGS. 9-12 depict sequential cross-sectional views (with locking member 170 not shown) of a portion of an illustrative surgical instrument throughout distal translation of drive member 150 during actuation. Inclined distal portions 125 of drive member 150 are shown interfacing with switch 191 to move it from the unraised position, to the raised position in which locking member 170 becomes enabled.

Figure 9:
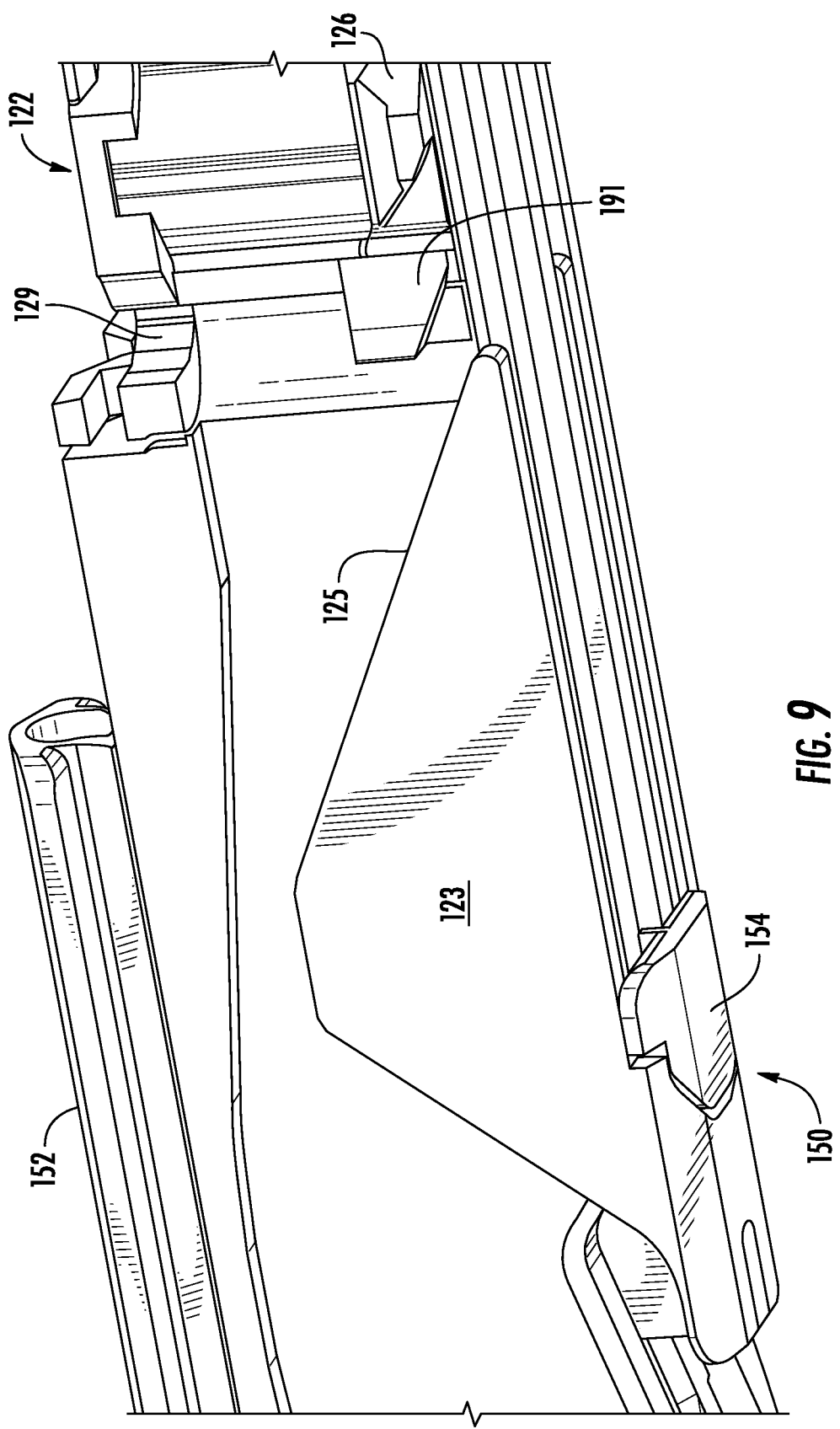
FIG. 9 is a partial perspective view of an end effector in accordance with the embodiment of FIG. 5 showing a drive member moving distally towards a switch.
Figure 10:
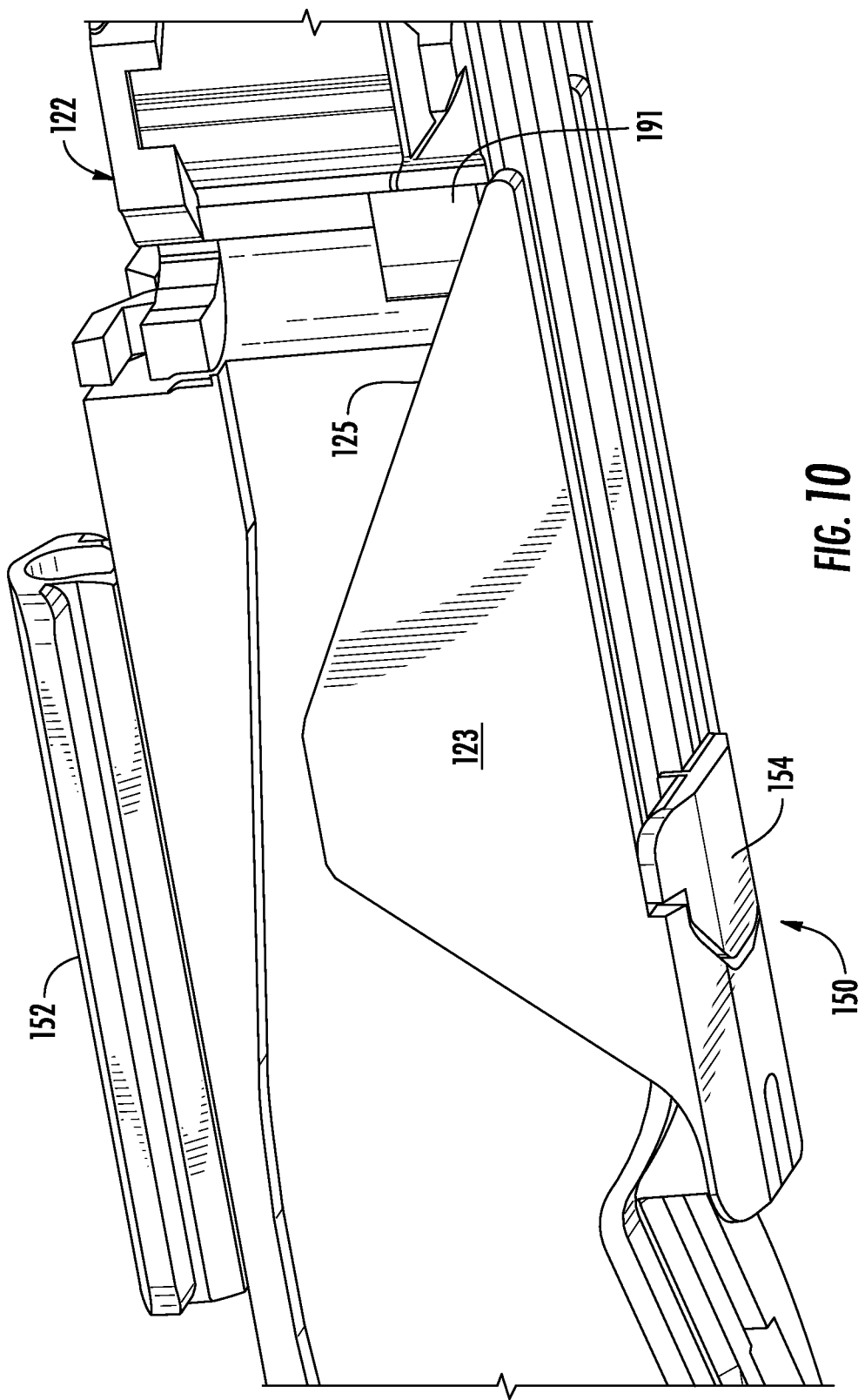
FIG. 10 is a partial perspective view of an end effector in accordance with the embodiment of FIG. 5 showing a drive member contacting a switch upon translating distally.
Figure 11:
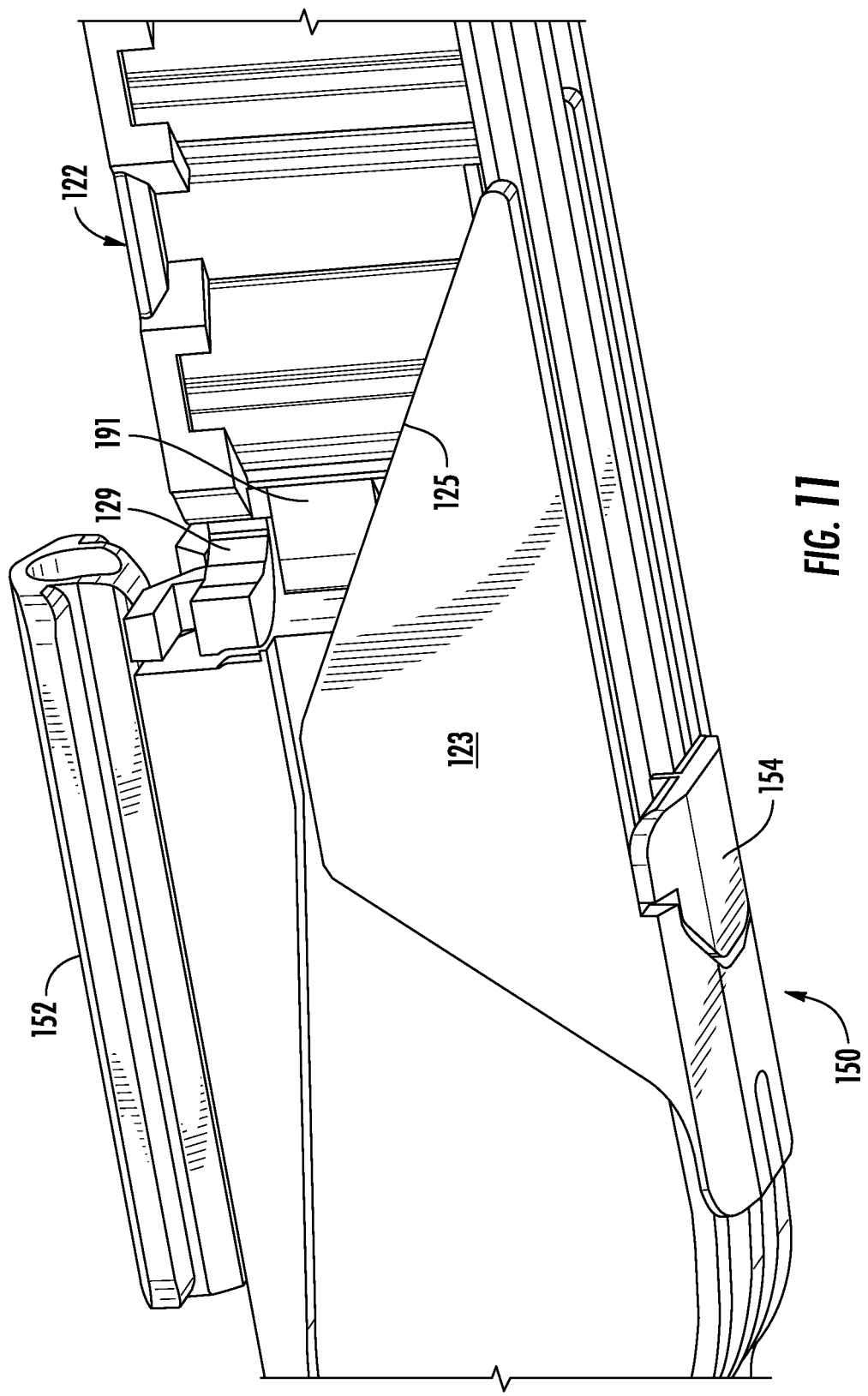
FIG. 11 is a partial perspective view of an end effector in accordance with the embodiment of FIG. 5 showing a wedge of the drive member engaging and pushing a switch upwards during actuation.

In FIG. 9, drive member 150 begins to translate distally along the longitudinal axis of the end effector and has not yet contacted switch 191. In FIG. 10, inclined distal portion 125 of drive member 150 contacts switch 191. As seen in FIG. 11, inclined distal portion 125 of drive member 150 then begins to force switch 191 upwards within switch channel 129 of stapler cartridge 122 as drive member 150 continues to translate distally. Switch 191 travels in a direction substantially perpendicular to the longitudinal axis of the end effector. In embodiments, switch 191 travels vertically, while locking member 170 travels laterally, allowing for maintenance of a reduced instrument diameter, as they will not compete for the same space within the instrument after actuation has occurred.

Figure 12:
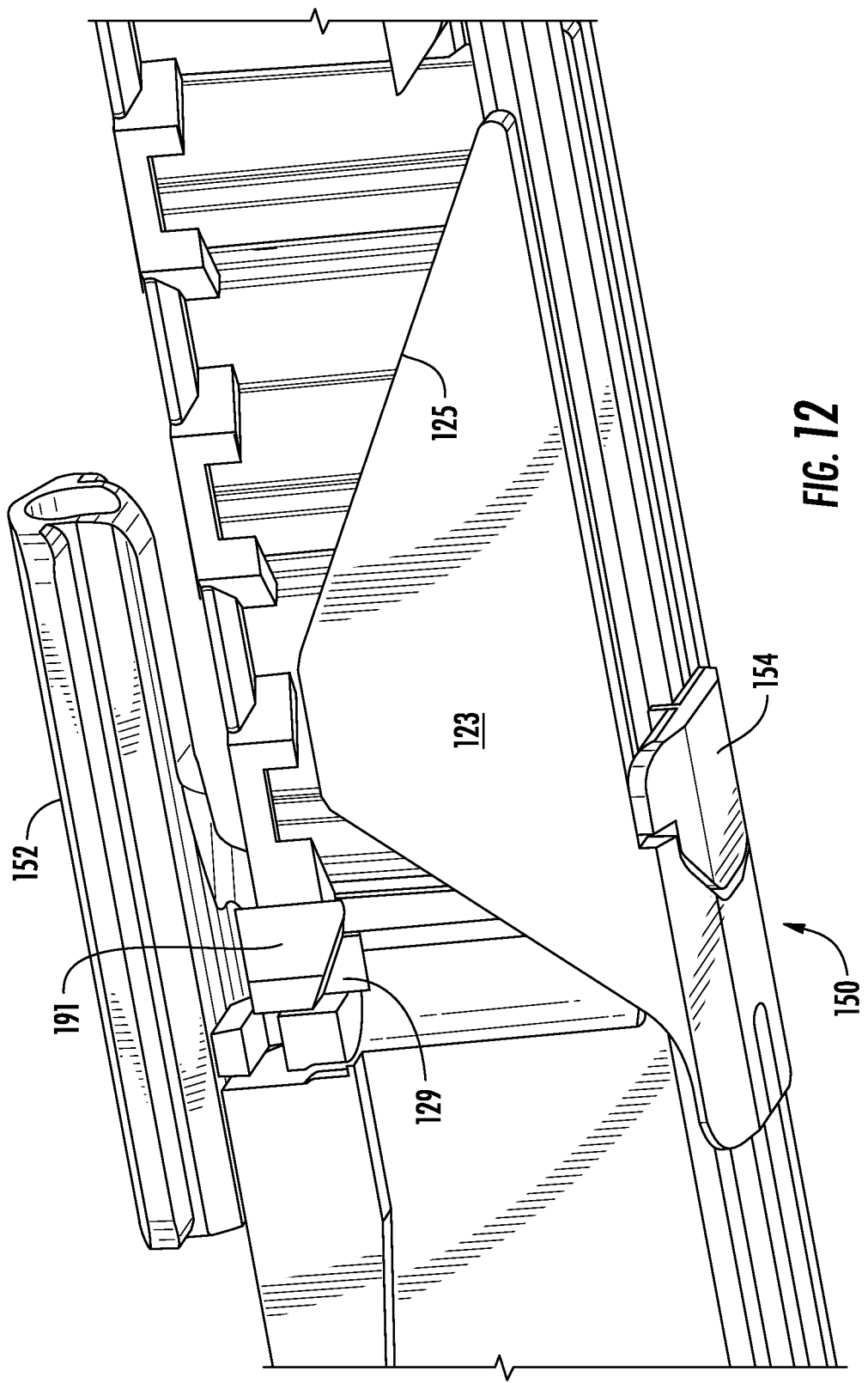
FIG. 12 is a partial perspective view of an end effector in accordance with the embodiment of FIG. 5 showing a switch pushed completely upwards into a raised position, and the drive member translating distally underneath the switch.

As seen in FIG. 12, drive member 150 continues to travel distally and forces switch 191 into a fully raised position within channel 129, allowing the entirety of drive member 150 to pass by switch 191 such that it may complete the firing stroke. Switch 191 is fitted into channel 129 such that it may not return to the unraised position once the drive member has traveled distally. As drive member 150 displaces switch 191, distal portion 172 of locking member 170 is prevented from lateral movement by contact with drive member 150.

Figure 13:
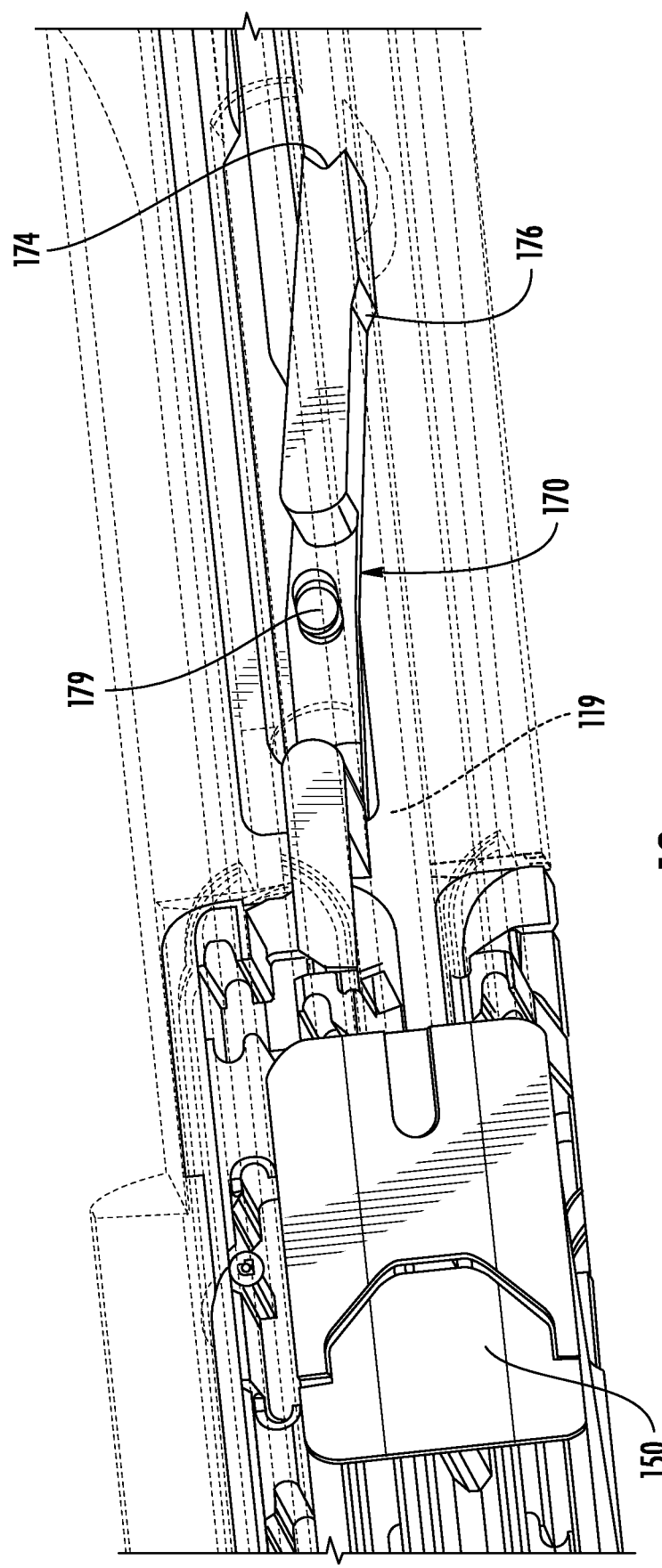
FIG. 13 is a top view of an end effector in accordance with the embodiment of FIG. 5 showing a drive member translated distally, a switch in the raised position, and a locking member that is enabled.
Figure 13A:
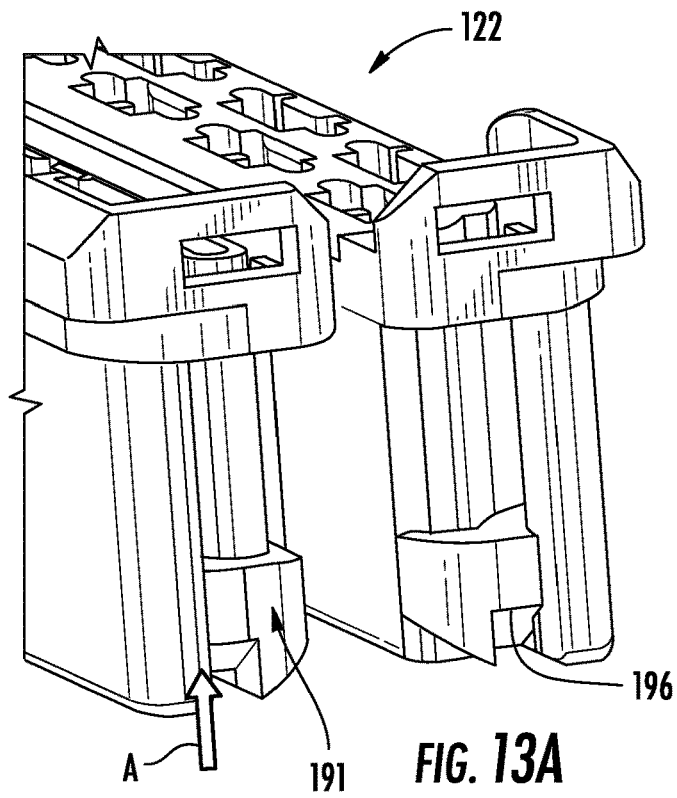
FIGS. 13A-13D are perspective views of the proximal ends of a series of stapler cartridges, each stapler cartridge containing a unique switch for reload detection.
Figure 13B:
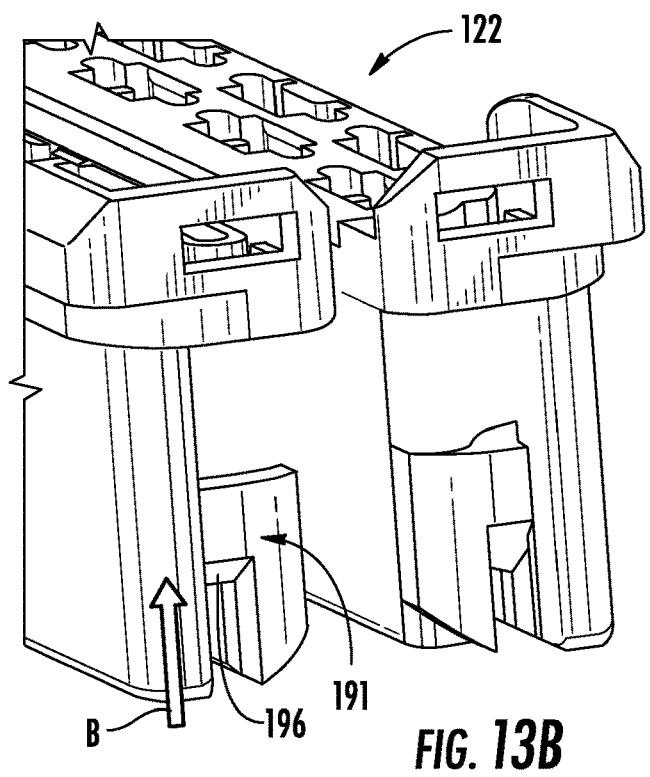
Figure 13C:
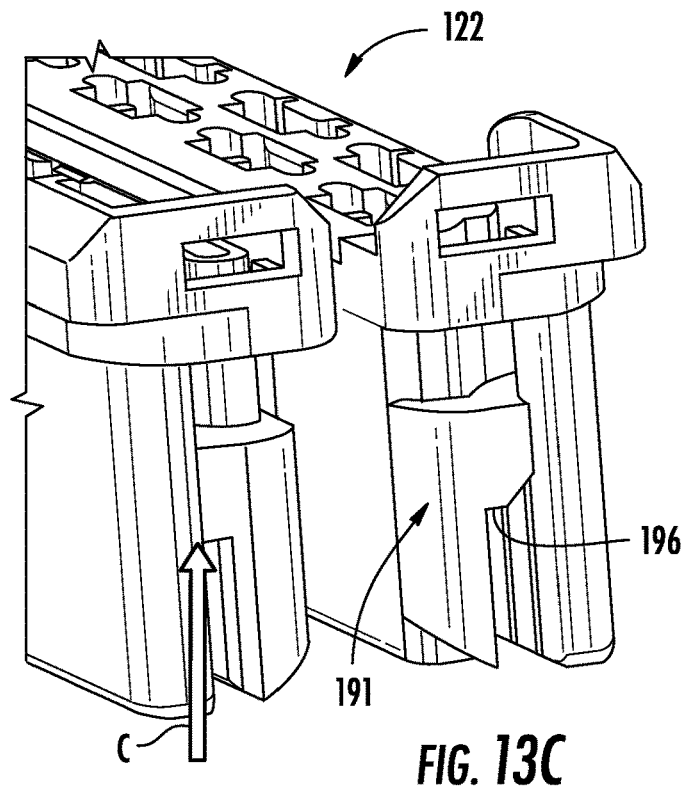
Figure 13D:
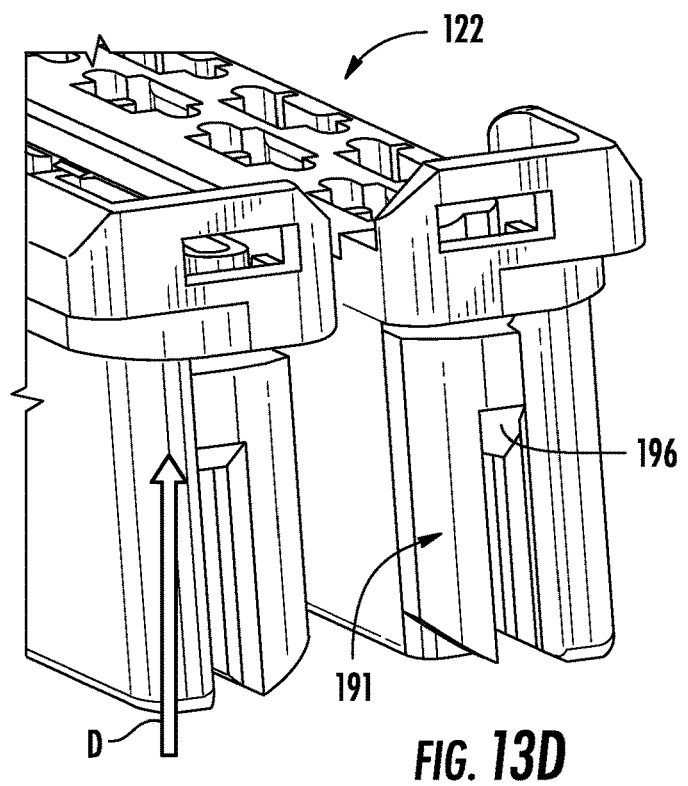

FIG. 13 depicts a top view of an illustrative surgical instrument during actuation. In FIG. 13, drive member 150 has translated past switch 191 and moved it into the fully raised position, enabling locking member 170. In this configuration, drive member 150 may continue to travel distally to drive staples into the tissue grasped between jaws 111, 112 and cut the stapled tissue. Upon retraction, a proximal surface on the proximal end of drive member 150 engages a proximal ramped surface 176 on locking member 170, allowing drive member 150 to return to a position proximal of locking member 170. However, once drive member 150 is positioned proximally of locking member 170, if another attempt is made to actuate the instrument, drive member 150 will be obstructed by engagement portion 174 of locking member 150, preventing actuation of an unloaded instrument.

In another aspect of the present disclosure, the particular type of stapler cartridge (or reload) installed in the end effector may be detected based on the configuration of the switches 191. Specifically, different stapler cartridges 122 may have switches 191 including a cutout 196 of a given height depending on the type of reload present within stapler cartridge 122. FIGS. 13A-13D depict four different stapler cartridges 122 having switches 191 each including a cutout 196 of a given height depicted by arrows A-D respectively. As the length of cutout 196 increases, the distance that shuttle 123 must travel, as described above, before engaging switch 191 increases. Thus, as the length of cutout 196 increases, the contact point between inclined distal portion 125 and switch 191 moves upwards and towards the proximal end of inclined distal portion 125. When the drive member 150 engages switch 191, it creates a detectable resistance and urges switch 191 upwards towards a raised position as drive member 150 travels distally.

In embodiments, a control unit of a robotic surgical system may be configured to detect the axial position along a firing stroke at which the shuttle 123 engages a given switch 191 via detection of a detectable resistance, such as a torque spike, allowing the system to determine the type of reload presently installed. Varying the length of the cutout formed on a given switch will adjust the axial position at which the drive member engages the switch to create the detectable resistance. Based on the detected resistance, a control unit, operatively coupled with the actuation mechanism, determines the correct amount of forces to apply to the drive member depending upon the features of the detected stapler cartridge, including but not limited to, the number of staples contained therein, the size of the staples contained therein, and the geometry of the staples contained therein. An exemplary surgical stapler including a control unit of a surgical system that is operatively coupled to the actuation mechanism is described for example in International Application No. PCT/JS2017050747, the disclosure of which is hereby incorporated by reference in its entirety.

Figure 14:
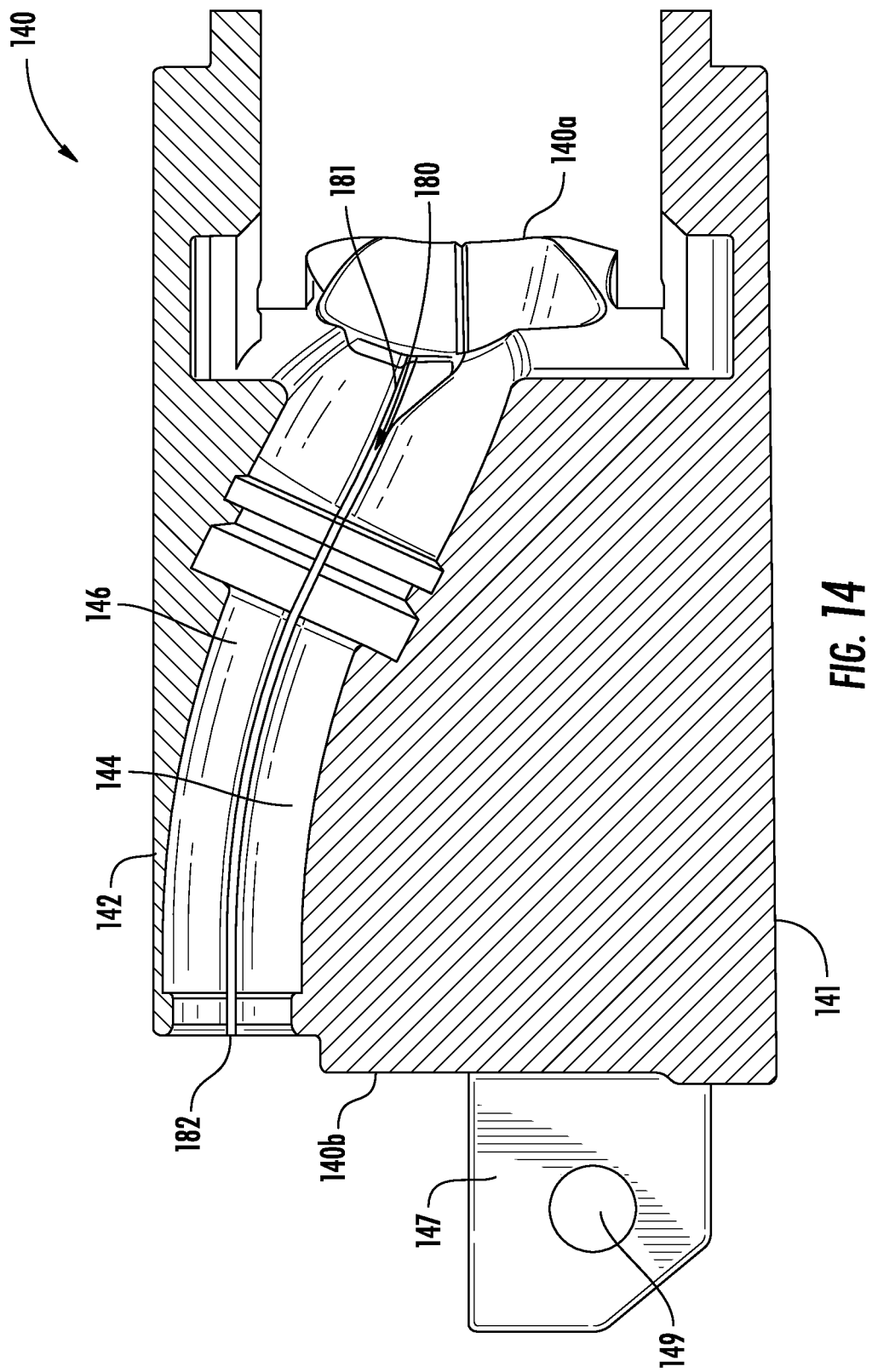
FIG. 14 is a cross-sectional side of a two-part clevis of the surgical instrument of FIG. 1.

Jaws 111, 112 are attached to surgical instrument 100 via clevis 140. See, FIG. 14. Clevis 140 includes a proximal surface 140a and a distal surface 140b. Clevis 140 further includes upper clevis portion 142 and lower clevis portion 141 that cooperate when assembled to form protrusion 145 (best seen in FIG. 18A) configured to engage tabs 113 (best seen in in FIG. 18A of jaw 111 to securely mount jaw 111 in a fixed position on instrument 100. As seen in FIG. 14, lower clevis portion 141 includes a pair of distally extending arms 147 for supporting movable jaw 112. Arms 147 include opening 149 for receiving a pivot pin 130 defining a pivot axis around which jaw 112 pivots as described in more detail below. Lower clevis portion 141 also includes ramped groove 144 configured to guide a portion of an actuation coil 120 emerging from wrist 160. Upper clevis portion 142 includes a complementary shaped ramped groove 146 that cooperates with ramped groove 144 of lower clevis portion 141 to form an enclosed channel 180 that guides coil 120 as it jogs upwards from wrist 160 towards distal surface 157 of upper shoe 152 of drive member 150. In embodiments, channel 180 may include a first end 181 at a central portion of proximal surface 140a and a second end 182 at a peripheral portion of distal surface 140b. In embodiments, enclosed channel 180 may be substantially "S" shaped. Although shown as a two-part clevis, it should be understood that the clevis may be a unitary structure formed, for example, by molding, machining, 3-D printing, or the like.

Figure 15:
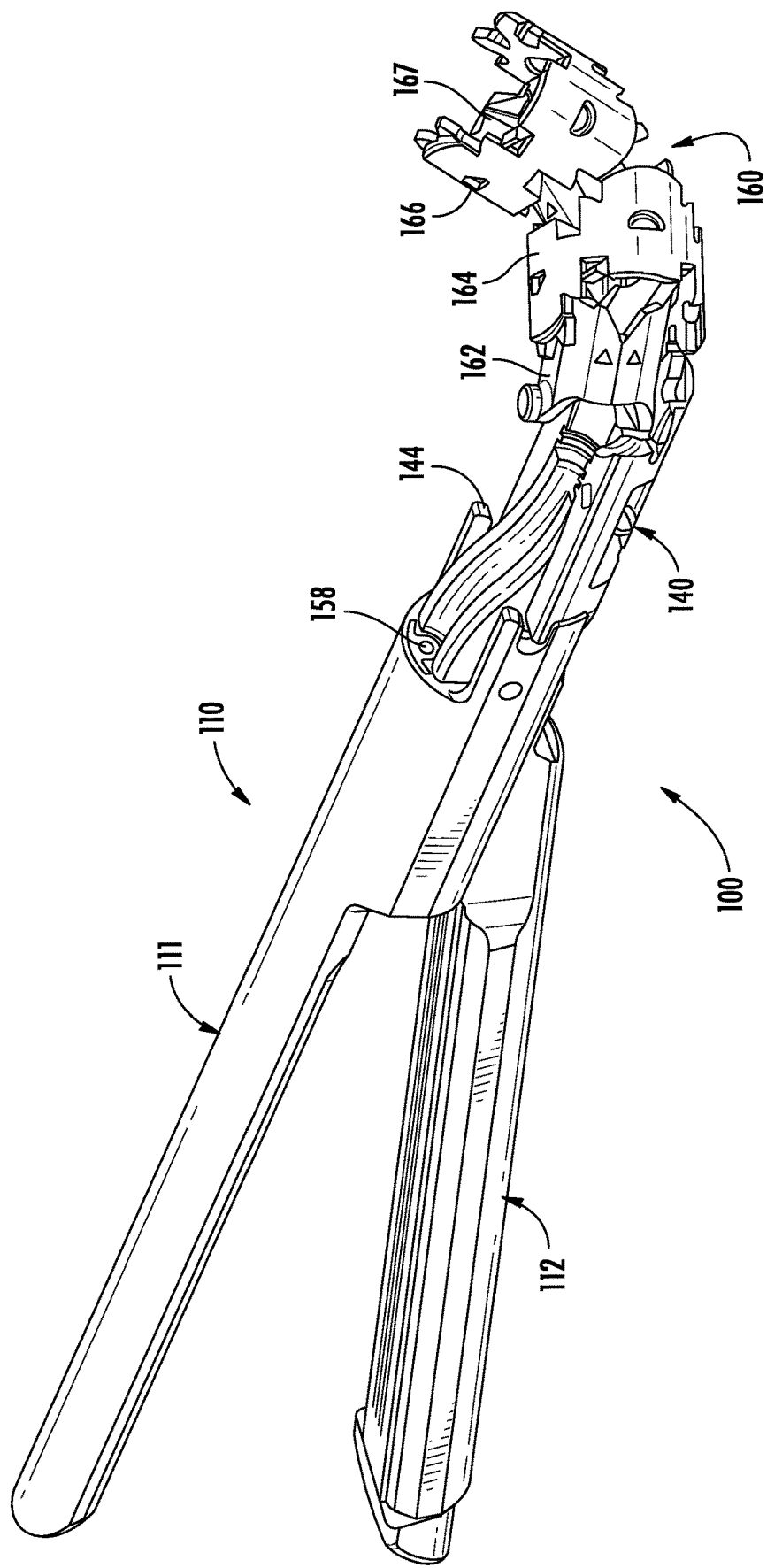
FIG. 15 is a perspective view of the end portion of an illustrative surgical instrument with parts removed.

End effector 110 may be articulated in multiple directions by an articulation mechanism. In embodiments, the articulation mechanism may be a wrist 160 as shown, although other articulation mechanisms are contemplated. As seen in FIG. 15, wrist 160 includes a plurality of articulation joints 162, 164, 166, etc. that define a bore 167 through which an actuation mechanism (in embodiments, coil 120 and drive cable 171, see FIG. 17A) may pass. Upon exiting articulation wrist 160, coil 120 enters and passes through channel 180 of clevis 140 (see FIG. 14), ultimately engaging proximal surface 153 of upper shoe 152 of drive member 150. Other articulation mechanisms within the purview of those skilled in the art may substitute for wrist 160. One suitable articulation mechanism is described for example in U.S. Publication No. 2015/0250530, the disclosure of which is hereby incorporated by reference in its entirety.

Upon actuation of the surgical instrument, drive member 150 is advanced distally through end effector 110 to move jaws 111, 112 from the open position to the closed position, after which shuttle 123 and knife 128 are advanced distally through cartridge 122 to staple and cut tissue grasped between jaws 111, 112. Drive member 150 may be any structure capable of pushing at least one of a shuttle or a knife of a surgical stapling instrument with the necessary force to effectively sever or staple human tissue. Drive member 150 may be an I-beam, an E-beam, or any other type of drive member capable of performing similar functions. Drive member 150 is movably supported on the surgical stapling instrument 100 such that it may pass distally through cartridge 122 and upper fixed jaw 111 and lower jaw 112 when the surgical stapling instrument is fired (e.g., actuated).

Figure 16:
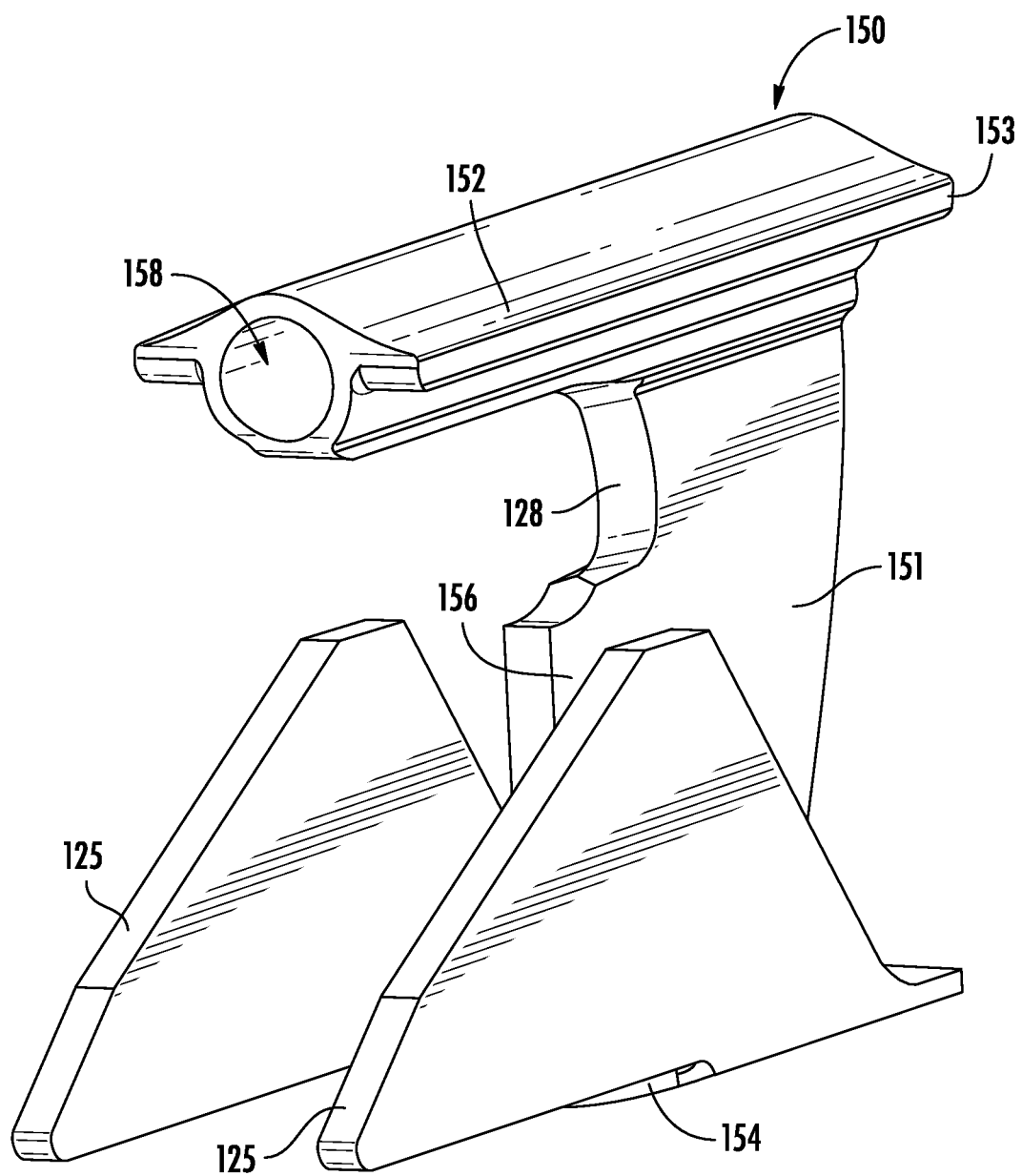
FIG. 16 is a perspective view of a drive member in accordance with the illustrative surgical instrument of FIG. 1.

As seen in FIG. 16, drive member 150 may include a body 151, upper shoe 152, lower shoe 154, and central portion 156. Upper shoe 152 of drive member 150 is substantially aligned with and translates through a channel 118 in fixed jaw 111, while lower shoe 154 of drive member 150 is substantially aligned with and translates through a channel 119 and below jaw 112. Bore 158 is formed through upper shoe 152 to receive drive cable 171 as will be described in more detail below. Proximal surface 153 of upper shoe 152 is configured to be engaged by a coil 120 of actuation assembly 190 such that coil 120 may apply force to upper shoe 152 to advance drive member 150 distally, i.e., in the direction of arrow "A" in FIG. 17B. A knife 128 may be formed on drive member 150 along the distal edge between upper shoe 152 and central portion 156. In embodiments, inclined distal portions 125 may be formed on either side of drive member 150.

Actuation assembly 190 includes a drive cable 171, a coil 120, a sheath 121 surrounding coil 120, and a drive rod 175. Drive cable 171 includes an enlarged distal end 173.

Figure 17B:
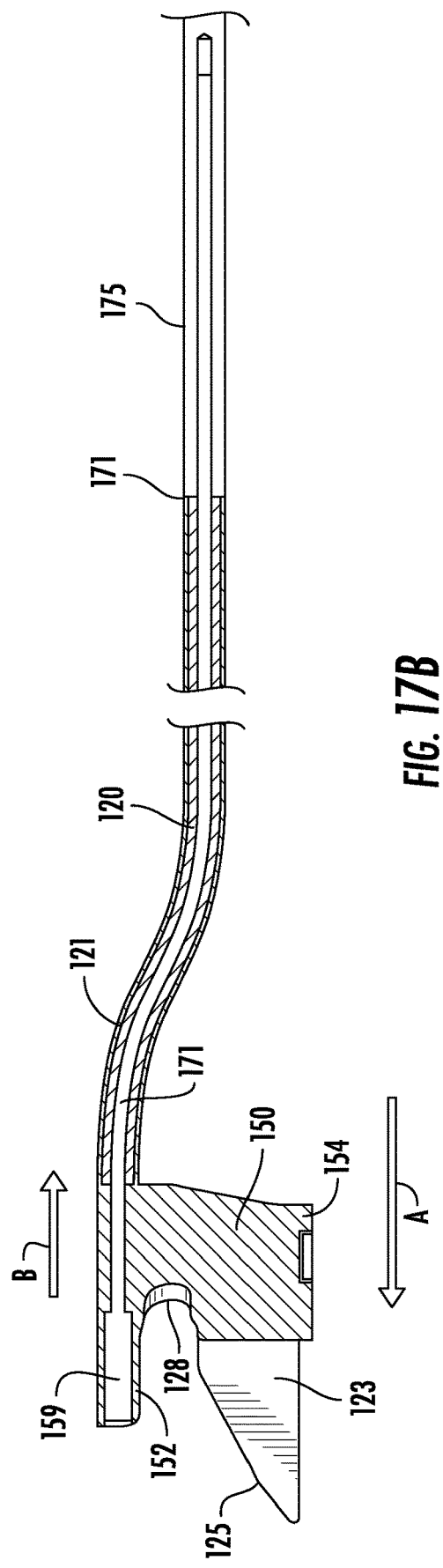
FIG. 17B is a cross-sectional side view of the actuation mechanism for a drive member in accordance with the surgical instrument of FIG. 1.

As seen in FIGS. 17A and 17B, upper shoe 152 of drive member 150 includes a bore 158 into which drive cable 171 is routed. When assembling illustrative surgical instrument 100, coil 120 and a protective sheath 121 are slipped over the free end of drive cable 171. The free end of drive cable 171 is attached to a drive rod 175 securing coil 120 and the protective sheath 121 between drive member 150 and drive rod 175 as seen in FIG. 17B. Sheath 121 may function to promote stability, smooth movement, and prevent buckling upon actuation of surgical instrument 100. Sheath 121 may be made from polyimide, or any other suitable material having the requisite strength requirements such as various reinforced plastics, a nickel titanium alloy such as NITINOL™, poly para-phenyleneterphtalamide materials such as KEVLAR™ commercially available from DuPont. Other suitable materials may be envisioned by those of skill in the art. Enlarged distal end 173 of drive cable 171 resides within an enlarged distal portion 159 of bore 158 in upper shoe 152 of body 150, such that the proximal face 157 of enlarged distal end 173 may apply a retraction force on upper shoe 152 when the drive cable 171 is pulled proximally, i.e., in the direction of arrow "B" in FIG. 17B. Drive rod 175 is operationally connected to an actuator (e.g., movable handle 102b), which allows distal translation and proximal retraction of actuation assembly 190.

In certain embodiments, the surgical instrument may be designed such that the drive member 150 is not retracted in the proximal direction after the staples have been fired. Those skilled in the art will recognize that in a manually actuated instrument, the actuator may be a movable handle, such as moveable handle 102b shown in FIG. 1; in a powered instrument the actuator may be a button (not shown) that causes a motor to act on the drive rod; and in a robotic system, the actuator may be a control device such as the control devices described below in connection with FIG. 28. Any suitable backend actuation mechanism for driving the components of the surgical stapling instrument may be used. For additional details relating to exemplary actuation mechanisms using push/pull drive cables see, e.g., commonly owned International Application WO 2018/049217, the disclosure of which is hereby incorporated by reference in its entirety.

During actuation of illustrative surgical instrument 100, drive rod 175 applies force to coil 120, thereby causing coil 120 to apply force to upper shoe 152 of drive member 150, translating it distally (i.e., in the direction of arrow "A" in FIG. 17B) initially closing jaws 111,112 and then ejecting staples 124 from stapler cartridge 122 to staple tissue. After stapling is complete, drive rod 175 applies a force in the proximal direction to effect retraction of drive member. During retraction, enlarged distal end 173 of drive cable 171 is obstructed by wall 157 of enlarged portion 159 of bore 158, causing drive cable 171 to apply force to upper shoe 152 of drive member 150, thereby translating drive member 150 in the proximal direction. One of ordinary skill in the art will appreciate that drive member 150, drive cable 171, and drive rod 175 all move in unison and remain in the same relative position to each other.

In the preferred embodiment, drive cable 171 advances drive member 150 through fixed jaw 111 (instead of through the staple cartridge jaw as in conventional surgical stapling instruments). Eliminating the internal channel for the actuation mechanism from the staple cartridge provides more space in the cartridge for the staples and for the reinforcing wall discussed above. In alternative embodiments, coil 120 of actuation assembly 190 may be coupled with lower shoe 154 instead of upper shoe 152. In these embodiments, coil 120 applies force to lower shoe 153 to advance drive member 150 distally through a channel (not shown) in the lower jaw 112. In these embodiments, coil 120 will advance at least through a portion of lower jaw 112 and staple cartridge 122.

Figure 18A:
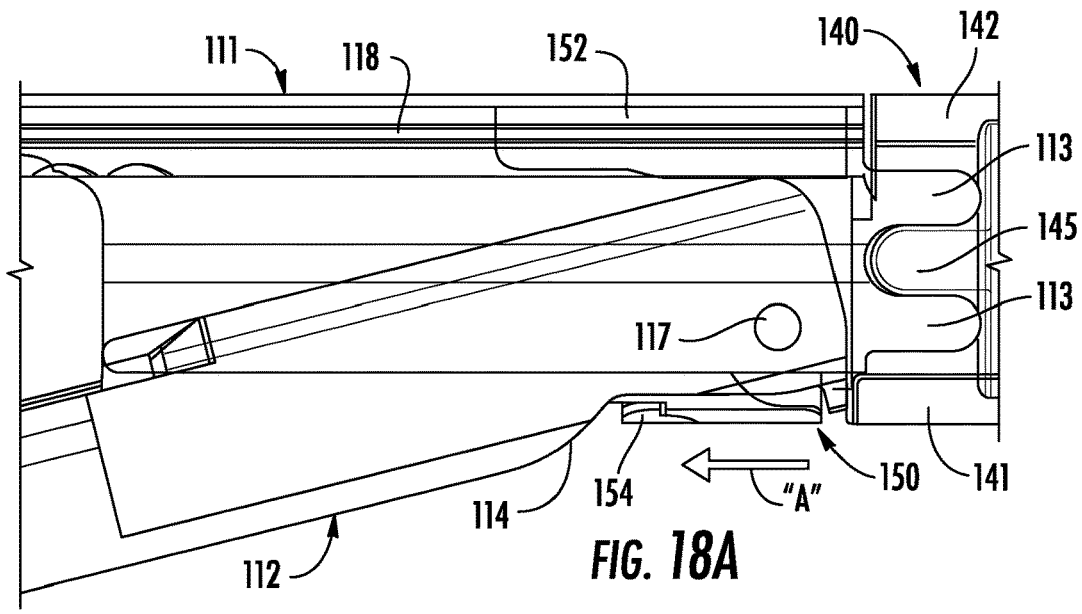
FIG. 18A shows a movable lower jaw of an illustrative surgical instrument in an open configuration.
Figure 18B:
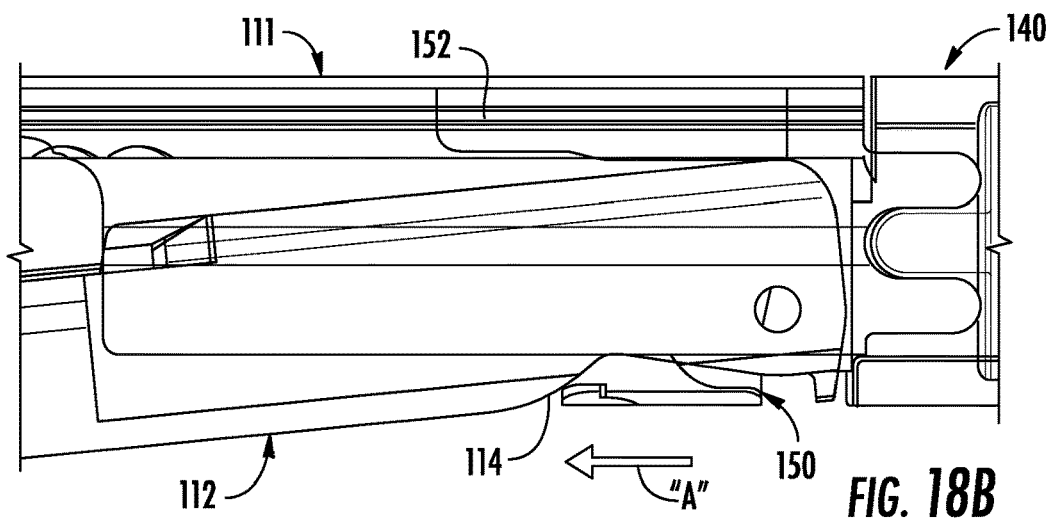
FIG. 18B shows a movable lower jaw of an illustrative surgical instrument pivoting towards a closed position.
Figure 18C:
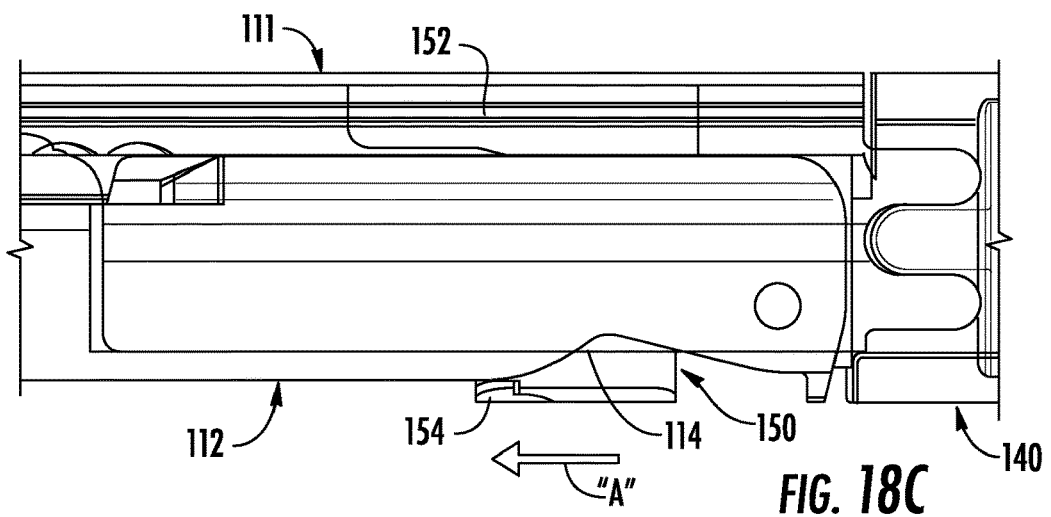
FIG. 18C shows a movable lower jaw of an illustrative surgical instrument in a closed position.

FIGS. 18A-C depict fixed jaw 111 and movable jaw 112 of illustrative surgical instrument 100 sequentially moving from an open configuration to a closed configuration. As shown in FIG. 18A, in the open configuration, drive member 150 is positioned proximally of cam surface 114 formed on movable jaw 112. As drive member 150 translates in the distal direction "A" movable jaw 112 will rotate towards the closed position around pivot 117.

In FIG. 18B, drive member 150 has come into contact with cam surface 114 of movable jaw 112. As lower portion 154 of drive member 150 rides underneath cam surface 114, drive member 150 pushes movable jaw 112, causing it to pivot towards the closed position.

FIG. 18C illustrates jaws 111, 112 in the closed position. Drive member 150 has translated distally past cam surface 114. In this position, tissue is clamped, and further advancement of the drive member will sever and staple tissue.

Figure 19:
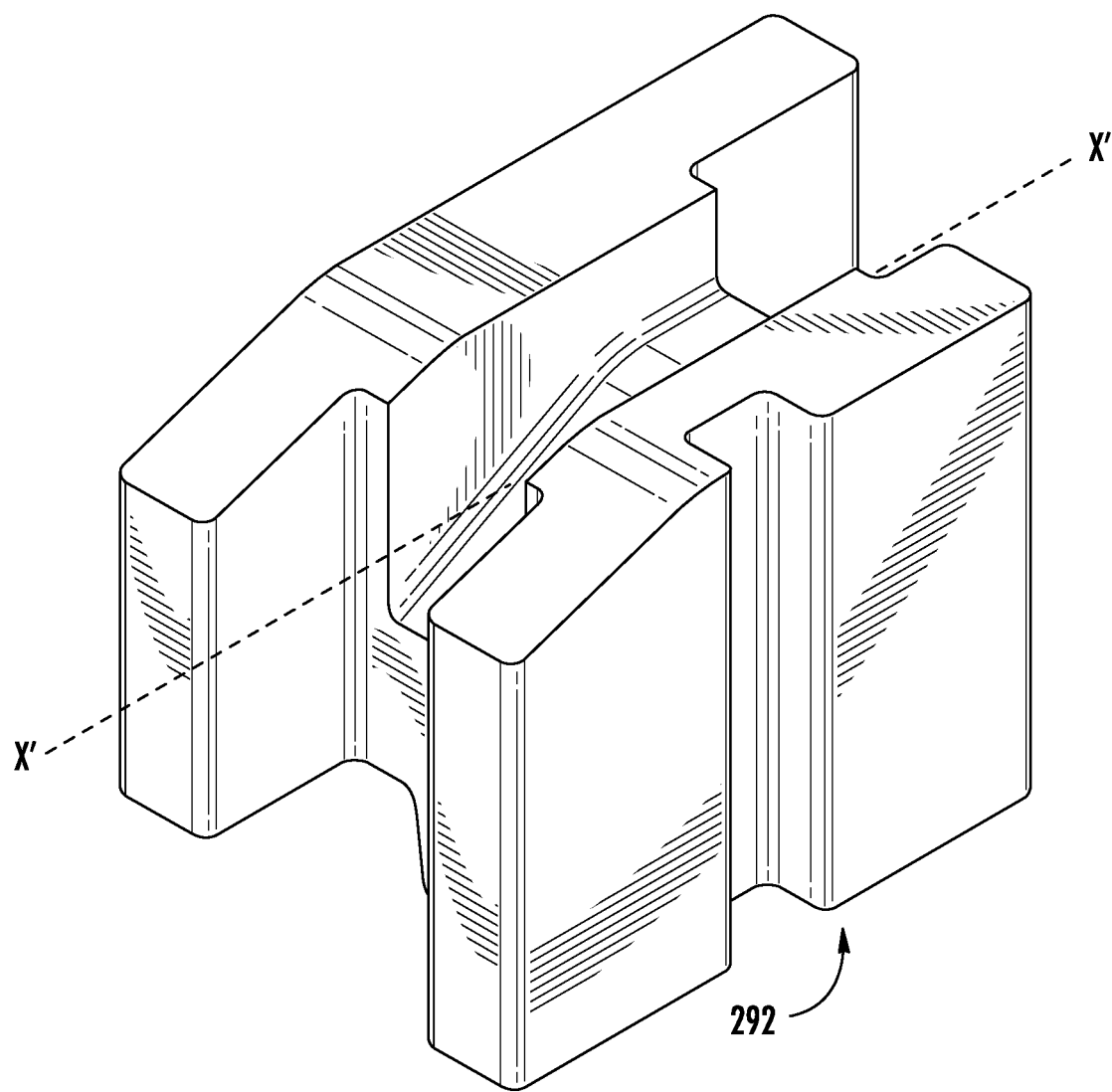
FIG. 19 is a perspective view of a switch usable with an alternative embodiment of the present disclosure.

In an alternative embodiment shown in FIG. 19, switch 191 is replaced with a switch 292 having a detachable portion configured for detachment from the remainder of switch 191 as drive member engages the switch 292. In an exemplary embodiment, switch 292 is configured to be sheared into two separate pieces along a shear plane X'-X'. In such embodiments, the surgical system may detect the force applied by a shuttle in shearing switch 292 to determine the type of reload within a given stapler cartridge. Switch 292 may be any desired shape, and may be sheared at various angles or along any line substantially parallel to the path of the drive member as it translates through a firing stroke.

In embodiments, the axial position at which switch 292 is contacted by a drive member may be adjusted by including a cutout of a predetermined height in a similar manner as above in connection with previously described embodiments to create a detectable resistance at a unique axial position. The detectable resistance may similarly be used for reload detection in a similar manner as described above. In embodiments in which switch 292 is shearable, it is envisioned that the design of switch 292 may be adjusted to shear under a specific amount of force from the drive member that also provides for a suitable amount of detectable resistance depending on the sensitivity of the control unit of the surgical system being used. Thus, the act of shearing switch 292 alone provides for a suitable detectable resistance that may be used by a control system to determine the type of stapler cartridge present by determining the axial position at which the drive member experiences the resistance associated with shearing switch 292.

Figure 20:
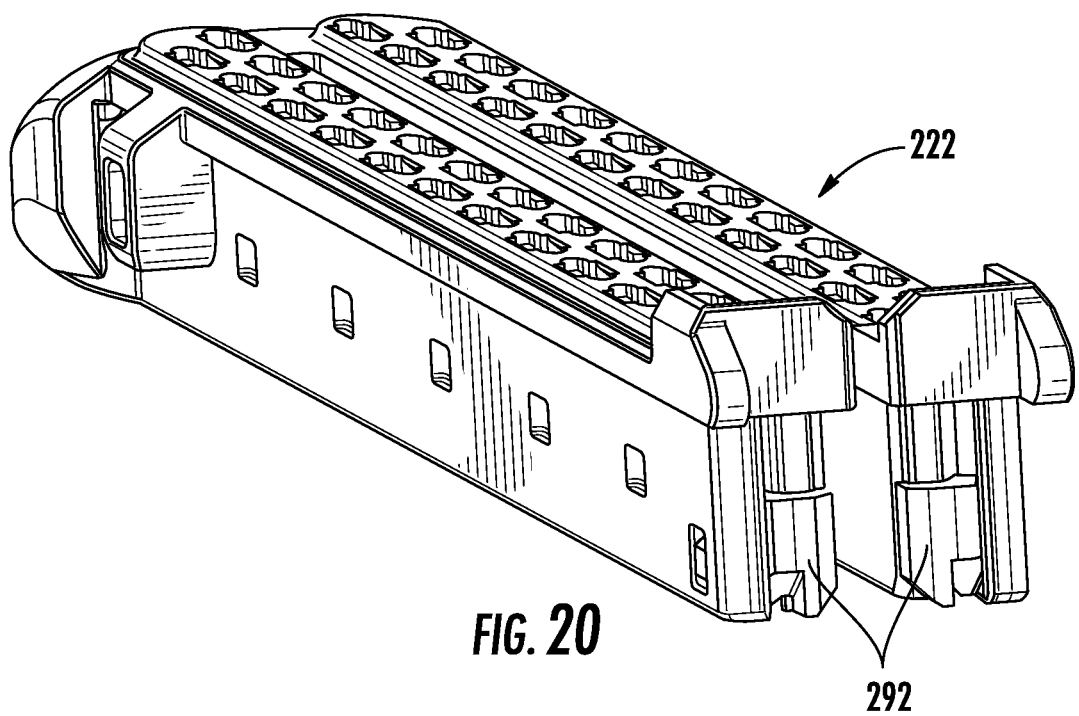
FIG. 20 is a perspective view of a stapler cartridge including the switch of FIG. 19 in a first position before actuation.
Figure 21:
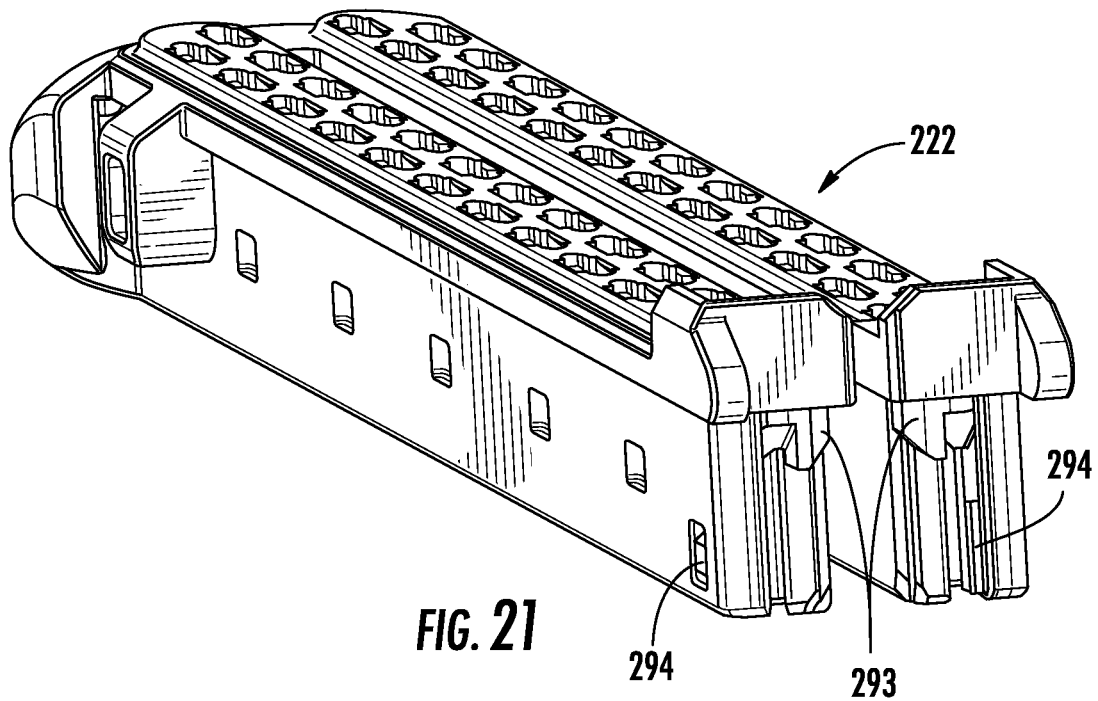
FIG. 21 is a perspective view of a stapler cartridge including the switch of FIG. 19 after actuation.
Figure 22:
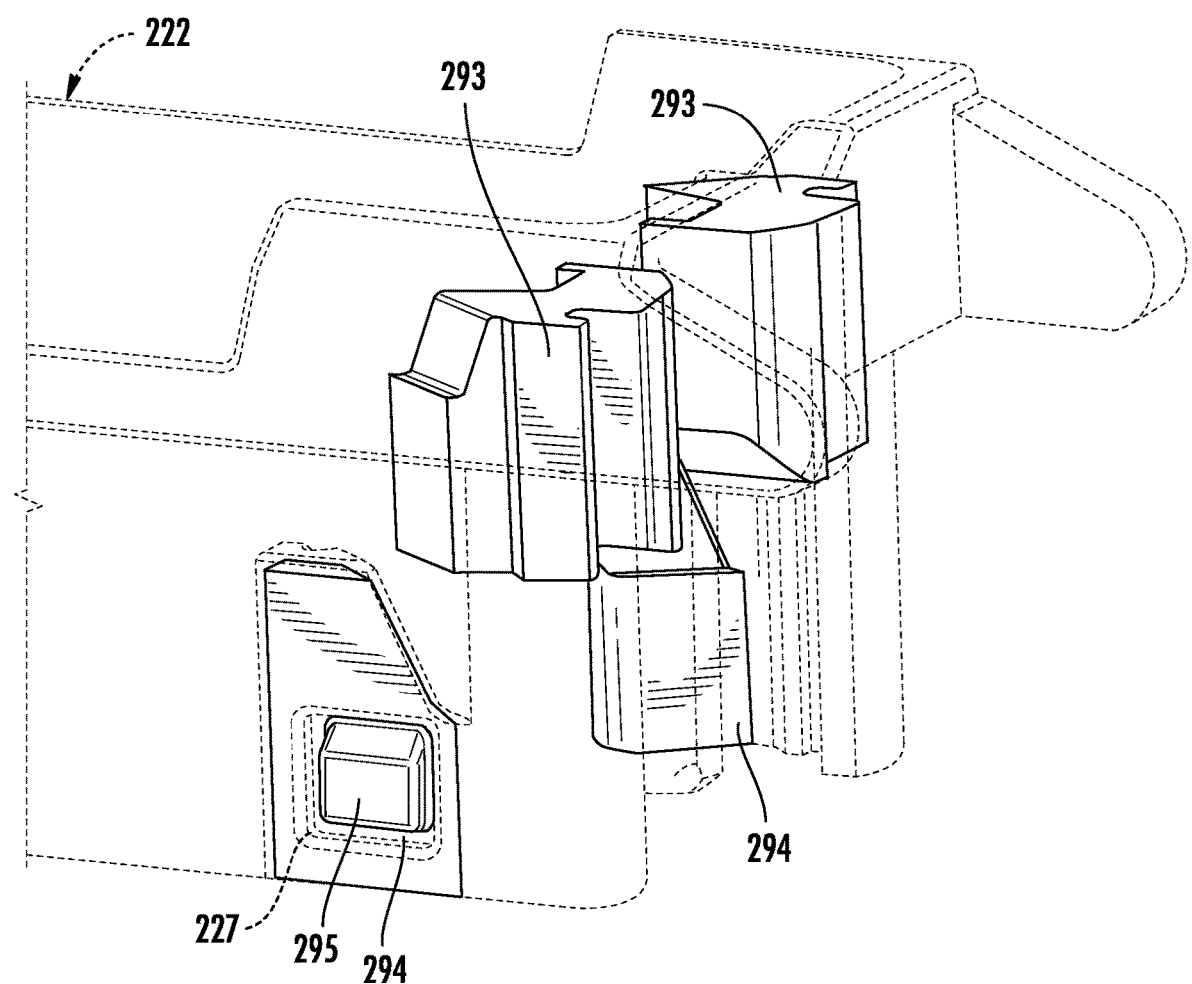
FIG. 22 is a partial side view of the proximal portion of the stapler cartridge of FIG. 21.

FIG. 20 depicts the proximal portion of an illustrative stapler cartridge having two switches 292 in an unraised position. In this configuration, actuation has not yet occurred and switch 292 has not been engaged by an inclined distal portion of a shuttle or drive member having a shuttle integrated thereon. FIGS. 21 and 22 show switch 292 after it has been engaged by a shuttle upon actuation of the surgical instrument. In this position, switch 292 has been sheared, and a movable portion 293 of switch has been forced into a raised position by a shuttle, while a stationary portion 294 remains in a substantially the same position as when switch 292 was in the unraised position. As shown in FIG. 22, stationary portion 294 of switch 292 may include a protrusion 295 configured to fit within a cutout 227 formed within a sidewall of stapler cartridge 222, helping stationary portion 294 to remain substantially unmoved throughout actuation.

Figure 23:
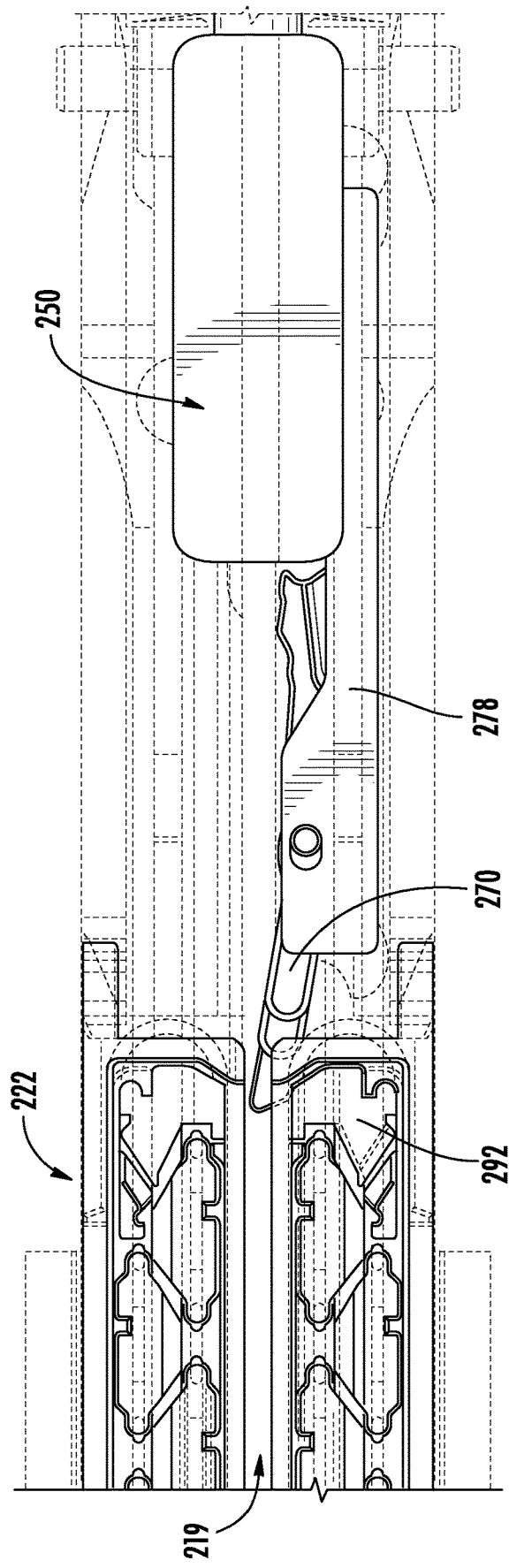
FIG. 23 is a cross-sectional top view of an illustrative end effector with a switch and stapler cartridge in accordance with FIG. 20 installed before actuation.
Figure 24:
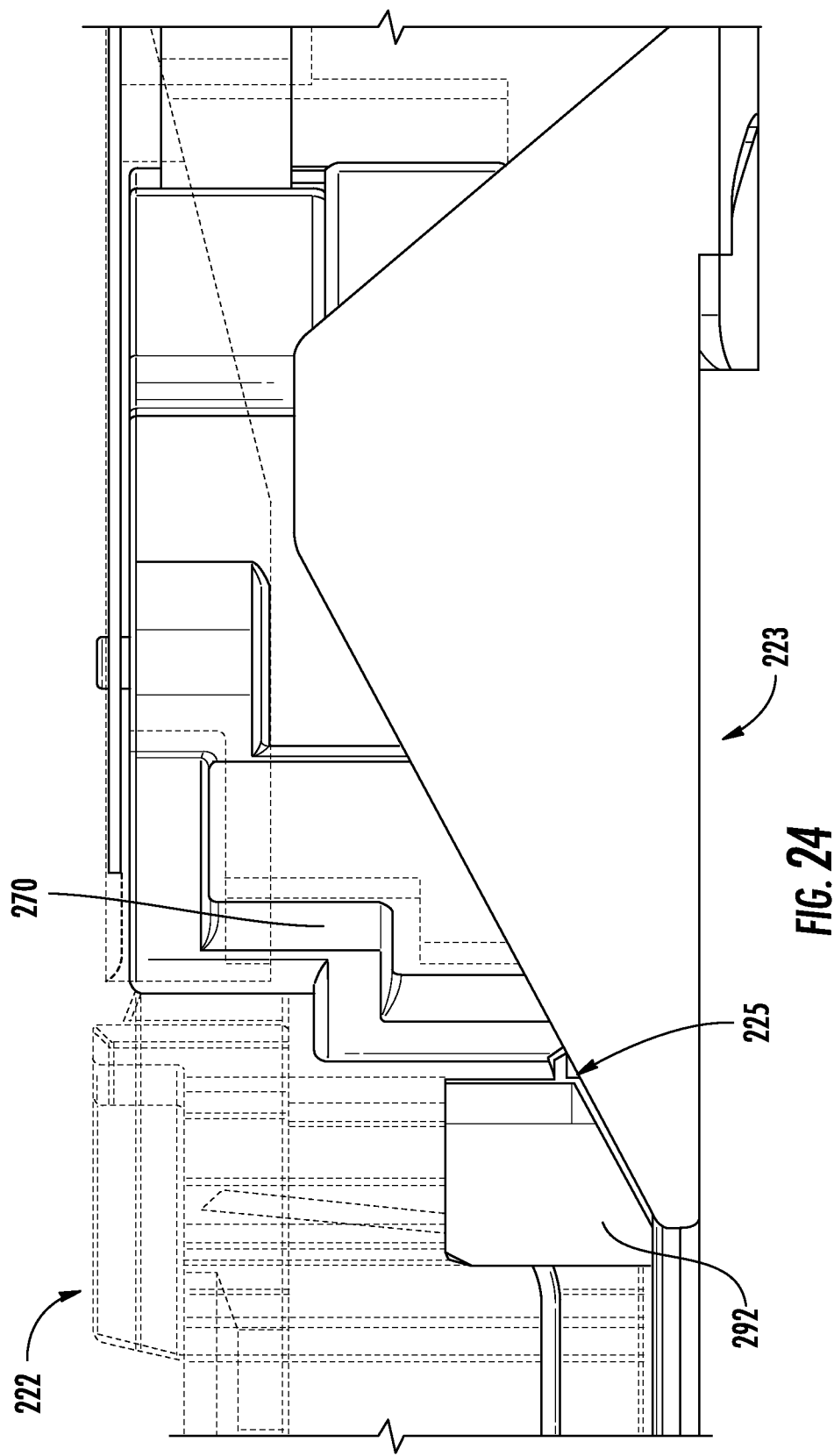
FIG. 24 is a partial side view of a portion of the illustrative end effector of FIG. 23 showing a shuttle contacting the switch upon actuation of the surgical instrument.
Figure 25:
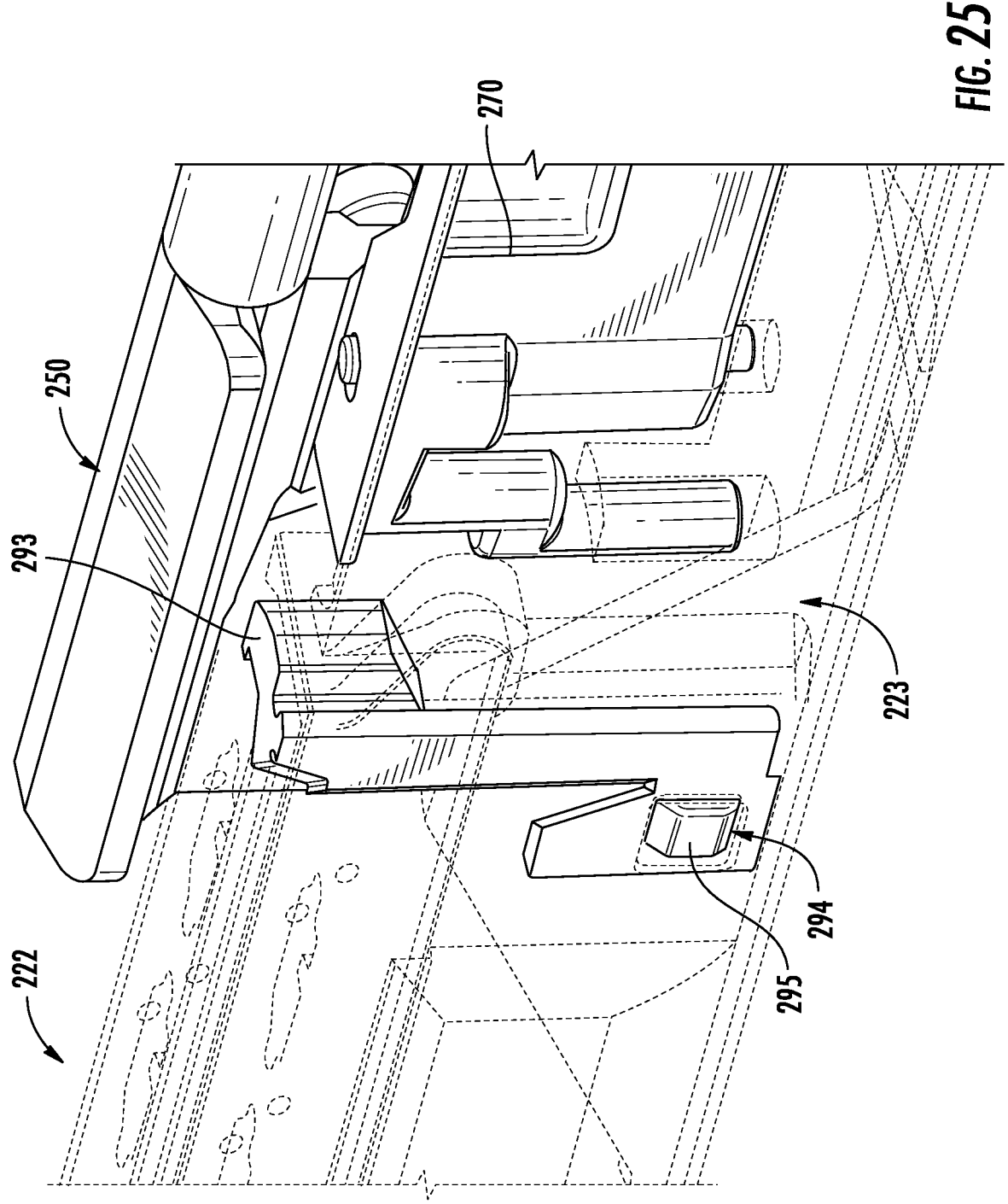
FIG. 25 is a partial side view with parts removed of a portion of the illustrative end effector of FIG. 23 showing the switch after it has been engaged by a shuttle upon actuation.

FIGS. 23-25 sequentially depict actuation of an illustrative surgical instrument having an end effector with a stapler cartridge in accordance with FIG. 20 installed.

In FIG. 23, a fresh stapler cartridge 222 having switches 292 has been installed into end effector 210 of an illustrative surgical instrument. A locking member 270 is biased by a spring 278 towards a channel 219 through which drive member 250 is configured to pass. As in the embodiments previously described, switch 292 in the unraised position maintains locking member 270 out of engagement with channel 219, thereby allowing drive member 250 to translate distally upon actuation to cut tissue and drive staples and cut tissue.

In FIG. 24, an inclined distal portion 225 of a shuttle 223 is shown driving distally to engage switch 292. Shuttle 223 may be coupled to a drive member 250 as in the embodiments previously described. In FIG. 25, the forces applied to switch 292 by shuttle 223 have caused switch 292 to be sheared into two separate pieces. Movable portion 293 of switch 292 is forced into the raised position where it is no longer aligned with locking member 270. This allows for spring 278 to force locking member 270 to swing into channel 219. In this position, drive member 250 is obstructed by locking member 270 should a user attempt to again actuate the surgical instrument. Stationary portion 294 of switch 292 remains in a substantially similar position.

Figure 26:
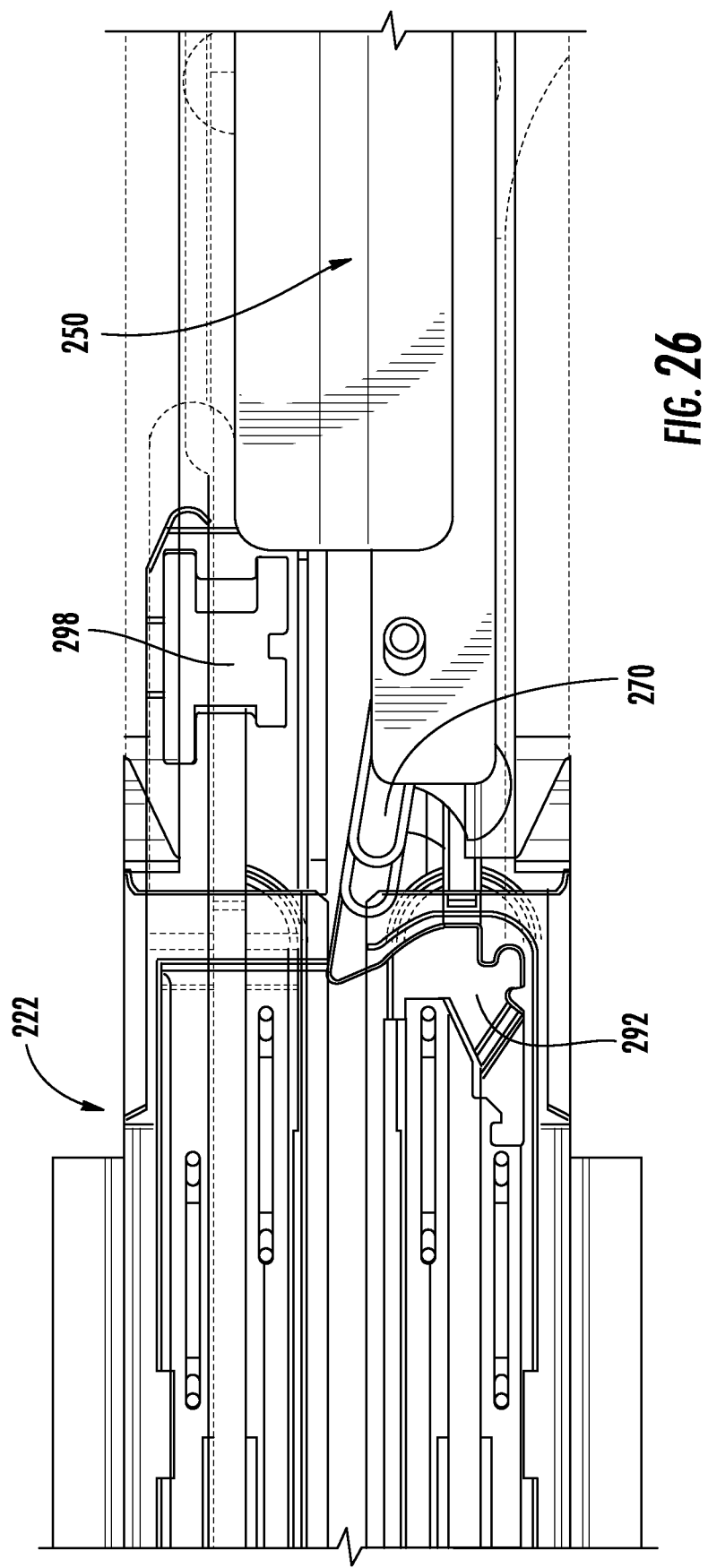
FIG. 26 shows an alternative embodiment having an illustrative stapler cartridge containing a first switch for reload detection, and a second switch for engaging locking member.

In embodiments, stapler cartridge 222 may include an additional switch 298 positioned on a proximal tail portion 224 of stapler cartridge 222 as best seen in FIG. 26. In embodiments, the engagement of shuttle 223 with switch 298 upon distal translation of drive member 250 may serve as the reload detection point. In some instances, this configuration is desirable as the reload detection point is at a more proximal position than if reload detection was accomplished using switch 292. In embodiments, switch 298 operates independently of locking member 270, and switch 292 independently activates or disables locking member 270.

Figure 27:
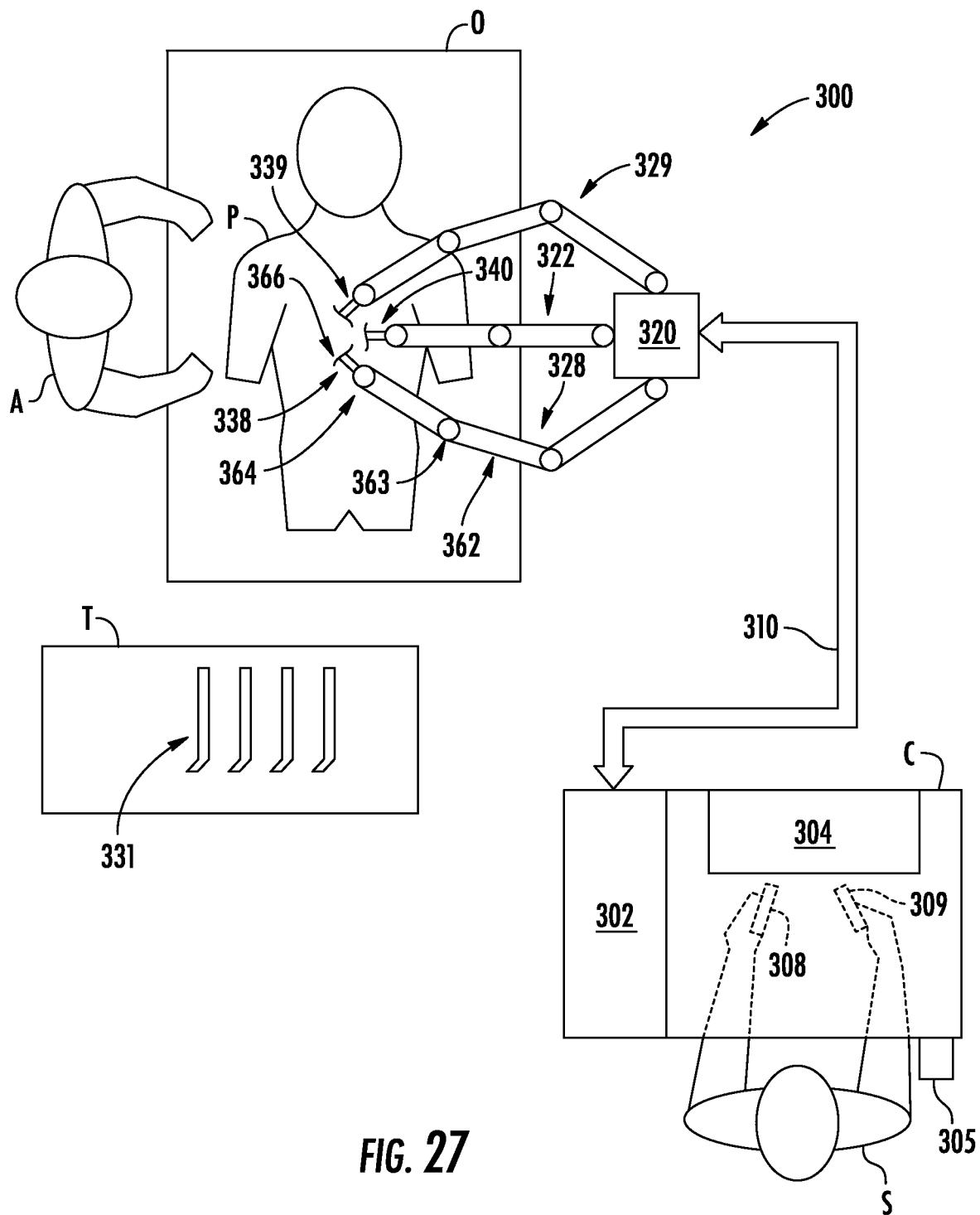
FIG. 27 illustrates a top view of an operating room employing a robotic surgical system utilizing aspects of the present disclosure.

FIG. 27 illustrates, as an example, a top view of an operating room employing a robotic surgical system. The robotic surgical system in this case is a robotic surgical system 300 including a Console ("C") utilized by a Surgeon ("S") while performing a minimally invasive diagnostic or surgical procedure, usually with assistance from one or more Assistants ("A"), on a Patient ("P") who is lying down on an Operating table ("O").

The Console includes a monitor 304 for displaying an image of a surgical site to the Surgeon, left and right manipulatable control devices 308 and 309, a foot pedal 305, and a processor 302. The control devices 308 and 309 may include any one or more of a variety of input devices such as joysticks, gloves, trigger-guns, hand-operated controllers, or the like. The processor 302 may be a dedicated computer that may be integrated into the Console or positioned next to it.

The Surgeon performs a minimally invasive surgical procedure by manipulating the control devices 308 and 309 (also referred to herein as "master manipulators") so that the processor 302 causes their respectively associated robotic arm assemblies, 328 and 329, (also referred to herein as "slave manipulators") to manipulate their respective removably coupled surgical instruments 338 and 339 (also referred to herein as "tools") accordingly, while the Surgeon views the surgical site in 3-D on the Console monitor 304 as it is captured by a stereoscopic endoscope 340.

Each of the tools 338 and 339, as well as the endoscope 340, may be inserted through a cannula or other tool guide (not shown) into the Patient so as to extend down to the surgical site through a corresponding minimally invasive incision such as incision 366. Each of the robotic arms is conventionally formed of links, such as link 362, which are coupled together and manipulated through motor controlled or active joints, such as joint 363.

The number of surgical tools used at one time and consequently, the number of robotic arms being used in the system 300 will generally depend on the diagnostic or surgical procedure and the space constraints within the operating room, among other factors. If it is necessary to change one or more of the tools being used during a procedure, the Assistant may remove the tool no longer being used from its robotic arm, and replace it with another tool 331 from a Tray ("T") in the operating room.

The monitor 304 may be positioned near the Surgeon's hands so that it will display a projected image that is oriented so that the Surgeon feels that he or she is actually looking directly down onto the operating site. To that end, images of the tools 338 and 339 may appear to be located substantially where the Surgeon's hands are located.

The processor 302 performs various functions in the system 300. One function that it performs is to translate and transfer the mechanical motion of control devices 308 and 309 to their respective robotic arms 328 and 329 through control signals over bus 310 so that the Surgeon can effectively manipulate their respective tools 338 and 339. Another important function is to implement various control system processes as described herein.

Although described as a processor, it is to be appreciated that the processor 302 may be implemented in practice by any combination of hardware, software and firmware. Also, its functions as described herein may be performed by one unit, or divided up among different components, each of which may be implemented in turn by any combination of hardware, software and firmware.

For additional details on robotic surgical systems, see, e.g., commonly owned U.S. Pat. No. 6,493,608, U.S. Pat. No. 6,671, and International Application WO 2017/132611. Each of these disclosures is herein incorporated in their entireties by this reference.

Figure 28:
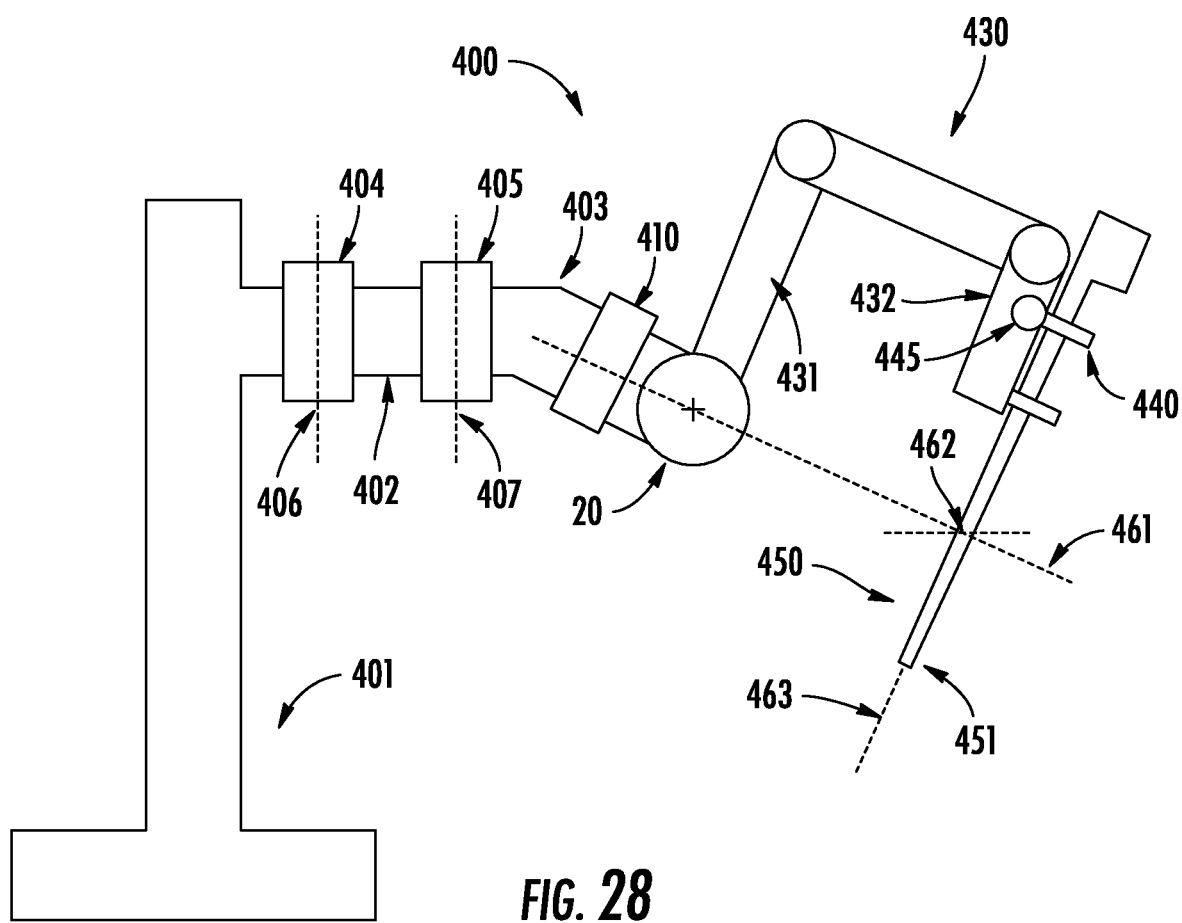
FIG. 28 illustrates a simplified side view of a robotic arm assembly that is usable with various aspects of the present disclosure.

FIG. 28 illustrates, as an example, a side view of a simplified (not necessarily in proportion or complete) illustrative robotic arm assembly 400 (which is representative of robotic arm assemblies 328 and 329) holding a surgical instrument 450 (which is representative of tools 338 and 339) for performing a surgical procedure. The surgical instrument 450 is removably held in tool holder 440. The arm assembly 400 is mechanically supported by a base 401, which may be part of a patient-side movable cart or affixed to the operating table or ceiling. It includes links 402 and 403 which are coupled together and to the base 401 through setup joints 404 and 405.

The setup joints 404 and 405 in this example are passive joints that allow manual positioning of the arm 400 when their brakes are released. For example, setup joint 404 allows link 402 to be manually rotated about axis 406, and setup joint 405 allows link 403 to be manually rotated about axis 407.

Although only two links and two setup joints are shown in this example, more or less of each may be used as appropriate in this and other robotic arm assemblies in conjunction with the present invention. For example, although setup joints 404 and 405 are useful for horizontal positioning of the arm 400, additional setup joints may be included and useful for limited vertical and angular positioning of the arm 400. For major vertical positioning of the arm 400, however, the arm 400 may also be slidably moved along the vertical axis of the base 401 and locked in position.

The robotic arm assembly 400 also includes three active joints driven by motors. A yaw joint 410 allows arm section 430 to rotate around an axis 461, and a pitch joint 420 allows arm section 430 to rotate about an axis perpendicular to that of axis 461 and orthogonal to the plane of the drawing. The arm section 430 is configured so that sections 431 and 432 are always parallel to each other as the pitch joint 420 is rotated by its motor. As a consequence, the instrument 450 may be controllably moved by driving the yaw and pitch motors so as to pivot about the pivot point 462, which is generally located through manual positioning of the setup joints 404 and 405 so as to be at the point of incision into the patient. In addition, an insertion gear 445 may be coupled to a linear drive mechanism (not shown) to extend or retract the instrument 450 along its axis 463.

Although each of the yaw, pitch and insertion joints or gears, 410, 420 and 445, is controlled by an individual joint or gear controller, the three controllers are controlled by a common master/slave control system so that the robotic arm assembly 400 (also referred to herein as a "slave manipulator") may be controlled through user (e.g., surgeon) manipulation of its associated master manipulator.

While several embodiments have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of presently disclosed embodiments. For example, the invention is not limited to the mechanisms described herein for identifying and/or deactivating stapler cartridges. Other suitable devices or mechanisms are described in co-pending and co-owned International Patent Application No. PCT/US2019/66530, filed Dec. 16, 2019 and entitled "SURGICAL INSTRUMENTS HAVING MECHANISMS FOR IDENTIFYING AND/OR DEACTIVATING STAPLER CARTRIDGES", the entire disclosure of which is incorporated herein by reference in its entirety.

Thus, the scope of the embodiments should be determined by the appended claims and their legal equivalents, rather than by the examples given.

Persons skilled in the art will understand that the devices and methods specifically described herein and illustrated in the accompanying drawings are non-limiting exemplary embodiments. The features illustrated or described in connection with one exemplary embodiment may be combined with the features of other embodiments. Various alternatives and modifications can be devised by those skilled in the art without departing from the disclosure. Accordingly, the present disclosure is intended to embrace all such alternatives, modifications and variances. As well, one skilled in the art will appreciate further features and advantages of the present disclosure based on the above-described embodiments. Accordingly, the present disclosure is not to be limited by what has been particularly shown and described, except as indicated by the appended claims.

The invention claimed is:

1. A surgical system comprising:
a stapling instrument comprising a shaft, an end effector with first and second jaws, a switch disposed on, or within, the end effector, and a drive member configured to translate distally through the shaft,
wherein the drive member is configured to contact the switch such that the switch provides a detectable resistance upon engagement with the drive member, wherein the switch is movable-relative to the first and second jaws by engagement with the drive member; and
a controller operatively coupled to the surgical stapling instrument, the controller being configured to read the detectable resistance.

2. The system of claim 1, further comprising a staple cartridge having one or more staples removably loadable into one of the first and second jaws of the end effector, wherein the controller identifies the staple cartridge based on the detectable resistance.

3. The system of claim 2, wherein the drive member contacts the switch at an axial position of the drive member, and wherein the controller identifies the staple cartridge based on said axial position.

4. The system of claim 2, wherein the drive member comprises one or more inclined distal ramps and the switch has a contact portion configured to contact the one or more distal ramps upon distal translation of the drive member through the end effector.

5. The system of claim 4, wherein the contact portion of the switch is disposed at a height relative to the drive member such that the inclined distal ramp of the drive member is located at an axial position upon contact with the contact portion.

6. The system of claim 2, wherein the switch is disposed on the staple cartridge.

7. The system of claim 1, wherein the controller is part of a robotic surgical system operatively coupled to the stapling instrument.

8. The system of claim 1, further including a locking member movable from a disabled position permitting distal translation of the drive member through a staple firing stroke, to a locking position inhibiting distal translation of the drive member through the staple firing stroke.

9. The system of claim 1, further comprising a first staple cartridge comprising a first switch and a second staple cartridge comprising a second switch, wherein the drive member is configured to contact the first switch and the control unit is configured to identify the first staple cartridge and to contact the second switch and the control unit is configured to identify the second staple cartridge.

10. A control system for a surgical stapling instrument, the system comprising:
- a first controller coupled to an actuator for translating a drive member through a channel in an end effector of the surgical stapling instrument such that the drive member contacts and moves a switch from a first position, wherein the switch at least partially extends into the channel, to a second position, wherein the switch is lateral of the drive member; and
- a second controller operatively coupled to the drive member and configured to detect a resistance encountered by the drive member as the drive member contacts the switch.

11. The control system of claim 10, wherein the second controller is configured to identify a staple cartridge within the instrument based on the resistance encountered by the drive member.

12. The control system of claim 11, wherein the second controller is configured to identify the staple cartridge based on an axial position of the drive member when the drive member encounters the resistance.

13. The control system of claim 10, wherein the drive member comprises one or more inclined distal ramps and the switch has a contact portion configured to contact the one or more distal ramps upon distal translation of the drive member through the end effector.

14. The control system of claim 13, wherein the drive member contacts the switch at an axial position of the drive member, and wherein the second controller identifies the staple cartridge based on said axial position.

15. The control system of claim 10, wherein the first and second controller are remote from the surgical instrument and form part of a robotic control system.

16. A method for controlling a surgical instrument comprising:
- translating a drive member through a shaft of the instrument and an internal channel of an end effector of the instrument such that the drive member contacts and moves a switch extending into the internal channel;
- detecting a resistance encountered by the drive member upon contact with the switch; and
- identifying a removable unit in an end effector of the instrument based on said resistance.

17. The method of claim 16, further comprising loading a staple cartridge into the end effector of the instrument and identifying the staple cartridge based on said resistance.

18. The method of claim 17, wherein the drive member comprises one or more inclined distal ramps and the switch has a contact portion configured to contact the one or more distal ramps upon distal translation of the drive member through the end effector.

19. The method of claim 18, further comprising identifying the staple cartridge based on an axial position of the drive member when the drive member encounters resistance with the contact portion of the switch.

20. The method of claim 16, wherein the resistance comprises a torque spike.

* * * * *